US008735094B2

(12) United States Patent
Zhu

(10) Patent No.: US 8,735,094 B2
(45) Date of Patent: May 27, 2014

(54) *YARROWIA* N-ALKANE-HYDROXYLATING CYTOCHROME P450 PROMOTER REGIONS FOR GENE EXPRESSION IN YEAST

(75) Inventor: Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 138 days.

(21) Appl. No.: 13/437,219

(22) Filed: Apr. 2, 2012

(65) Prior Publication Data
US 2013/0089910 A1 Apr. 11, 2013

Related U.S. Application Data

(60) Provisional application No. 61/471,736, filed on Apr. 5, 2011.

(51) Int. Cl.
*C12P 21/06* (2006.01)
*C07H 21/02* (2006.01)

(52) U.S. Cl.
USPC ........................................ 435/69.1; 536/23.1

(58) Field of Classification Search
USPC ........................................ 435/69.1; 536/23.1
See application file for complete search history.

(56) References Cited

U.S. PATENT DOCUMENTS

| | | | |
|---|---|---|---|
| 6,673,613 B2 | 1/2004 | Craft et al. | |
| 7,388,084 B2 * | 6/2008 | Wilson et al. | 536/23.1 |
| 2005/0014270 A1 | 1/2005 | Picataggio et al. | |
| 2010/0062502 A1 | 3/2010 | Hong et al. | |

FOREIGN PATENT DOCUMENTS

| | | |
|---|---|---|
| WO | 2004016756 A2 | 2/2004 |
| WO | 2012027689 A1 | 3/2012 |
| WO | 2012027698 A1 | 3/2012 |

OTHER PUBLICATIONS

International Search Report, International Patent Application No. PCT/US2012/031909, Mailed Jul. 5, 2012.
Database Accession No. AZT93123, *Yarrowia lipolytica* ALK2LM1 Promotor DNA, SEQ:93, Retrieved From EBI Accession No. GSN:AZT93123, Apr. 26, 2012.
Database Accession No. AZT79773, Plasmid PYPS233 Related 1019 BP Stuffer Fragment, SEQ ID:230, Retrieved From EBI Accession No. GSN:AZT79773, Mar. 1, 2012.
Dujon et al., Genome Evolution in Yeasts, Nature, vol. 430 (2004), pp. 35-44.
Kogure et al., N-Alkane and Clofibrate, a Peroxisome Proliferator, Activate Transcription of ALK2 Gene Encoding Cytochrome P450ALK2 Through Distinct CIS-Acting Promoter Elements in *Candida maltosa*, Biochemical and Biophysical Research Communications, vol. 329 (2005), pp. 78-86.
Sanglard et al., Characterization of the Alkane-Inducible Cytochrome P450 (P450ALK) Gene From the Yeast *Candida tropicalis*: Identification of a New P450 Gene Family, Gene, vol. 76 (1989), pp. 121-136.
Seghezzi et al., Characterization of a Second Alkane-Inducible Cytochrome P450-Encoding Gene, CYP52A2, From *Candida tropicalis*, Gene, vol. 106 (1991), pp. 51-60.
Struhl et al., Yeast H1S3 Expression in *Escherichia coli* Depends Upon Fortuitous Homology Between Eukaryotic and Prokaryotic Promoter Elements, J. Mol. Biol., vol. 191 (1986), pp. 221-229.

* cited by examiner

*Primary Examiner* — Karen Cochrane Carlson

(57) ABSTRACT

Promoter regions associated with the *Yarrowia lipolytica* n-alkane-hydroxylating cytochrome P450 (ALK2) gene are disclosed and have been found to be particularly effective for the expression of heterologous genes in yeast. These promoter regions will be useful for driving high-level expression of genes involved in the production of omega-3 and omega-6 fatty acids.

16 Claims, 14 Drawing Sheets

FIG. 2A

| | | 1 | GTAAWAGACGWGCCGCGATGCATTGAGTGCCTWAGCCCCAGCTTCGAAATCAAGCTTTC | 60 |

Figure 1:
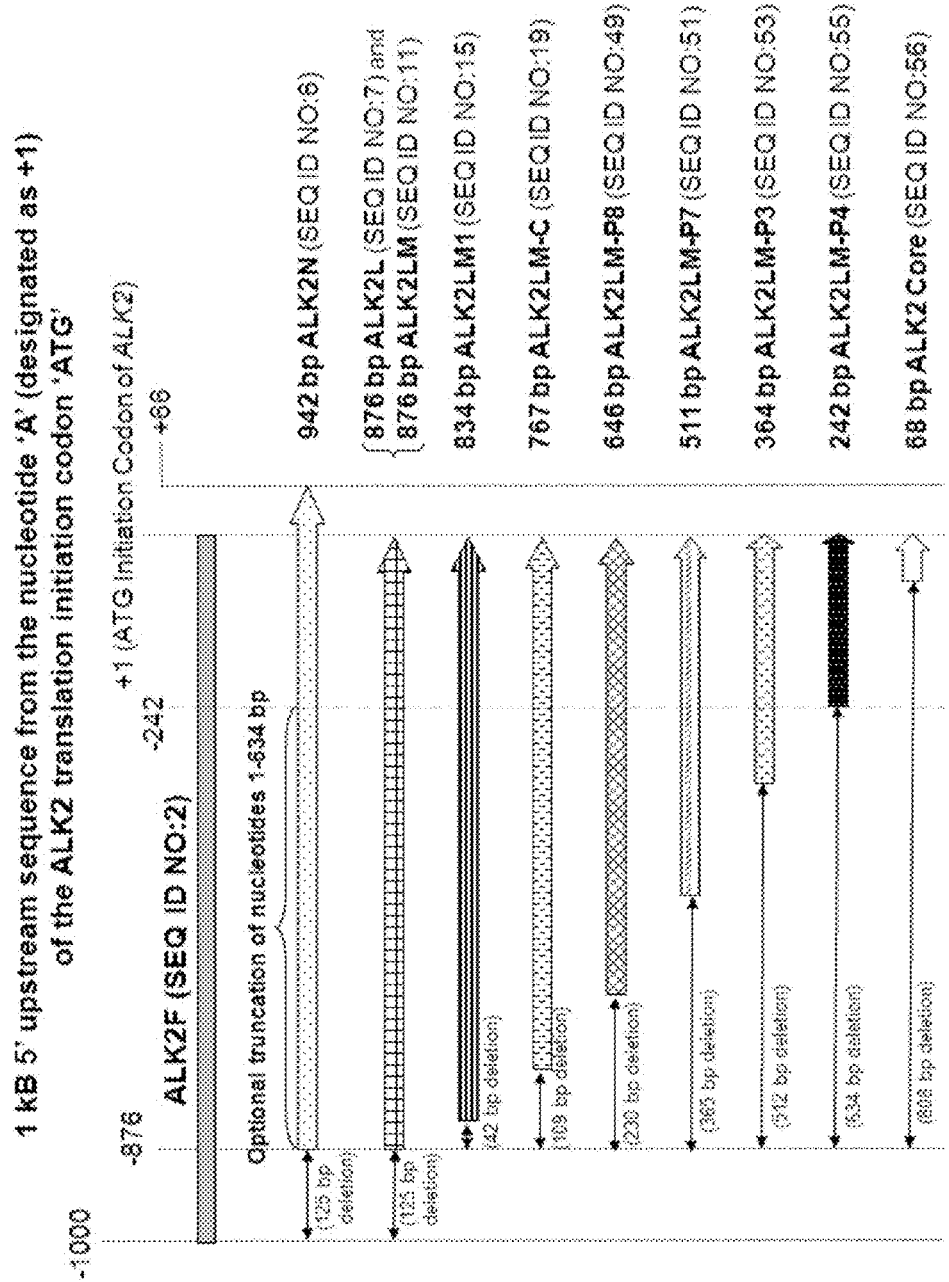

ALK2F (SEQ ID NO:2)
942 bp ALK2N (SEQ ID NO:6)
876 bp ALK2L (SEQ ID NO:7)
876 bp ALK2LM (SEQ ID NO:11)
838 bp ALK2LM1-S (SEQ ID NO:27)
834 bp ALK2LM1 (SEQ ID NO:15)
840 bp ALK2LM1-PP6 (SEQ ID NO:47)
839 bp ALK2LM1-PP5 (SEQ ID NO:43)
837 bp ALK2LM1-PP2 (SEQ ID NO:39)
835 bp ALK2LM1-PP1 (SEQ ID NO:35)
835 bp ALK2LM1-P (SEQ ID NO:31)
767 bp ALK2LM-C (SEQ ID NO:19)
646 bp ALK2LM-P8 (SEQ ID NO:49)
511 bp ALK2LM-P7 (SEQ ID NO:51)
364 bp ALK2LM-P3 (SEQ ID NO:53)
242 bp ALK2LM-P4 (SEQ ID NO:55)
68 bp ALK2 Core (SEQ ID NO:56)

| | | 61 | CATTCCTGAGCCTGAGGAATGGGACGAGGGGGTGAAAATTGGGGCTGGAAGTCGCTTGA | 120 |

ALK2F (SEQ ID NO:2)
942 bp ALK2N (SEQ ID NO:6)
876 bp ALK2L (SEQ ID NO:7)
876 bp ALK2LM (SEQ ID NO:11)
838 bp ALK2LM1-S (SEQ ID NO:27)
834 bp ALK2LM1 (SEQ ID NO:15)
840 bp ALK2LM1-PP6 (SEQ ID NO:47)
839 bp ALK2LM1-PP5 (SEQ ID NO:43)
837 bp ALK2LM1-PP2 (SEQ ID NO:39)
835 bp ALK2LM1-PP1 (SEQ ID NO:35)
835 bp ALK2LM1-P (SEQ ID NO:31)
767 bp ALK2LM-C (SEQ ID NO:19)
646 bp ALK2LM-P8 (SEQ ID NO:49)
511 bp ALK2LM-P7 (SEQ ID NO:51)
364 bp ALK2LM-P3 (SEQ ID NO:53)
242 bp ALK2LM-P4 (SEQ ID NO:55)
68 bp ALK2 Core (SEQ ID NO:56)

| | | | 481 | 540 |
|---|---|---|---|---|
| ALK2F | (SEQ ID NO:2) | (471) | GCGGGGTAGCAGGATACTG | ACTACAGTAGTACGATTGCTTGCTACTGCTTGTAGCAA |
| 942 bp ALK2N | (SEQ ID NO:6) | (347) | GCGGGGTAGCAGGATACTG | ACTACAGTAGTACGATTGCTTGCTACTGCTTGTAGCAA |
| 876 bp ALK2L | (SEQ ID NO:7) | (347) | GCGGGGTAGCAGGATACTG | ACTACAGTAGTACGATTGCTTGCTACTGCTTGTAGCAA |
| 876 bp ALK2LM | (SEQ ID NO:11) | (347) | GCGGGGTAGCAGGATACTG | ACTACAGTAGTACGATTGCTTGCTACTGCTTGTAGCAA |
| 838 bp ALK2LM1-S | (SEQ ID NO:27) | (309) | GCGGGGTAGCAGGATACTG | ACTACAGTAGTACGATTGCTTGCTACTGCTTGTAGCAA |
| 834 bp ALK2LM1 | (SEQ ID NO:15) | (305) | GCGGGGTAGCAGGATACTG | ACTACAGTAGTACGATTGCTTGCTACTGCTTGTAGCAA |
| 840 bp ALK2LM1-PP6 | (SEQ ID NO:47) | (311) | GCGGGGTAGCAGGATACTG | ACTACAGTAGTACGATTGCTTGCTACTGCTTGTAGCAA |
| 839 bp ALK2LM1-PP5 | (SEQ ID NO:43) | (306) | GCGGGGTAGCAGGATACTG | ACTACAGTAGTACGATTGCTTGCTACTGCTTGTAGCAA |
| 837 bp ALK2LM1-PP2 | (SEQ ID NO:39) | (306) | GCGGGGTAGCAGGATACTGTTA | ACTACAGTAGTACGATTGCTTGCTACTGCTTGTAGCAA |
| 835 bp ALK2LM1-PP1 | (SEQ ID NO:35) | (306) | GCGGGGTAGCAGGATACTG | ACTACAGTAGTACGATTGCTTGCTACTGCTTGTAGCAA |
| 835 bp ALK2LM1-P | (SEQ ID NO:31) | (306) | GCGGGGTAGCAGGATACTG | ACTACAGTAGTACGATTGCTTGCTACTGCTTGTAGCAA |
| 767 bp ALK2LM-C | (SEQ ID NO:19) | (238) | GCGGGGTAGCAGGATACTG | ACTACAGTAGTACGATTGCTTGCTACTGCTTGTAGCAA |
| 646 bp ALK2LM-P8 | (SEQ ID NO:49) | (117) | GCGGGGTAGCAGGATACTG | ACTACAGTAGTACGATTGCTTGCTACTGCTTGTAGCAA |
| 511 bp ALK2LM-P7 | (SEQ ID NO:51) | (1) | ------------------- | -------------------------------------- |
| 364 bp ALK2LM-P3 | (SEQ ID NO:53) | (1) | ------------------- | -------------------------------------- |
| 242 bp ALK2LM-P4 | (SEQ ID NO:55) | (1) | ------------------- | -------------------------------------- |
| 68 bp ALK2 Core | (SEQ ID NO:56) | (1) | ------------------- | -------------------------------------- |

| | | | 541 | 600 |
|---|---|---|---|---|
| ALK2F | (SEQ ID NO:2) | (527) | TTACCTTTACTGTAGGTAGGGAGGACCACACCTCCTGGTTTCAATGTCTTCAATGTCTTCCTCGCCTCGGCCTCGACAAAG |
| 942 bp ALK2N | (SEQ ID NO:6) | (403) | TTACCTTTACTGTAGGTAGGGAGGACCACACCTCCTGGTTTCAATGTCTTCAATGTCTTCCTCGCCTCGGCCTCGACAAAG |
| 876 bp ALK2L | (SEQ ID NO:7) | (403) | TTACCTTTACTGTAGGTAGGGAGGACCACACCTCCTGGTTTCAATGTCTTCAATGTCTTCCTCGCCTCGGCCTCGACAAAG |
| 876 bp ALK2LM | (SEQ ID NO:11) | (403) | TTACCTTTACTGTAGGTAGGGAGGACCACACCTCCTGGTTTCAATGTCTTCAATGTCTTCCTCGCCTCGGCCTCGACAAAG |
| 838 bp ALK2LM1-S | (SEQ ID NO:27) | (365) | TTACCTTTACTGTAGGTAGGGAGGACCACACCTCCTGGTTTCAATGTCTTCAATGTCTTCCTCGCCTCGGCCTCGACAAAG |
| 834 bp ALK2LM1 | (SEQ ID NO:15) | (361) | TTACCTTTACTGTAGGTAGGGAGGACCACACCTCCTGGTTTCAATGTCTTCAATGTCTTCCTCGCCTCGGCCTCGACAAAG |
| 840 bp ALK2LM1-PP6 | (SEQ ID NO:47) | (367) | TTACCTTTACTGTAGGTAGGGAGGACCACACCTCCTGGTTTCAATGTCTTCAATGTCTTCCTCGCCTCGGCCTCGACAAAG |
| 839 bp ALK2LM1-PP5 | (SEQ ID NO:43) | (366) | TTACCTTTACTGTAGGTAGGGAGGACCACACCTCCTGGTTTCAATGTCTTCAATGTCTTCCTCGCCTCGGCCTCGACAAAG |
| 837 bp ALK2LM1-PP2 | (SEQ ID NO:39) | (362) | TTACCTTTACTGTAGGTAGGGAGGACCACACCTCCTGGTTTCAATGTCTTCAATGTCTTCCTCGCCTCGGCCTCGACAAAG |
| 835 bp ALK2LM1-PP1 | (SEQ ID NO:35) | (362) | TTACCTTTACTGTAGGTAGGGAGGACCACACCTCCTGGTTTCAATGTCTTCAATGTCTTCCTCGCCTCGGCCTCGACAAAG |
| 835 bp ALK2LM1-P | (SEQ ID NO:31) | (362) | TTACCTTTACTGTAGGTAGGGAGGACCACACCTCCTGGTTTCAATGTCTTCAATGTCTTCCTCGCCTCGGCCTCGACAAAG |
| 767 bp ALK2LM-C | (SEQ ID NO:19) | (294) | TTACCTTTACTGTAGGTAGGGAGGACCACACCTCCTGGTTTCAATGTCTTCAATGTCTTCCTCGCCTCGGCCTCGACAAAG |
| 646 bp ALK2LM-P8 | (SEQ ID NO:49) | (173) | TTACCTTTACTGTAGGTAGGGAGGACCACACCTCCTGGTTTCAATGTCTTCAATGTCTTCCTCGCCTCGGCCTCGACAAAG |
| 511 bp ALK2LM-P7 | (SEQ ID NO:51) | (38) | TTACCTTTACTGTAGGTAGGGAGGACCACACCTCCTGGTTTCAATGTCTTCAATGTCTTCCTCGCCTCGGCCTCGACAAAG |
| 364 bp ALK2LM-P3 | (SEQ ID NO:53) | (1) | ------------------- | -------------------------------------- |
| 242 bp ALK2LM-P4 | (SEQ ID NO:55) | (1) | ------------------- | -------------------------------------- |
| 68 bp ALK2 Core | (SEQ ID NO:56) | (1) | ------------------- | -------------------------------------- |

FIG. 2F

[Sequence alignment figure showing nucleotide sequences for multiple ALK2 constructs aligned from positions 601-660 and 661-720. The constructs listed (with SEQ ID NOs) are:]

- ALK2F (SEQ ID NO:2) (587)
- 942 bp ALK2N (SEQ ID NO:6) (463)
- 876 bp ALK2L (SEQ ID NO:7) (463)
- 838 bp ALK21M-S (SEQ ID NO:11) (425)
- 834 bp ALK21M (SEQ ID NO:15) (421)
- 840 bp ALK21M1 (SEQ ID NO:47) (427)
- 839 bp ALK21M1-PP6 (SEQ ID NO:43) (426)
- 837 bp ALK21M1-PP5 (SEQ ID NO:39) (424)
- 835 bp ALK21M1-PP2 (SEQ ID NO:35) (422)
- 835 bp ALK21M1-PP1 (SEQ ID NO:31) (422)
- 767 bp ALK21M1-C (SEQ ID NO:19) (354)
- 646 bp ALK21M1-P8 (SEQ ID NO:49) (233)
- 511 bp ALK21M1-P7 (SEQ ID NO:51) (98)
- 364 bp ALK21M1-P3 (SEQ ID NO:53) (1)
- 242 bp ALK21M1-P4 (SEQ ID NO:55) (1)
- 68 bp ALK2 Core (SEQ ID NO:56) (1)

[Second block, positions 661-720, with reference numbers (645), (521), (521), (483), (479), (485), (484), (482), (480), (480), (412), (291), (156), (9), (1), (1)]

| | | |
|---|---|---|
| ALK2F | (SEQ ID NO:2) | (1001) |
| 942 bp ALK2N | (SEQ ID NO:6) | (941) CC |
| 876 bp ALK2L | (SEQ ID NO:7) | (877) -- |
| 876 bp ALK21M1-S | (SEQ ID NO:11) | (877) -- |
| 838 bp ALK21M1 | (SEQ ID NO:27) | (839) -- |
| 934 bp ALK21M1 | (SEQ ID NO:15) | (835) -- |
| 840 bp ALK21M1-PP6 | (SEQ ID NO:47) | (841) -- |
| 839 bp ALK21M1-PP5 | (SEQ ID NO:43) | (840) -- |
| 837 bp ALK21M1-PP2 | (SEQ ID NO:39) | (838) -- |
| 835 bp ALK21M1-PP1 | (SEQ ID NO:35) | (836) -- |
| 835 bp ALK21M1-P | (SEQ ID NO:31) | (836) -- |
| 767 bp ALK21M-C | (SEQ ID NO:19) | (768) -- |
| 646 bp ALK21M-P8 | (SEQ ID NO:49) | (647) -- |
| 511 bp ALK21M-P7 | (SEQ ID NO:51) | (512) -- |
| 364 bp ALK21M-P3 | (SEQ ID NO:53) | (365) -- |
| 242 bp ALK21M-P4 | (SEQ ID NO:55) | (243) -- |
| 68 bp ALK2 Core | (SEQ ID NO:56) | (69) -- |

1081

SEQUENCE LISTING

```
<160> NUMBER OF SEQ ID NOS: 58

<210> SEQ ID NO 1
<211> LENGTH: 2872
<212> TYPE: DNA
<213> ORGANISM: Yarrowia lipolytica
<220> FEATURE:
<221> NAME/KEY: misc_feature
<222> LOCATION: (1)..(2872)
<223> OTHER INFORMATION: YALI0F01320g locus (ALK2 gene)
<220> FEATURE:
<221> NAME/KEY: misc_feature
<222> LOCATION: (1001)..(1003)
<223> OTHER INFORMATION: translation initiation codon 'ATG'; nucleotide
      'A' (designated as +1)

<400> SEQUENCE: 1
gtaatagacg tgcggcgatg cattgagttg ccttagcccc agcttcgaaa tcaagctttc      60
cattcctgag cctgaggaat gggacggagg gggtgaaaat tggggctgga agtcgcttga     120
ataaattctc cgaaatggaa atccaaagac cccaagtgga tttatttttt cgagatttta     180
cagatatttc tcgcagtttt tcacgtcccc ttgtccttgt cctattgttt caaataaact     240
ctcgtctact gatttcacat ggaacctttg ctatttcggg gataaccccc tttgccattg     300
cacgatggac gtggcaaaag aaagatcgcc ctgcggggat acttatcatg tggtcacatg     360
```

```
ctgtgattag aaataaagaa aaaggtgctt ttttggcgct gtgattaaca tctcgtctgc    420
cgtgctctac tagtcgcaat agcaaaaact cgcttaatag tgtgcatagt gcggggtagc    480
aggatactga actacagtac gatttgcttg ctactgcttg tagcaattac ctttactgta    540
gggaccacac ctcctggttt caatgtcttt cctcgcctcg acaaagcaaa actgtcaccc    600
aatcacacct tgttcatatt cattagtgca tccgttaacc ttgacatgac acttctcata    660
ctagtgatag ggctgtagtt gagacaagtt gattcacacg gatacataca aagcctcaga    720
gagcaaatgt tatatactca gggaccgacc aatcaaaaaa acacactcct aataaccacc    780
atttccatct acgcgtactc actctgtcag ctgccccaca ttgcccaatg cacaatgcac    840
aatgatgtgt gcaaacaacg caatcaaaag tctatgcatg ctgaccaaac tctgatcacc    900
aagttgcgaa catgaaaaag aagacctgtg tatatataag taagggggag agccctaact    960
agatctttcg aaaaccccccc gaccttcacc ttccacaacc atgatcatct tatacgtttt   1020
ggccgttgcg gtctccttcc tcatcttcaa gagagtcacc tacacgatgc gaagccgaga   1080
gctcgccaag aagtggcact gtgaggagcc tcacaacctg aatgagttcc ccctgaactt   1140
gccgctcttc ttcctcatca tcaatgcctc tcgacgacac gagctgctcg atacccactct   1200 tggccttttc cgatcctttg ctcccaccaa gactgttaag caggtgcttc tgggctcctt   1260
cactatcatc cccaccaacg atcccgagaa catcaaggcc gttctggcca ctcagttcaa   1320
ggacttctgc ctgggccagc gacacggcca gcttgccccc gttctgggag acggaatctt   1380
cactctggac ggccagggat ggcagcactc tcgagccatg ctgcgacccc agtttgctcg   1440
agaccaggtg tctgacgtcg agatgatcga gcgacacgtg cagatgatgt tgctgcgaat   1500
tcccaacaac aagaagttcg acatccagga gctcttcttc aacctgaccc ttgatactgc   1560
caccgagttt ctgtttggcc agaccgtcgg ctcccagacc gtcgagatgc caacgagga   1620 caagtctacc gtctctgata tgcccaagga tatgcgaaag tctttccagg aggacttta    1680 tgtggcccag caccacggtg gaatccgaac tagattccag atgttctact ggctgtggcg   1740
acccactgag ctcttctctt cctccaagcg agtccacgcc tttgtcgacc actacgtcga   1800
gaaggctctt gccaactccg acgaagagaa gtccgacgac aagtacattt tcctgcgaga   1860
actggcccga gaagtcaagg accccgagt tctgcgagac caggccctca acattctgct   1920
tgctggccga gacaccaccg ccggtgttct gtcctggatc gtctacgagc tggcccgaca   1980
ccccgaggtg tggaagaagc tgcgagccga gattcaccag gactttggtg acggcagcga   2040
tctctcccag atcacctttg agggtcttaa gcgatgcgag tacctgcgat tgtcatcaa    2100 cgagactctg cgactctatc cttctgttcc tcttaacgtc cgatacgcct ctcgagatac   2160
cactcttccc cgaggaggag gacccgacga gtccaagcct atccttgtcc gaaagggaga   2220
caccattgtc tacaacgtct tctctatgca ccgaactgag gagttctggg caaggactg    2280 cgacgagttc cgacctgagc gatgggctga aagggctct cgaggctggg agtacctgcc    2340
cttcaacgga ggaccccgaa tttgcctggg ccagcagtac gctctcactg agacctcgta   2400
cgtcatcact cgaatctgcc agctgttcac caatatcgag aacgctgaca cagctgtcga   2460
gcctcctcag aagctgcacg ccctcactct gtgccatctt aacggtgtgt tcgttaagat   2520
gaccccggac gaggctgcct tgccgagac cgagaagctc attaacgcat aaagggatgt    2580
atacttgtac tgtagatgga ttaataaatt atttatgatg aacaaacatt gactgagaaa   2640
ggcaccatat tgtagcttca agtactgtac tggtagaagt aagcctgtcg ttacccactt   2700
atggagatcc aatattgttt gatgcggcca tcggactgct tggagcgtac agagaattgg   2760
```

-continued

```
taaaatgtgg tggctgggtt ggtttcgatt gaaattatca agatctctga ggtattcttg    2820
gtgttgaagg gatgttcttg gactactgct tgtaacatag atgggatgta gg            2872

<210> SEQ ID NO 2
<211> LENGTH: 1000
<212> TYPE: DNA
<213> ORGANISM: Yarrowia lipolytica

<400> SEQUENCE: 2
gtaatagacg tgcggcgatg cattgagttg ccttagcccc agcttcgaaa tcaagctttc      60
cattcctgag cctgaggaat gggacggagg gggtgaaaat tggggctgga agtcgcttga     120
ataaattctc cgaaatggaa atccaaagac cccaagtgga tttatttttt cgagatttta     180
cagatatttc tcgcagtttt tcacgtcccc ttgtccttgt cctattgttt caaataaact     240
ctcgtctact gatttcacat ggaacctttg ctatttcggg gataaccccc tttgccattg     300
cacgatggac gtggcaaaag aaagatcgcc ctgcggggat acttatcatg tggtcacatg     360
ctgtgattag aaataaagaa aaaggtgctt ttttggcgct gtgattaaca tctcgtctgc     420
cgtgctctac tagtcgcaat agcaaaaact cgcttaatag tgtgcatagt gcggggtagc     480
aggatactga actacagtac gatttgcttg ctactgcttg tagcaattac ctttactgta     540
gggaccacac ctcctggttt caatgtcttt cctcgcctcg acaaagcaaa actgtcaccc     600
aatcacacct tgttcatatt cattagtgca tccgttaacc ttgacatgac acttctcata     660
ctagtgatag ggctgtagtt gagacaagtt gattcacacg gatacataca aagcctcaga     720
gagcaaatgt tatatactca gggaccgacc aatcaaaaaa acacactcct aataaccacc     780
atttccatct acgcgtactc actctgtcag ctgccccaca ttgcccaatg cacaatgcac     840
aatgatgtgt gcaaacaacg caatcaaaag tctatgcatg ctgaccaaac tctgatcacc     900
aagttgcgaa catgaaaaag aagacctgtg tatatataag taaggggag agccctaact     960 agatctttcg aaaacccccc gaccttcacc ttccacaacc                          1000

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
tccaatcgat tctccgaaat ggaaatccaa ag                                   32

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
ctttccatgg tgtaggtgac tctcttgaag atg                                  33

<210> SEQ ID NO 5
<211> LENGTH: 4906
<212> TYPE: DNA
<213> ORGANISM: Artificial Sequence
<220> FEATURE:
<223> OTHER INFORMATION: Plasmid

<400> SEQUENCE: 5
```

-continued

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctca   240
gaattaaccc tcactaaagg gactagtcct gcaggtttaa acgaattcgc cctccatggt   300
gtaggtgact ctcttgaaga tgaggaagga gaccgcaacg gccaaaacgt ataagatgat   360
catggttgtg gaaggtgaag gtcgggggggt tttcgaaaga tctagttagg gctctccccc   420
ttacttatat atacacaggt cttcttttttc atgttcgcaa cttggtgatc agagtttggt   480
cagcatgcat agacttttga ttgcgttgtt tgcacacatc attgtgcatt gtgcattggg   540
caatgtgggg cagctgacag agtgagtacg cgtagatgga aatggtggtt attaggagtg   600 tgttttttttg attggtcggt ccctgagtat ataacatttg ctctctgagg ctttgtatgt   660
atccgtgtga atcaacttgt ctcaactaca gccctatcac tagtatgaga agtgtcatgt   720
caaggttaac ggatgcacta atgaaatatga acaaggtgtg attgggtgac agttttgctt   780
tgtcgaggcg aggaaagaca ttgaaaccag gaggtgtggt ccctacagta aaggtaattg   840
ctacaagcag tagcaagcaa atcgtactgt agttcagtat cctgctaccc cgcactatgc   900
acactattaa gcgagttttt gctattgcga ctagtagagc acggcagacg agatgttaat   960
cacagcgcca aaaagcacc tttttctttta tttctaatca cagcatgtga ccacatgata  1020
agtatccccg cagggcgatc tttctttttgc cacgtccatc gtgcaatggc aaaggggggtt  1080 atccccgaaa tagcaaaggt tccatgtgaa atcagtagac gagagtttat ttgaaacaat  1140
aggacaagga caagggggacg tgaaaaactg cgagaaaatat ctgtaaaatc tcgaaaaaat  1200
aaatccactt ggggtctttg gatttccatt tcggagaatc gattaagggc gaattcgcgg  1260 ccgctaaaatt caattcgccc tatagtgagt cgtattacaa ttcactggcc gtcgttttac  1320
aacgtcgtga ctgggaaaac cctggcgtta cccaacttaa tcgccttgca gcacatcccc  1380
ctttcgccag ctggcgtaat agcgaagagg cccgcaccga tcgcccttcc caacagttgc  1440
gcagcctata cgtacggcag tttaaggttt acacctataa aagagagagc cgttatcgtc  1500
tgtttgtgga tgtacagagt gatattattg acacgccggg cgacggatg gtgatccccc  1560 tggccagtgc acgtctgctg tcagataaag tctcccgtga actttacccg gtggtgcata  1620
tcggggatga aagctggcgc atgatgacca ccgatatggc cagtgtgccg gtctccgtta  1680
tcggggaaga agtggctgat ctcagccacc gcgaaaatga catcaaaaac gccattaacc  1740
tgatgttctg gggaatataaa atgtcaggca tgagattatc aaaaaggatc ttcacctaga  1800
tccttttcac gtagaaagcc agtccgcaga aacggtgctg accccggatg aatgtcagct  1860
actgggctat ctggacaagg gaaaacgcaa gcgcaaagag aaagcaggta gcttgcagtg  1920
ggcttacatg gcgatagcta gactgggcgg ttttatggac agcaagcgaa ccggaattgc  1980
cagctggggc gccctctggt aaggttggga agccctgcaa agtaaactgg atggctttct  2040
tgccgccaag gatctgatgg cgcaggggat caagctctga tcaagagaca ggatgaggat  2100
cgtttcgcat gattgaacaa gatggattgc acgcaggttc tccggccgct tgggtggaga  2160
ggctattcgg ctatgactgg gcacaacaga caatcggctg ctctgatgcc gccgtgttcc  2220
ggctgtcagc gcaggggcgc ccggttcttt ttgtcaagac cgacctgtcc ggtgccctga  2280
atgaactgca agacgaggca gcgcggctat cgtggctggc cacgacgggc gttccttgcg  2340
cagctgtgct cgacgttgtc actgaagcgg gaagggactg gctgctattg ggcgaagtgc  2400
```

```
cggggcagga tctcctgtca tctcaccttg ctcctgccga gaaagtatcc atcatggctg   2460
atgcaatgcg gcggctgcat acgcttgatc cggctacctg cccattcgac caccaagcga   2520
aacatcgcat cgagcgagca cgtactcgga tggaagccgg tcttgtcgat caggatgatc   2580
tggacgaaga gcatcagggg ctcgcgccag ccgaactgtt cgccaggctc aaggcgagca   2640
tgcccgacgg cgaggatctc gtcgtgaccc atggcgatgc ctgcttgccg aatatcatgg   2700
tggaaaatgg ccgcttttct ggattcatcg actgtggccg gctgggtgtg gcggaccgct   2760
atcaggacat agcgttggct acccgtgata ttgctgaaga gcttggcggc gaatgggctg   2820
accgcttcct cgtgctttac ggtatcgccg ctcccgattc gcagcgcatc gccttctatc   2880
gccttcttga cgagttcttc tgaattatta acgcttacaa tttcctgatg cggtattttc   2940
tccttacgca tctgtgcggt atttcacacc gcatcaggtg cacttttcg gggaaatgtg   3000 cgcggaaccc ctatttgttt attttttctaa atacattcaa atatgtatcc gctcatgaga   3060
ttatcaaaaa ggatcttcac ctagatcctt ttaaattaaa aatgaagttt taaatcaatc   3120
taaagtatat atgagtaaac ttggtctgac agttaccaat gcttaatcag tgaggcacct   3180
atctcagcga tctgtctatt tcgttcatcc atagttgcct gactccccgt cgtgtagata   3240
actacgatac gggagggctt accatctggc cccagtgctg caatgatacc gcgagaccca   3300
cgctcaccgg ctccagattt atcagcaata aaccagccag ccggaagggc cgagcgcaga   3360
agtggtcctg caactttatc cgcctccatc cagtctatta attgttgccg ggaagctaga   3420
gtaagtagtt cgccagttaa tagtttgcgc aacgttgttg ccattgctac aggcatcgtg   3480
gtgtcacgct cgtcgtttgg tatggcttca ttcagctccg gttcccaacg atcaaggcga   3540
gttacatgat cccccatgtt gtgcaaaaaa gcggttagct ccttcggtcc tccgatcgtt   3600
gtcagaagta agttggccgc agtgttatca ctcatggtta tggcagcact gcataattct   3660
cttactgtca tgccatccgt aagatgcttt tctgtgactg gtgagtactc aaccaagtca   3720
ttctgagaat agtgtatgcg gcgaccgagt tgctcttgcc cggcgtcaat acgggataat   3780
accgcgccac atagcagaac tttaaaagtg ctcatcattg gaaaacgttc ttcggggcga   3840
aaactctcaa ggatcttacc gctgttgaga tccagttcga tgtaacccac tcgtgcaccc   3900
aactgatctt cagcatcttt tactttcacc agcgtttctg ggtgagcaaa acaggaagg   3960 caaaatgccg caaaaaaggg aataagggcg acacggaaat gttgaatact catactcttc   4020 cttttcaat attattgaag catttatcag ggttattgtc tcatgaccaa atcccttaa   4080 cgtgagtttt cgttccactg agcgtcagac cccgtagaaa agatcaaagg atcttcttga   4140
gatccttttt ttctgcgcgt aatctgctgc ttgcaaacaa aaaaaccacc gctaccagcg   4200
gtggtttgtt tgccggatca agagctacca actctttttc cgaaggtaac tggcttcagc   4260
agagcgcaga taccaaatac tgttcttcta gtgtagccgt agttaggcca ccacttcaag   4320
aactctgtag caccgcctac atacctcgct ctgctaatcc tgttaccagt ggctgctgcc   4380
agtggcgata gtcgtgtct taccggggtg gactcaagac gatagttacc ggataaggcg   4440
cagcggtcgg gctgaacggg gggttcgtgc acacagccca gcttggagcg aacgacctac   4500
accgaactga gatacctaca gcgtgagcta tgagaaagcg ccacgcttcc cgaagggaga   4560
aaggcggaca ggtatccggt aagcggcagg gtcggaacag gagagcgcac gagggagctt   4620
ccagggggaa acgcctggta tctttatagt cctgtcgggt ttcgccacct ctgacttgag   4680
cgtcgatttt tgtgatgctc gtcagggggg cggagcctat ggaaaaacgc cagcaacgcg   4740
gcctttttac ggttcctggc cttttgctgg ccttttgctc acatgttctt tcctgcgtta   4800
```

```
tcccctgatt ctgtggataa ccgtattacc gcctttgagt gagctgatac cgctcgccgc   4860
agccgaacga ccgagcgcag cgagtcagtg agcgaggaag cggaag              4906

<210> SEQ ID NO 6
<211> LENGTH: 942
<212> TYPE: DNA
<213> ORGANISM: Yarrowia lipolytica

<400> SEQUENCE: 6
attctccgaa atggaaatcc aaagacccca agtggattta ttttttcgag attttacaga     60
tatttctcgc agttttcac gtccccttgt ccttgtccta ttgtttcaaa taaactctcg    120
tctactgatt tcacatggaa cctttgctat ttcggggata accccctttg ccattgcacg   180
atggacgtgg caaagaaag atcgccctgc ggggatactt atcatgtggt cacatgctgt    240
gattagaaat aaagaaaaag gtgctttttt ggcgctgtga ttaacatctc gtctgccgtg   300
ctctactagt cgcaatagca aaaactcgct taatagtgtg catagtgcgg ggtagcagga   360
tactgaacta cagtacgatt tgcttgctac tgcttgtagc aattaccttt actgtaggga   420
ccacacctcc tggtttcaat gtcttttcctc gcctcgacaa agcaaaactg tcacccaatc   480
acaccttgtt catattcatt agtgcatccg ttaaccttga catgacactt ctcatactag   540
tgatagggct gtagttgaga caagttgatt cacacggata catacaaagc ctcagagagc   600
aaatgttata tactcaggga ccgaccaatc aaaaaaacac actcctaata accaccattt   660
ccatctacgc gtactcactc tgtcagctgc cccacattgc ccaatgcaca atgcacaatg   720
atgtgtgcaa acaacgcaat caaaagtcta tgcatgctga ccaaactctg atcaccaagt   780
tgcgaacatg aaaaagaaga cctgtgtata taagtaag ggggagagcc ctaactagat      840
ctttcgaaaa ccccccgacc ttccacttcc acaaccatga tcatcttata cgttttggcc    900
gttgcggtct ccttcctcat cttcaagaga gtcacctaca cc                      942

<210> SEQ ID NO 7
<211> LENGTH: 876
<212> TYPE: DNA
<213> ORGANISM: Yarrowia lipolytica

<400> SEQUENCE: 7
attctccgaa atggaaatcc aaagacccca agtggattta ttttttcgag attttacaga     60
tatttctcgc agttttcac gtccccttgt ccttgtccta ttgtttcaaa taaactctcg    120
tctactgatt tcacatggaa cctttgctat ttcggggata accccctttg ccattgcacg   180
atggacgtgg caaagaaag atcgccctgc ggggatactt atcatgtggt cacatgctgt    240
gattagaaat aaagaaaaag gtgctttttt ggcgctgtga ttaacatctc gtctgccgtg   300
ctctactagt cgcaatagca aaaactcgct taatagtgtg catagtgcgg ggtagcagga   360
tactgaacta cagtacgatt tgcttgctac tgcttgtagc aattaccttt actgtaggga   420
ccacacctcc tggtttcaat gtcttttcctc gcctcgacaa agcaaaactg tcacccaatc   480
acaccttgtt catattcatt agtgcatccg ttaaccttga catgacactt ctcatactag   540
tgatagggct gtagttgaga caagttgatt cacacggata catacaaagc ctcagagagc   600
aaatgttata tactcaggga ccgaccaatc aaaaaaacac actcctaata accaccattt   660
ccatctacgc gtactcactc tgtcagctgc cccacattgc ccaatgcaca atgcacaatg   720
atgtgtgcaa acaacgcaat caaaagtcta tgcatgctga ccaaactctg atcaccaagt   780
tgcgaacatg aaaaagaaga cctgtgtata taagtaag ggggagagcc ctaactagat      840
```

| | | |
|---|---|---|
| ctttcgaaaa ccccccgacc ttcaccttcc acaacc | | 876 |

<210> SEQ ID NO 8
<211> LENGTH: 4906
<212> TYPE: DNA
<213> ORGANISM: Artificial Sequence
<220> FEATURE:
<223> OTHER INFORMATION: Plasmid

<400> SEQUENCE: 8

| | | |
|---|---|---|
| agcgcccaat acgcaaaccg cctctccccg cgcgttggcc gattcattaa tgcagctggc | | 60 |
| acgacaggtt tcccgactgg aaagcgggca gtgagcgcaa cgcaattaat gtgagttagc | | 120 |
| tcactcatta ggcaccccag gctttacact ttatgcttcc ggctcgtatg ttgtgtggaa | | 180 |
| ttgtgagcgg ataacaattt cacacaggaa acagctatga ccatgattac gccaagctca | | 240 |
| gaattaaccc tcactaaagg gactagtcct gcaggtttaa cgaattcgc cctccatggt | | 300 |
| gtaggtgact ctcttgaaga tgaggaagga gaccgcaacg gccaaaacgt ataagatgat | | 360 |
| catggttgtg gaaggtgaag gtcgggggt tttcgaaaga tctagttagg gctctccccc | | 420 |
| ttacttatat atacacaggt cttctttttc atgttcgcaa cttggtgatc agagtttggt | | 480 |
| cagcatccat agacttttga ttgcgttgtt tgcacacatc attgtgcatt gtgcattggg | | 540 |
| caatgtgggg cagctgacag agtgagtacg cgtagatgga aatggtggtt attaggagtg | | 600 |
| tgtttttttg attggtcggt ccctgagtat ataacatttg ctctctgagg ctttgtatgt | | 660 |
| atccgtgtga atcaacttgt ctcaactaca gccctatcac tagtatgaga agtgtcatgt | | 720 |
| caaggttaac ggatgcacta atgaatatga acaaggtgtg attgggtgac agttttgctt | | 780 |
| tgtcgaggcg aggaaagaca ttgaaaccag gaggtgtggt ccctacagta aaggtaattg | | 840 |
| ctacaagcag tagcaagcaa atcgtactgt agttcagtat cctgctaccc cgcactatgc | | 900 |
| acactattaa gcgagttttt gctattgcga ctagtagagc acggcagacg agatgttaat | | 960 |
| cacagcgcca aaaagcacc tttttcttta tttctaatca cagcatgtga ccacatgata | | 1020 |
| agtatccccg cagggcgatc tttcttttgc cacgtccatc gtgcaatggc aaaggggtt | | 1080 |
| atccccgaaa tagcaaaggt tccatgtgaa atcagtagac gagagtttat ttgaaacaat | | 1140 |
| aggacaagga caagggacg tgaaaaactg cgagaaatat ctgtaaaatc tcgaaaaaat | | 1200 |
| aaatccactt ggggtctttg gatttccatt tcggagaatc gattaagggc gaattcgcgg | | 1260 |
| ccgctaaatt caattcgccc tatagtgagt cgtattacaa ttcactggcc gtcgttttac | | 1320 |
| aacgtcgtga ctgggaaaac cctggcgtta cccaacttaa tcgccttgca gcacatcccc | | 1380 |
| ctttcgccag ctggcgtaat agcgaagagg cccgcaccga tcgcccttcc caacagttgc | | 1440 |
| gcagcctata cgtacggcag tttaaggttt acacctataa aagagagagc cgttatcgtc | | 1500 |
| tgtttgtgga tgtacagagt gatattattg acacgccggg cgacggatg gtgatccccc | | 1560 |
| tggccagtgc acgtctgctg tcagataaag tctcccgtga actttacccg gtggtgcata | | 1620 |
| tcggggatga agctggcgc atgatgacca ccgatatggc cagtgtgccg gtctccgtta | | 1680 |
| tcggggaaga agtggctgat ctcagccacc gcgaaaatga catcaaaaac gccattaacc | | 1740 |
| tgatgttctg gggaatataa atgtcaggca tgagattatc aaaaaggatc ttcacctaga | | 1800 |
| tccttttcac gtagaaagcc agtccgcaga aacggtgctg accccggatg aatgtcagct | | 1860 |
| actgggctat ctggacaagg gaaaacgcaa gcgcaaagag aaagcaggta gcttgcagtg | | 1920 |
| ggcttacatg gcgatagcta gactgggcgg ttttatggac agcaagcgaa ccggaattgc | | 1980 |
| cagctggggc gccctctggt aaggttggga agccctgcaa agtaaactgg atggctttct | | 2040 |

-continued

```
tgccgccaag gatctgatgg cgcaggggat caagctctga tcaagagaca ggatgaggat    2100
cgtttcgcat gattgaacaa gatggattgc acgcaggttc tccggccgct tgggtggaga    2160
ggctattcgg ctatgactgg gcacaacaga caatcggctg ctctgatgcc gccgtgttcc    2220
ggctgtcagc gcaggggcgc ccggttcttt ttgtcaagac cgacctgtcc ggtgccctga    2280
atgaactgca agacgaggca gcgcggctat cgtggctggc cacgacgggc gttccttgcg    2340
cagctgtgct cgacgttgtc actgaagcgg gaagggactg gctgctattg ggcgaagtgc    2400
cggggcagga tctcctgtca tctcaccttg ctcctgccga aaagtatcc atcatggctg     2460
atgcaatgcg gcggctgcat acgcttgatc cggctacctg cccattcgac caccaagcga    2520
aacatcgcat cgagcgagca cgtactcgga tggaagccgg tcttgtcgat caggatgatc    2580
tggacgaaga gcatcagggg ctcgcgccag ccgaactgtt cgccaggctc aaggcgagca    2640
tgcccgacgg cgaggatctc gtcgtgaccc atggcgatgc ctgcttgccg aatatcatgg    2700
tggaaaatgg ccgcttttct ggattcatcg actgtggccg ctgggtgtg gcggaccgct     2760
atcaggacat agcgttggct acccgtgata ttgctgaaga gcttggcggc gaatgggctg    2820
accgcttcct cgtgctttac ggtatcgccg ctcccgattc gcagcgcatc gccttctatc    2880
gccttcttga cgagttcttc tgaattatta cgcttacaa tttcctgatg cggtattttc     2940
tccttacgca tctgtgcggt atttcacacc gcatcaggtg gcacttttcg gggaaatgtg    3000
cgcggaaccc ctatttgttt attttttctaa atacattcaa atatgtatcc gctcatgaga   3060
ttatcaaaaa ggatcttcac ctagatcctt taaattaaa aatgaagttt taaatcaatc     3120
taaagtatat atgagtaaac ttggtctgac agttaccaat gcttaatcag tgaggcacct    3180
atctcagcga tctgtctatt tcgttcatcc atagttgcct gactccccgt cgtgtagata    3240
actacgatac gggagggctt accatctggc cccagtgctg caatgatacc gcgagaccca    3300
cgctcaccgg ctccagattt atcagcaata aaccagccag ccggaagggc cgagcgcaga    3360
agtggtcctg caactttatc cgcctccatc cagtctatta attgttgccg gaagctaga    3420
gtaagtagtt cgccagttaa tagtttgcgc aacgttgttg ccattgctac aggcatcgtg    3480
gtgtcacgct cgtcgtttgg tatggcttca ttcagctccg gttcccaacg atcaaggcga   3540
gttacatgat cccccatgtt gtgcaaaaaa gcggttagct ccttcggtcc tccgatcgtt   3600
gtcagaagta agttggccgc agtgttatca ctcatggtta tggcagcact gcataattct    3660
cttactgtca tgccatccgt aagatgcttt tctgtgactg gtgagtactc aaccaagtca    3720
ttctgagaat agtgtatgcg gcgaccgagt tgctcttgcc cggcgtcaat acgggataat    3780
accgcgccac atagcagaac tttaaaagtg ctcatcattg gaaaacgttc ttcggggcga    3840
aaactctcaa ggatcttacc gctgttgaga tccagttcga tgtaacccac tcgtgcaccc    3900
aactgatctt cagcatcttt tactttcacc agcgtttctg ggtgagcaaa aacaggaagg    3960
caaaatgccg caaaaaaggg aataagggcg acacggaaat gttgaatact catactcttc    4020
cttttcaat attattgaag catttatcag ggttattgtc tcatgaccaa aatcccttaa     4080
cgtgagtttt cgttccactg agcgtcagac cccgtagaaa agatcaaagg atcttcttga    4140
gatcctttt tctgcgcgt aatctgctgc ttgcaaacaa aaaaaccacc gctaccagcg       4200
gtggtttgtt tgccggatca agagctacca actctttttc cgaaggtaac tggcttcagc    4260
agagcgcaga taccaaatac tgttcttcta gtgtagccgt agttaggcca ccacttcaag    4320
aactctgtag caccgcctac atacctcgct ctgctaatcc tgttaccagt ggctgctgcc    4380
agtggcgata agtcgtgtct taccgggttg gactcaagac gatagttacc ggataaggcg    4440
```

-continued

```
cagcggtcgg gctgaacggg gggttcgtgc acacagccca gcttggagcg aacgacctac    4500
accgaactga gatacctaca gcgtgagcta tgagaaagcg ccacgcttcc cgaagggaga    4560
aaggcggaca ggtatccggt aagcggcagg gtcggaacag gagagcgcac gagggagctt    4620 ccaggggaa  acgcctggta tctttatagt cctgtcgggt ttcgccacct ctgacttgag    4680
cgtcgatttt tgtgatgctc gtcaggggg  cggagcctat ggaaaaacgc cagcaacgcg    4740
gcctttttac ggttcctggc cttttgctgg ccttttgctc acatgttctt tcctgcgtta    4800 tccctgatt  ctgtggataa ccgtattacc gcctttgagt gagctgatac cgctcgccgc    4860
agccgaacga ccgagcgcag cgagtcagtg agcgaggaag cggaag                   4906
```

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9

```
atcaaaagtc tatgcatcct gaccaaactc tgatc                                 35
```

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10

```
gatcagagtt tggtcaggat gcatagactt ttgat                                 35
```

<210> SEQ ID NO 11
<211> LENGTH: 876
<212> TYPE: DNA
<213> ORGANISM: Yarrowia lipolytica

<400> SEQUENCE: 11

```
attctccgaa atggaaatcc aaagacccca agtggattta ttttttcgag attttacaga     60
tatttctcgc agttttttcac gtccccttgt ccttgtccta ttgtttcaaa taaactctcg    120
tctactgatt tcacatggaa cctttgctat ttcggggata accccctttg ccattgcacg    180
atggacgtgg caaaagaaag atcgccctgc ggggatactt atcatgtggt cacatgctgt    240
gattagaaat aaagaaaaag gtgctttttt ggcgctgtga ttaacatctc gtctgccgtg    300
ctctactagt cgcaatagca aaaactcgct taatagtgtg catagtgcgg ggtagcagga    360
tactgaacta cagtacgatt tgcttgctac tgcttgtagc aattacccttt actgtaggga    420 ccacacctcc tggtttcaat gtctttcctc gcctcgacaa agcaaaactg tcacccaatc    480
acaccttgtt catattcatt agtgcatccg ttaaccttga catgacactt tcatactag     540 tgatagggct gtagttgaga caagttgatt cacacggata catacaaagc ctcagagagc    600
aaatgttata tactcaggga ccgaccaatc aaaaaaacac actcctaata accaccattt    660
ccatctacgc gtactcactc tgtcagctgc cccacattgc ccaatgcaca atgcacaatg    720
atgtgtgcaa acaacgcaat caaaagtcta tggatgctga ccaaactctg atcaccaagt    780
tgcgaacatg aaaaagaaga cctgtgtata tataagtaag ggggagagcc ctaactagat    840 cttttcgaaaa ccccccgacc ttcaccttcc acaacc                             876
```

<210> SEQ ID NO 12
<211> LENGTH: 4906
<212> TYPE: DNA
<213> ORGANISM: Artificial Sequence
<220> FEATURE:
<223> OTHER INFORMATION: Plasmid

<400> SEQUENCE: 12

| | | | | | |
|---|---|---|---|---|---|
| agcgcccaat | acgcaaaccg | cctctccccg | cgcgttggcc | gattcattaa tgcagctggc | 60 |
| acgacaggtt | tcccgactgg | aaagcgggca | gtgagcgcaa | cgcaattaat gtgagttagc | 120 |
| tcactcatta | ggcaccccag | gctttacact | ttatgcttcc | ggctcgtatg ttgtgtggaa | 180 |
| ttgtgagcgg | ataacaattt | cacacaggaa | acagctatga | ccatgattac gccaagctca | 240 |
| gaattaaccc | tcactaaagg | gactagtcct | gcaggtttaa | acgaattcgc cctccatggt | 300 |
| gtaggtgact | ctcttgaaga | tgaggaagga | gaccgcaacg | gccaaaacgt ataagatgat | 360 |
| catggttgtg | gaaggtgaag | gtcgggggt | tttcgaaaga | tctagttagg gctctccccc | 420 |
| ttacttatat | atacacaggt | cttcttttc | atgttcgcaa | cttggtgatc agagtttggt | 480 |
| cagcatccat | agacttttga | ttgcgttgtt | tgcacacatc | attgtgcatt gtgcattggg | 540 |
| caatgtgggg | cagctgacag | agtgagtacg | cgtagatgga | aatggtggtt attaggagtg | 600 |
| tgtttttttg | attggtcggt | ccctgagtat | ataacatttg | ctctctgagg ctttgtatgt | 660 |
| atccgtgtga | atcaacttgt | ctcaactaca | gccctatcac | tagtatgaga agtgtcatgt | 720 |
| caaggttaac | ggatgcacta | atgaatatga | acaaggtgtg | attgggtgac agttttgctt | 780 |
| tgtcgaggcg | aggaaagaca | ttgaaaccag | gaggtgtggt | ccctacagta aaggtaattg | 840 |
| ctacaagcag | tagcaagcaa | atcgtactgt | agttcagtat | cctgctaccc cgcactatgc | 900 |
| acactattaa | gcgagttttt | gctattgcga | ctagtagagc | acggcagacg agatgttaat | 960 |
| cacagcgcca | aaaagcacc | tttttcttta | tttctaatca | cagcatgtga ccacatgata | 1020 |
| agtatccccg | cagggcgatc | ttctttttgc | cacgtccatc | gtgcaatggc aaaggggtt | 1080 |
| atccccgaaa | tagcaaaggt | tccatgtgaa | atcagtagac | gagagtttat tgaaacaat | 1140 |
| aggacaagga | caaggggacg | tgaaaaactg | cgagaaatat | ctgtaaaatc tcgaaaattt | 1200 |
| aaatccactt | ggggtctttg | gatttccatt | tcggagaatc | gattaagggc gaattcgcgg | 1260 |
| ccgctaaatt | caattcgccc | tatagtgagt | cgtattacaa | ttcactggcc gtcgttttac | 1320 |
| aacgtcgtga | ctgggaaaac | cctggcgtta | cccaacttaa | tcgccttgca gcacatcccc | 1380 |
| ctttcgccag | ctggcgtaat | agcgaagagg | cccgcaccga | tcgcccttcc caacagttgc | 1440 |
| gcagcctata | cgtacggcag | tttaaggttt | acacctataa | aagagagagc cgttatcgtc | 1500 |
| tgtttgtgga | tgtacagagt | gatattattg | acacgccggg | cgacggatg gtgatccccc | 1560 |
| tggccagtgc | acgtctgctg | tcagataaag | tctcccgtga | actttacccg gtggtgcata | 1620 |
| tcggggatga | agctggcgc | atgatgacca | ccgatatggc | cagtgtgccg gtctccgtta | 1680 |
| tcggggaaga | agtggctgat | ctcagccacc | gcgaaaatga | catcaaaaac gccattaacc | 1740 |
| tgatgttctg | gggaatataa | atgtcaggca | tgagattatc | aaaaaggatc ttcacctaga | 1800 |
| tccttttcac | gtagaaagcc | agtccgcaga | aacggtgctg | accccggatg aatgtcagct | 1860 |
| actgggctat | ctggacaagg | gaaaacgcaa | gcgcaaagag | aaagcaggta gcttgcagtg | 1920 |
| ggcttacatg | gcgatagcta | gactgggcgg | ttttatggac | agcaagcgaa ccggaattgc | 1980 |
| cagctggggc | gccctctggt | aaggttggga | agccctgcaa | agtaaactgg atggctttct | 2040 |
| tgccgccaag | gatctgatgg | cgcaggggat | caagctctga | tcaagagaca ggatgaggat | 2100 |
| cgtttcgcat | gattgaacaa | gatggattgc | acgcaggttc | tccggccgct tgggtggaga | 2160 |

```
ggctattcgg ctatgactgg gcacaacaga caatcggctg ctctgatgcc gccgtgttcc    2220
ggctgtcagc gcaggggcgc ccggttcttt ttgtcaagac cgacctgtcc ggtgccctga    2280
atgaactgca agacgaggca gcgcggctat cgtggctggc cacgacgggc gttccttgcg    2340
cagctgtgct cgacgttgtc actgaagcgg aagggactg gctgctattg ggcgaagtgc     2400
cggggcagga tctcctgtca tctcaccttg ctcctgccga aaagtatcc atcatggctg     2460 atgcaatgcg gcggctgcat acgcttgatc cggctacctg cccattcgac caccaagcga    2520
aacatcgcat cgagcgagca cgtactcgga tggaagccgg tcttgtcgat caggatgatc    2580
tggacgaaga gcatcagggg ctcgcgccag ccgaactgtt cgccaggctc aaggcgagca    2640
tgcccgacgg cgaggatctc gtcgtgaccc atggcgatgc ctgcttgccg aatatcatgg    2700
tggaaaatgg ccgcttttct ggattcatcg actgtggccg gctgggtgtg gcggaccgct    2760
atcaggacat agcgttggct acccgtgata ttgctgaaga gcttggcggc gaatgggctg    2820
accgcttcct cgtgctttac ggtatcgccg ctcccgattc gcagcgcatc gccttctatc    2880
gccttcttga cgagttcttc tgaattatta cgcttacaa tttcctgatg cggtattttc     2940
tccttacgca tctgtgcggt atttcacacc gcatcaggtg gcacttttcg gggaaatgtg    3000
cgcggaaccc ctatttgttt atttttctaa atacattcaa atatgtatcc gctcatgaga    3060
ttatcaaaaa ggatcttcac ctagatcctt taaattaaa aatgaagttt taaatcaatc     3120
taaagtatat atgagtaaac ttggtctgac agttaccaat gcttaatcag tgaggcacct    3180
atctcagcga tctgtctatt tcgttcatcc atagttgcct gactccccgt cgtgtagata    3240
actacgatac gggagggctt accatctggc cccagtgctg caatgatacc gcgagaccca    3300
cgctcaccgg ctccagattt atcagcaata aaccagccag ccggaagggc cgagcgcaga    3360
agtggtcctg caactttatc cgcctccatc cagtctatta attgttgccg ggaagctaga    3420
gtaagtagtt cgccagttaa tagtttgcgc aacgttgttg ccattgctac aggcatcgtg    3480
gtgtcacgct cgtcgtttgg tatggcttca ttcagctccg gttcccaacg atcaaggcga    3540
gttacatgat cccccatgtt gtgcaaaaaa gcggttagct ccttcggtcc tccgatcgtt    3600
gtcagaagta agttggccgc agtgttatca ctcatggtta tggcagcact gcataattct    3660
cttactgtca tgccatccgt aagatgcttt tctgtgactg gtgagtactc aaccaagtca    3720
ttctgagaat agtgtatgcg gcgaccgagt tgctcttgcc cggcgtcaat acgggataat    3780
accgcgccac atagcagaac tttaaaagtg ctcatcattg gaaaacgttc ttcggggcga    3840
aaactctcaa ggatcttacc gctgttgaga tccagttcga tgtaacccac tcgtgcaccc    3900
aactgatctt cagcatcttt tactttcacc agcgtttctg ggtgagcaaa aacaggaagg    3960
caaaatgccg caaaaaaggg aataagggcg acacggaaat gttgaatact catactcttc    4020 cttttcaat attattgaag catttatcag ggttattgtc tcatgaccaa aatcccttaa     4080
cgtgagtttt cgttccactg agcgtcagac cccgtagaaa agatcaaagg atcttcttga    4140
gatccttttt ttctgcgcgt aatctgctgc ttgcaaacaa aaaaaccacc gctaccagcg    4200
gtggtttgtt tgccggatca agagctacca actcttttc cgaaggtaac tggcttcagc     4260
agagcgcaga taccaaatac tgttcttcta gtgtagccgt agttaggcca ccacttcaag    4320
aactctgtag caccgcctac atacctcgct ctgctaatcc tgttaccagt ggctgctgcc    4380
agtggcgata gtcgtgtct taccggggttg gactcaagac gatagttacc ggataaggcg     4440
cagcggtcgg gctgaacggg gggttcgtgc acacagccca gcttggagcg aacgacctac    4500
accgaactga gatacctaca gcgtgagcta tgagaaagcg ccacgcttcc cgaagggaga    4560
```

```
aaggcggaca ggtatccggt aagcggcagg gtcggaacag gagagcgcac gagggagctt    4620 ccaggggaa acgcctggta tctttatagt cctgtcgggt ttcgccacct ctgacttgag     4680
cgtcgatttt tgtgatgctc gtcagggggg cggagcctat ggaaaaacgc cagcaacgcg    4740 gccttttttac ggttcctggc cttttgctgg ccttttgctc acatgttctt tcctgcgtta   4800
tcccctgatt ctgtggataa ccgtattacc gcctttgagt gagctgatac cgctcgccgc    4860
agccgaacga ccgagcgcag cgagtcagtg agcgaggaag cggaag                   4906

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
gaccccaagt ggatttaaat tttcgagatt ttacag                               36

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
ctgtaaaatc tcgaaaattt aaatccactt ggggtc                               36

<210> SEQ ID NO 15
<211> LENGTH: 834
<212> TYPE: DNA
<213> ORGANISM: Yarrowia lipolytica

<400> SEQUENCE: 15
ttttcgagat tttacagata tttctcgcag tttttcacgt cccccttgtcc ttgtcctatt    60 gtttcaaata aactctcgtc tactgatttc acatggaacc tttgctattt cggggataac    120
cccctttgcc attgcacgat ggacgtggca aagaaagat cgccctgcgg ggatacttat     180
catgtggtca catgctgtga ttagaaataa agaaaaaggt gcttttttgg cgctgtgatt    240
aacatctcgt ctgccgtgct ctactagtcg caatagcaaa aactcgctta atagtgtgca    300
tagtgcgggg tagcaggata ctgaactaca gtacgatttg cttgctactg cttgtagcaa    360 ttaccttttac tgtagggacc acacctcctg gtttcaatgt ctttcctcgc ctcgacaaag    420
caaaactgtc acccaatcac accttgttca tattcattag tgcatccgtt aaccttgaca    480
tgacacttct catactagtg atagggctgt agttgagaca agttgattca cacggataca    540
tacaaagcct cagagagcaa atgttatata ctcaggacc gaccaatcaa aaaacacac      600 tcctaataac caccatttcc atctacgcgt actcactctg tcagctgccc cacattgccc    660
aatgcacaat gcacaatgat gtgtgcaaac aacgcaatca aaagtctatg gatgctgacc    720
aaactctgat caccaagttg cgaacatgaa aaagaagacc tgtgtatata taagtaaggg   780
ggagagccct aactagatct ttcgaaaacc ccccgacctt caccttccac aacc          834

<210> SEQ ID NO 16
<211> LENGTH: 4909
<212> TYPE: DNA
<213> ORGANISM: Artificial Sequence
<220> FEATURE:
<223> OTHER INFORMATION: Plasmid
```

<400> SEQUENCE: 16

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctca   240
gaattaaccc tcactaaagg actagtcct gcaggtttaa acgaattcgc cctccatggt   300
gtaggtgact ctcttgaaga tgaggaagga gaccgcaacg gccaaaacgt ataagatgat   360
catggttgtg gaaggtgaag gtcgggggt tttcgaaaga tctagttagg gctctccccc    420
ttacttatat atacacaggt cttcttttc atgttcgcaa cttggtgatc agagtttggt    480
cagcatccat agacttttga ttgcgttgtt tgcacacatc attgtgcatt gtgcattggg   540
caatgtgggg cagctgacag agtgagtacg cgtagatgga aatggtggtt attaggagtg   600
tgttttttg attggtcggt ccctgagtat ataacatttg ctctctgagg ctttgtatgt   660
atccgtgtga atcaacttgt ctcaactaca gccctatcac tagtatgaga agtgtcatgt   720
caaggttaac ggatgcacta atgaatatga acaaggtgtg attgggtgac agttttgctt   780
tgtcgaggcg aggaaagaca ttgaaaccag gaggtgtggt ccctacagta aaggtaattg   840
ctacaagcag tagcaagcaa atcgtactgt agttcagtat cctgctaccc cgcactatgc   900
acactattaa gcgagttttt gctattgcga ctagtagagc acggcagacg agatgttaat   960
cacagcgcca aaaagcacc ttttctttta tttctaatca cagcatgtga ccacatgata   1020
agtatccccg cagggcgatc tttcttttgc cacgtccatc gtgcaatggc aaggggggtt   1080
atccccgaaa tagcaaaggt tccatgtgaa atcagtagac gagagtttat cgattgaaac   1140
aataggacaa ggacaagggg acgtgaaaaa ctgcgagaaa tatctgtaaa atctcgaaaa   1200
aataaatcca cttggggtct ttggatttcc atttcggaga atcgattaag ggcgaattcg   1260
cggccgctaa attcaattcg ccctatagtg agtcgtatta caattcactg gccgtcgttt   1320
tacaacgtcg tgactgggaa aaccctggcg ttacccaact taatcgcctt gcagcacatc   1380
cccctttcgc cagctggcgt aatagcgaag aggcccgcac cgatcgccct tcccaacagt   1440
tgcgcagcct atacgtacgg cagtttaagg tttacaccta aaaagagag agccgttatc   1500
gtctgtttgt ggatgtacag agtgatatta ttgacacgcc ggggcgacgg atggtgatcc   1560
ccctggccag tgcacgtctg ctgtcagata aagtctcccg tgaactttac ccggtggtgc   1620
atatcgggga tgaaagctgg cgcatgatga ccaccgatat ggccagtgtg ccggtctccg   1680
ttatcgggga agaagtggct gatctcagcc accgcgaaaa tgacatcaaa aacgccatta   1740
acctgatgtt ctggggaata taaatgtcag gcatgagatt atcaaaaagg atcttcacct   1800
agatcctttt cacgtagaaa gccagtccgc agaaacggtg ctgacccgg atgaatgtca    1860
gctactgggc tatctggaca agggaaaacg caagcgcaaa gagaaagcag gtagcttgca   1920
gtgggcttac atggcgatag ctagactggg cggttttatg gacagcaagc gaaccggaat   1980
tgccagctgg ggcgccctct ggtaaggttg ggaagccctg caaagtaaac tggatggctt   2040
tcttgccgcc aaggatctga tggcgcaggg gatcaagctc tgatcaagag acaggatgag   2100
gatcgtttcg catgattgaa caagatggat tgcacgcagg ttctccggcc gcttgggtgg   2160
agaggctatt cggctatgac tgggcacaac agacaatcgg ctgctctgat gccgccgtgt   2220
tccggctgtc agcgcagggg cgcccggttc ttttgtcaa gaccgacctg tccggtgccc    2280
tgaatgaact gcaagacgag gcagcgcggc tatcgtggct ggccacgacg ggcgttcctt   2340
```

```
gcgcagctgt gctcgacgtt gtcactgaag cgggaaggga ctggctgcta ttgggcgaag    2400
tgccggggca ggatctcctg tcatctcacc ttgctcctgc cgagaaagta tccatcatgg    2460
ctgatgcaat gcggcggctg catacgcttg atccggctac ctgcccattc gaccaccaag    2520
cgaaacatcg catcgagcga gcacgtactc ggatggaagc cggtcttgtc gatcaggatg    2580
atctggacga agagcatcag gggctcgcgc cagccgaact gttcgccagg ctcaaggcga    2640
gcatgcccga cggcgaggat ctcgtcgtga cccatggcga tgcctgcttg ccgaatatca    2700
tggtggaaaa tggccgcttt tctggattca tcgactgtgg ccggctgggt gtggcggacc    2760
gctatcagga catagcgttg gctacccgtg atattgctga gagcttggc ggcgaatggg    2820 ctgaccgctt cctcgtgctt tacggtatcg ccgctcccga ttcgcagcgc atcgccttct    2880
atcgccttct tgacgagttc ttctgaatta ttaacgctta caatttcctg atgcggtatt    2940
ttctccttac gcatctgtgc ggtatttcac accgcatcag gtggcacttt cggggaaat    3000 gtgcgcggaa cccctatttg tttattttc taaatacatt caaatatgta tccgctcatg    3060
agattatcaa aaggatcttc acctagatcc ttttaaatt aaaaatgaag ttttaaatca    3120
atctaaagta tatatgagta aacttggtct gacagttacc aatgcttaat cagtgaggca    3180
cctatctcag cgatctgtct atttcgttca tccatagttg cctgactccc cgtcgtgtag    3240
ataactacga tacgggaggg cttaccatct ggccccagtg ctgcaatgat accgcgagac    3300
ccacgctcac cggctccaga tttatcagca ataaccagc cagccggaag ggccgagcgc    3360
agaagtggtc ctgcaacttt atccgcctcc atccagtcta ttaattgttg ccgggaagct    3420
agagtaagta gttcgccagt taatagtttg cgcaacgttg ttgccattgc tacaggcatc    3480
gtggtgtcac gctcgtcgtt tggtatggct tcattcagct ccggttccca acgatcaagg    3540
cgagttacat gatcccccat gttgtgcaaa aaagcggtta gctccttcgg tcctccgatc    3600
gttgtcagaa gtaagttggc cgcagtgtta tcactcatgg ttatggcagc actgcataat    3660
tctcttactg tcatgccatc cgtaagatgc ttttctgtga ctggtgagta ctcaaccaag    3720
tcattctgag aatagtgtat gcggcgaccg agttgctctt gcccggcgtc aatacgggat    3780
aataccgcgc cacatagcag aactttaaaa gtgctcatca ttggaaaacg ttcttcgggg    3840
cgaaaactct caaggatctt accgctgttg agatccagtt cgatgtaacc cactcgtgca    3900
cccaactgat cttcagcatc ttttactttc accagcgttt ctgggtgagc aaaaacagga    3960
aggcaaaatg ccgcaaaaaa gggaataagg gcgacacgga aatgttgaat actcatactc    4020
ttcctttttc aatattattg aagcatttat cagggttatt gtctcatgac caaaatccct    4080
taacgtgagt tttcgttcca ctgagcgtca gaccccgtag aaaagatcaa aggatcttct    4140
tgagatcctt ttttctgcg cgtaatctgc tgcttgcaaa caaaaaaacc accgctacca    4200
gcggtggttt gtttgccgga tcaagagcta ccaactcttt ttccgaaggt aactggcttc    4260
agcagagcgc agataccaaa tactgttctt ctagtgtagc cgtagttagg ccaccacttc    4320
aagaactctg tagcaccgcc tacatacctc gctctgctaa tcctgttacc agtggctgct    4380
gccagtggcg ataagtcgtg tcttaccggg ttggactcaa gacgatagtt accggataag    4440
gcgcagcggt cgggctgaac ggggggttcg tgcacacagc ccagcttgga gcgaacgacc    4500
tacaccgaac tgagatacct acagcgtgag ctatgagaaa gcgccacgct tcccgaaggg    4560
agaaaggcgg acaggtatcc ggtaagcggc agggtcggaa caggagagcg cacgagggag    4620
cttccagggg gaaacgcctg gtatctttat agtcctgtcg ggtttcgcca cctctgactt    4680
gagcgtcgat ttttgtgatg ctcgtcaggg gggcggagcc tatggaaaaa cgccagcaac    4740
```

```
gcggcctttt tacggttcct ggccttttgc tggccttttg ctcacatgtt ctttcctgcg    4800
ttatcccctg attctgtgga taaccgtatt accgcctttg agtgagctga taccgctcgc    4860
cgcagccgaa cgaccgagcg cagcgagtca gtgagcgagg aagcggaag              4909
```

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17

```
agtagacgag agtttatcga ttgaaacaat aggacaa                               37
```

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18

```
ttgtcctatt gtttcaatcg ataaactctc gtctact                               37
```

<210> SEQ ID NO 19
<211> LENGTH: 767
<212> TYPE: DNA
<213> ORGANISM: Yarrowia lipolytica

<400> SEQUENCE: 19

```
ataaactctc gtctactgat ttcacatgga acctttgcta tttcggggat aaccccctttt     60 gccattgcac gatggacgtg gcaaaagaaa gatcgccctg cggggatact tatcatgtgg    120
tcacatgctg tgattagaaa taagaaaaa ggtgcttttt tggcgctgtg attaacatct     180
cgtctgccgt gctctactag tcgcaatagc aaaaactcgc ttaatagtgt gcatagtgcg    240
gggtagcagg atactgaact acagtacgat ttgcttgcta ctgcttgtag caattacctt    300
tactgtaggg accacacctc ctggtttcaa tgtctttcct cgcctcgaca aagcaaaact    360
gtcacccaat cacaccttgt tcatattcat tagtgcatcc gttaaccttg acatgacact    420
tctcatacta gtgatagggc tgtagttgag acaagttgat tcacacggat acatacaaag    480
cctcagagag caaatgttat atactcaggg accgaccaat caaaaaaaca cactcctaat    540
aaccaccatt tccatctacg cgtactcact ctgtcagctg ccccacattg cccaatgcac    600
aatgcacaat gatgtgtgca acaacgcaa tcaaagtct atggatgctg accaaactct    660
gatcaccaag ttgcgaacat gaaaagaag acctgtgtat atataagtaa gggggagagc    720
cctaactaga tctttcgaaa acccccccgac cttcaccttc cacaacc                  767
```

<210> SEQ ID NO 20
<211> LENGTH: 9415
<212> TYPE: DNA
<213> ORGANISM: Artificial Sequence
<220> FEATURE:
<223> OTHER INFORMATION: Plasmid

<400> SEQUENCE: 20

```
catggcatgg atggtacgtc ctgtagaaac ccaacccgt gaaatcaaaa aactcgacgg      60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
```

```
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tcttaaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggataccgg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380 tctcttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaataacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
```

```
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060 ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata cggttttt cgccctttga   4500 cgttggagtc cacgttcttt aatagtggac tcttgttcca actggaaca acactcaacc   4560 ctatctcggt ctattctttt gatttataag ggattttgcc gatttcggcc tattggttaa   4620
aaaatgagct gatttaacaa aaatttaacg cgaattttaa caaatatta acgcttacaa   4680 tttccattcg ccattcaggc tgcgcaactg ttgggaaggg cgatcggtgc gggcctcttc   4740
gctattacgc cagctggcga aaggggggatg tgctgcaagg cgattaagtt gggtaacgcc   4800
agggttttcc cagtcacgac gttgtaaaac gacggccagt gaattgtaat acgactcact   4860
atagggcgaa ttgggtaccg gccccccct cgaggtcgat ggtgtcgata agcttgatat   4920
cgaattcatg tcacacaaac cgatcttcgc ctcaaggaaa cctaattcta catccgagag   4980
```

```
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta dacaacttac ttgctttatg    5280
aaaaacactt cctatttagg aaacaattta taatggcagt tcgttcattt aacaatttat    5340
gtagaataaa tgttataaat gcgtatggga atcttaaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120
ttttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc cttccaaat tgtcatgcct    6660 acaactcata taccaagcac taacctacca aacaccacta aaacccaca aaatatatct    6720 taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggtg tgaccttctg cttgccgaga    7320 tcggggggcag atccgtgaca gggctcgtac agaccgaacg cctcgttggt gtcgggcaga    7380
```

```
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat     7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaatttt    8520
cgagatttta cagatatttc tcgcagtttt tcacgtcccc ttgtccttgt cctattgttt    8580
caaataaact ctcgtctact gatttcacat ggaacctttg ctatttcggg gataaccccc    8640
tttgccattg cacgatggac gtggcaaaag aaagatcgcc ctgcggggat acttatcatg    8700
tggtcacatg ctgtgattag aaataaagaa aaaggtgctt ttttggcgct gtgattaaca    8760
tctcgtctgc cgtgctctac tagtcgcaat agcaaaaact cgcttaatag tgtgcatagt    8820
gcggggtagc aggatactga actacagtac gatttgcttg ctactgcttg tagcaattac    8880
ctttactgta gggaccacac ctcctggttt caatgtcttt cctcgcctcg acaaagcaaa    8940
actgtcaccc aatcacacct tgttcatatt cattagtgca tccgttaacc ttgacatgac    9000
acttctcata ctagtgatag ggctgtagtt gagacaagtt gattcacacg gatacataca    9060
aagcctcaga gagcaaatgt tatatactca gggaccgacc aatcaaaaaa acacactcct    9120
aataaccacc atttccatct acgcgtactc actctgtcag ctgccccaca ttgcccaatg    9180
cacaatgcac aatgatgtgt gcaaacaacg caatcaaaag tctatggatg ctgaccaaac    9240
tctgatcacc aagttgcgaa catgaaaaag aagacctgtg tatatataag taaggggag    9300 agccctaact agatctttcg aaaacccccc gaccttcacc ttccacaacc atgatcatct    9360
tatacgtttt ggccgttgcg gtctccttcc tcatcttcaa gagagtcacc tacac         9415

<210> SEQ ID NO 21
<211> LENGTH: 9348
<212> TYPE: DNA
<213> ORGANISM: Artificial Sequence
<220> FEATURE:
<223> OTHER INFORMATION: Plasmid

<400> SEQUENCE: 21
ggtggagctc cagcttttgt tccctttagt gagggttaat ttcgagcttg gcgtaatcat      60
```

```
ggtcatagct gtttcctgtg tgaaattgtt atccgctcac aattccacac aacatacgag    120
ccggaagcat aaagtgtaaa gcctggggtg cctaatgagt gagctaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gttttccat aggctccgcc     480 ccectgacga gcatcacaaa atcgacgct caagtcagag gtggcgaaac ccgacaggac     540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc    1020
agcagattac gcgcagaaaa aaggatctca agaagatcc tttgatcttt tctacggggt     1080
ctgacgctca gtggaacgaa aactcacgtt aagggatttt ggtcatgaga ttatcaaaaa    1140
ggatcttcac ctagatcctt ttaaattaaa aatgaagttt taaatcaatc taaagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
caaaaaaggg aataagggcg acacggaaat gttgaatact catactcttc ctttttcaat    2100
attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
```

```
cctgatagac ggttttttcgc cctttgacgt tggagtccac gttctttaat agtggactct    2520
tgttccaaac tggaacaaca ctcaaccccta tctcggtcta ttcttttgat ttataaggga    2580
ttttgccgat ttcggcctat tggttaaaaa atgagctgat ttaacaaaaa tttaacgcga    2640
attttaacaa atattaacg cttacaattt ccattcgcca ttcaggctgc gcaactgttg     2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttatttt attacttagt     3240 attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttgct tttacaagta caagtacatc gtacaactat gtactactgt     4080
tgatgcatcc acaacagttt gttttgtttt ttttgttttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620
tccacccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
```

```
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg ggggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagaggggg    5640 ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
accttgacgg cctcggcaat caccteggg  ccacagaagt cgccgccgag aagaacaatc    6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aataaatgat gtcgacgttt aaacagtgta cgcagtacta tagaggaaca attgccccgg   6540
agaagacggc caggccgcct agatgacaaa ttcaacaact cacagctgac tttctgccat   6600
tgccactagg gggggccttt tttatatggc caagccaagc tctccacgtc ggttgggctg   6660
cacccaacaa taaatgggta gggttgcacc aacaaaggga tgggatgggg ggtagaagat   6720
acgaggataa cggggctcaa tggcacaaat aagaacgaat actgccatta agactcgtga   6780
tccagcgact gacaccattg catcatcatc atctaagggc ctcaaaacta cctcggaact   6840
gctgcgctga tctggacacc acagaggttc cgagcacttt aggttgcacc aaatgtccca   6900
ccaggtgcag gcagaaaacg ctggaacagc gtgtacagtt tgtcttaaca aaaagtgagg   6960
gcgctgaggt cgagcagggt ggtgtgactt gttatagcct ttagagctgc gaaagcgcgt   7020
atggatttgg ctcatcaggc cagattgagg gtctgtggac acatgtcatg ttagtgtact   7080
tcaatcgccc cctggatata gccccgacaa taggccgtgg cctcattttt ttgccttccg   7140
cacatttcca ttgctcggta cccacacctt gcttctcctg cacttgccaa ccttaatact   7200
ggtttacatt gaccaacatc ttacaagcgg ggggcttgtc tagggtatat ataaacagtg   7260
```

```
gctctcccaa tcggttgcca gtctctttt tcctttcttt ccccacagat tcgaaatcta    7320
aactacacat cacaccatgg catggatggt acgtcctgta gaaacccaa cccgtgaaat     7380
caaaaaactc gacggcctgt gggcattcag tctggatcgc gaaaactgtg gaattgatca   7440
gcgttggtgg gaaagcgcgt tacaagaaag ccgggcaatt gctgtgccag gcagttttaa   7500
cgatcagttc gccgatgcag atattcgtaa ttatgcgggc aacgtctggt atcagcgcga   7560
agtctttata ccgaaaggtt gggcaggcca gcgtatcgtg ctgcgtttcg atgcggtcac   7620
tcattacggc aaagtgtggg tcaataatca ggaagtgatg gagcatcagg gcggctatac   7680
gccatttgaa gccgatgtca cgccgtatgt tattgccggg aaaagtgtac gtatcaccgt   7740
ttgtgtgaac aacgaactga actggcagac tatcccgccg ggaatggtga ttaccgacga   7800
aaacggcaag aaaaagcagt cttacttcca tgatttcttt aactatgccg ggatccatcg   7860
cagcgtaatg ctctacacca cgccgaacac ctgggtggac gatatcaccg tggtgacgca   7920
tgtcgcgcaa gactgtaacc acgcgtctgt tgactggcag gtggtggcca atggtgatgt   7980
cagcgttgaa ctgcgtgatg cggatcaaca ggtggttgca actggacaag gcactagcgg   8040
gactttgcaa gtggtgaatc cgcacctctg caaccgggt gaaggttatc tctatgaact    8100
gtgcgtcaca gccaaaagcc agacagagtg tgatatctac ccgcttcgcg tcggcatccg   8160
gtcagtggca gtgaagggcg aacagttcct gattaaccac aaaccgttct actttactgg   8220
ctttggtcgt catgaagatg cggacttacg tggcaaagga ttcgataacg tgctgatggt   8280
gcacgaccac gcattaatgg actggattgg ggccaactcc taccgtacct cgcattaccc   8340
ttacgctgaa gagatgctcg actgggcaga tgaacatggc atcgtggtga ttgatgaaac   8400
tgctgctgtc ggctttaacc tctctttagg cattggtttc gaagcgggca acaagccgaa   8460
agaactgtac agcgaagagg cagtcaacgg ggaaactcag caagcgcact acaggcgat    8520
taaagagctg atagcgcgtg acaaaaacca cccaagcgtg gtgatgtgga gtattgccaa   8580
cgaaccggat acccgtccgc aagtgcacgg gaatatttcg ccactggcgg aagcaacgcg   8640
taaactcgac ccgacgcgtc cgatcacctg cgtcaatgta atgttctgcg acgctcacac   8700
cgataccatc agcgatctct tgatgtgct gtgcctgaac cgttattacg gatggtatgt    8760
ccaaagcggc gatttggaaa cggcagagaa ggtactggaa aaagaacttc tggcctggca   8820
ggagaaactg catcagccga ttatcatcac cgaatacggc gtggatacgt tagccgggct   8880
gcactcaatg tacaccgaca tgtggagtga agagtatcag tgtgcatggc tggatatgta   8940
tcaccgcgtc tttgatcgcg tcagcgccgt cgtcggtgaa caggtatgga atttcgccga   9000
ttttgcgacc tcgcaaggca tattgcgcgt tggcggtaac aagaaaggga tcttcactcg   9060
cgaccgcaaa ccgaagtcgg cggcttttct gctgcaaaaa cgctggactg gcatgaactt   9120
cggtgaaaaa ccgcagcagg gaggcaaaca atgattaatt aactagagcg gccgccaccg   9180
cggcccgaga ttccggcctc ttcggccgcc aagcgacccg ggtggacgtc tagaggtacc   9240
tagcaattaa cagatagttt gccggtgata attctcttaa cctcccacac tcctttgaca   9300
taacgattta tgtaacgaaa ctgaaatttg accagatatt gtgtccgc               9348
```

<210> SEQ ID NO 22
<211> LENGTH: 9499
<212> TYPE: DNA
<213> ORGANISM: Artificial Sequence
<220> FEATURE:
<223> OTHER INFORMATION: Plasmid

<400> SEQUENCE: 22

```
aaacgaattc gcccttccaa tcgattgttg tgaaaattag cacggttata ttagcccgta    60
ataaatgccc gtctccatct tcatatggcc atcaccccgc aaatagccgg ccaatcaggc   120
gtatgtcacc tgttgctcac acgcatgtcc tcggaccgtt gtattgtgca agtaggggta   180
cctccccgat ccatcctcga ccagtggcac gctcaacccc acggttcgct tttctctttt   240
cgtctatcct gaactgagtt tttttccacg ccaactgata tcccttacg ttacccctc    300 atcacctggt gaggcgaaac tgtaaggtga aagctaaaaa tgacatctca gctgcacgaa   360
ggaccggggc ttaaaagacg ggctggtgct tgtgatttaa aactggacaa atctcagctt   420
gcttgaaatt ttggtctcca actgtttccg agcgaatcgc acacaaaccg ggcttctctc   480
tgcagaccac gccccgaaa ctctttctcc caccaccacc aacactccct ttccattccc    540
acaccgttcc tctctcgtgc gtcatccttg cgcaatcatc ttcgtctgcg acatattgta   600
cgacatacag taccacggaa cgtttcagac cgtcgacgtg aacacatctt aggaacagca   660
acctgagcta cagaaatcta tctataggcg ataaaaaaa cgcacccact gctcgtcctc    720
cttgctcctc gaaaccgact cctctacaca cgtcaaatcc gaggttgaaa tcttccccac   780
atttggcagc caaaccagca catcccagca acctcgcaca cgcccgaaat cgacctgtcg   840
acttggccac aaaaaaaagc accggctctg caacagttct cacgaccaat tacgtacaag   900
tacgaaatcg ttcgtggacc gtgactgata agctcccact ttttcttcta acaacaggca   960
acagacaagt cacacaaaac aaaagccatg gcatggatgg tacgtcctgt agaaacccca  1020
acccgtgaaa tcaaaaaact cgacggcctg tgggcattca gtctggatcg cgaaaactgt  1080
ggaattgatc agcgttggtg ggaaagcgcg ttacaagaaa gccgggcaat tgctgtgcca  1140
ggcagtttta acgatcagtt cgccgatgca gatattcgta attatgcggg caacgtctgg  1200
tatcagcgcg aagtctttat accgaaaggt tgggcaggcc agcgtatcgt gctgcgtttc  1260
gatgcggtca ctcattacgg caaagtgtgg gtcaataatc aggaagtgat ggagcatcag  1320
ggcggctata cgccatttga agccgatgtc acgccgtatg ttattgccgg aaaagtgta   1380 cgtatcaccg tttgtgtgaa caacgaactg aactggcaga ctatcccgcc gggaatggtg  1440
attaccgacg aaaacggcaa gaaaaagcag tcttacttcc atgatttctt taactatgcc  1500
gggatccatc gcagcgtaat gctctacacc acgccgaaca cctgggtgga cgatatcacc  1560
gtggtgacgc atgtcgcgca agactgtaac cacgcgtctg ttgactggca ggtggtggcc  1620
aatggtgatg tcagcgttga actgcgtgat gcggatcaac aggtggttgc aactggacaa  1680
ggcactagcg ggactttgca agtggtgaat ccgcacctct ggcaaccggg tgaaggttat  1740
ctctatgaac tgtgcgtcac agccaaaagc cagacagagt gtgatatcta cccgcttcgc  1800
gtcggcatcc ggtcagtggc agtgaagggc gaacagttcc tgattaacca caaaccgttc  1860
tactttactg gctttggtcg tcatgaagat gcggacttac gtggcaaagg attcgataac  1920
gtgctgatgg tgcacgacca cgcattaatg gactggattg ggccaactc ctaccgtacc   1980 tcgcattacc cttacgctga agagatgctc gactgggcag atgaacatgg catcgtggtg  2040
attgatgaaa ctgctgctgt cggctttaac ctctctttag gcattggttt cgaagcgggc  2100
aacaagccga agaactgta cagcgaagag gcagtcaacg gggaaactca gcaagcgcac   2160
ttacaggcga ttaaagagct gatagcgcgt gacaaaaacc acccaagcgt ggtgatgtgg  2220
agtattgcca acgaaccgga tacccgtccg caagtgcacg gaatatttc gccactggcg   2280 gaagcaacgc gtaaactcga cccgacgcgt ccgatcacct gctcaatgt aatgttctgc    2340 gacgctcaca ccgataccat cagcgatctc tttgatgtgc tgtgcctgaa ccgttattac  2400
```

```
ggatggtatg tccaaagcgg cgatttggaa acggcagaga aggtactgga aaaagaactt    2460
ctggcctggc aggagaaact gcatcagccg attatcatca ccgaatacgg cgtggatacg    2520
ttagccgggc tgcactcaat gtacaccgac atgtggagtg aagagtatca gtgtgcatgg    2580
ctggatatgt atcaccgcgt ctttgatcgc gtcagcgccg tcgtcggtga acaggtatgg    2640
aatttcgccg attttgcgac ctcgcaaggc atattgcgcg ttggcggtaa caagaaaggg    2700
atcttcactc gcgaccgcaa accgaagtcg gcggcttttc tgctgcaaaa acgctggact    2760
ggcatgaact tcggtgaaaa accgcagcag ggaggcaaac aatgattaat taactagagc    2820
ggccgccacc gcggcccgag attccggcct cttcggccgc caagcgaccc gggtggacgt    2880
ctagaggtac ctagcaatta acagatagtt tgccggtgat aattctctta acctcccaca    2940
ctcctttgac ataacgattt atgtaacgaa actgaaattt gaccagatat tgtgtccgcg    3000
gtggagctcc agcttttgtt ccctttagtg agggttaatt tcgagcttgg cgtaatcatg    3060
gtcatagctg tttcctgtgt gaaattgtta tccgctcaca attccacaca atacgagc     3120 cggaagcata agtgtaaag cctggggtgc ctaatgagtg agctaactca cattaattgc     3180
gttgcgctca ctgcccgctt tccagtcggg aaacctgtcg tgccagctgc attaatgaat    3240
cggccaacgc gcgggagag gcggtttgcg tattgggcgc tcttccgctt cctcgctcac    3300
tgactcgctg cgctcggtcg ttcggctgcg gcgagcggta tcagctcact caaaggcggt    3360
aatacggtta tccacagaat caggggataa cgcaggaaag aacatgtgag caaaaggcca    3420
gcaaaaggcc aggaaccgta aaaaggccgc gttgctggcg ttttccata ggctccgccc     3480 ccctgacgag catcacaaaa atcgacgctc aagtcagagg tggcgaaacc cgacaggact    3540
ataaagatac caggcgtttc cccctggaag ctccctcgtg cgctctcctg ttccgaccct    3600
gccgcttacc ggatacctgt ccgcctttct cccttcggga agcgtggcgc tttctcatag    3660
ctcacgctgt aggtatctca gttcggtgta ggtcgttcgc tccaagctgg gctgtgtgca    3720 cgaaccccc gttcagcccg accgctgcgc cttatccggt aactatcgtc ttgagtccaa     3780
cccggtaaga cacgacttat cgccactggc agcagccact ggtaacagga ttagcagagc    3840
gaggtatgta ggcggtgcta cagagttctt gaagtggtgg cctaactacg gctacactag    3900
aaggacagta tttggtatct gcgctctgct gaagccagtt accttcggaa aaagagttgg    3960
tagctcttga tccggcaaac aaaccaccgc tggtagcggt ggtttttttg tttgcaagca    4020
gcagattacg cgcagaaaaa aaggatctca agaagatcct ttgatctttt ctacggggtc    4080
tgacgctcag tggaacgaaa actcacgtta agggattttg gtcatgagat tatcaaaaag    4140
gatcttcacc tagatccttt taaattaaaa atgaagtttt aaatcaatct aaagtatata    4200
tgagtaaact tggtctgaca gttaccaatg cttaatcagt gaggcaccta tctcagcgat    4260
ctgtctattt cgttcatcca tagttgcctg actccccgtc gtgtagataa ctacgatacg    4320
ggagggctta ccatctggcc ccagtgctgc aatgataccg cgagacccac gctcaccggc    4380
tccagattta tcagcaataa accagccagc cggaagggcc gagcgcagaa gtggtcctgc    4440
aactttatcc gcctccatcc agtctattaa ttgttgccgg gaagctagag taagtagttc    4500
gccagttaat agtttgcgca acgttgttgc cattgctaca ggcatcgtgg tgtcacgctc    4560
gtcgtttggt atggcttcat tcagctccgg ttcccaacga tcaaggcgag ttacatgatc    4620
ccccatgttg tgcaaaaaag cggttagctc cttcggtcct ccgatcgttg tcagaagtaa    4680
gttggccgca gtgttatcac tcatggttat ggcagcactg cataattctc ttactgtcat    4740
gccatccgta agatgctttt ctgtgactgg tgagtactca accaagtcat tctgagaata    4800
```

```
gtgtatgcgg cgaccgagtt gctcttgccc ggcgtcaata cgggataata ccgcgccaca    4860
tagcagaact ttaaaagtgc tcatcattgg aaaacgttct cggggcgaaa actctcaag    4920 gatcttaccg ctgttgagat ccagttcgat gtaacccact cgtgcaccca actgatcttc    4980
agcatctttt actttcacca gcgtttctgg gtgagcaaaa acaggaaggc aaaatgccgc    5040
aaaaaaggga taagggcga cacggaaatg ttgaatactc atactcttcc ttttcaata    5100 ttattgaagc atttatcagg gttattgtct catgagcgga tacatatttg aatgtattta    5160
gaaaaataaa caataggggg ttccgcgcac atttccccga aaagtgccac ctgacgcgcc    5220
ctgtagcggc gcattaagcg cggcgggtgt ggtggttacg cgcagcgtga ccgctacact    5280
tgccagcgcc ctagcgcccg ctcctttcgc tttcttccct tcctttctcg ccacgttcgc    5340
cggctttccc cgtcaagctc taaatcgggg gctcccttta gggttccgat ttagtgcttt    5400
acggcacctc gaccccaaaa aacttgatta gggtgatggt tcacgtagtg gccatcgcc    5460 ctgatagacg gttttcgcc ctttgacgtt ggagtccacg ttctttaata gtggactctt    5520
gttccaaact ggaacaacac tcaacccctat ctcggtctat tcttttgatt tataagggat    5580
tttgccgatt tcggcctatt ggttaaaaaa tgagctgatt taacaaaaat ttaacgcgaa    5640
ttttaacaaa atattaacgc ttacaatttc cattcgccat tcaggctgcg caactgttgg    5700
gaagggcgat cggtgcgggc ctcttcgcta ttacgccagc tggcgaaagg gggatgtgct    5760
gcaaggcgat taagttgggt aacgccaggg ttttcccagt cacgacgttg taaaacgacg    5820
gccagtgaat tgtaatacga ctcactatag ggcgaattgg gtaccgggcc ccccctcgag    5880
gtcgatggtg tcgataagct tgatatcgaa ttcatgtcac acaaaccgat cttcgcctca    5940
aggaaaccta attctacatc cgagagactg ccgagatcca gtctacactg attaattttc    6000
gggccaataa tttaaaaaaa tcgtgttata taatattata tgtattatat atatacatca    6060
tgatgatact gacagtcatg tcccattgct aaatagacag actccatctg ccgcctccaa    6120
ctgatgttct caatatttaa ggggtcatct cgcattgttt aataataaac agactccatc    6180
taccgcctcc aaatgatgtt ctcaaaatat attgtatgaa cttatttta ttacttagta    6240 ttattagaca acttacttgc tttatgaaaa acacttccta tttaggaaac aatttataat    6300
ggcagttcgt tcatttaaca atttatgtag aataaatgtt ataaatgcgt atgggaaatc    6360
ttaaatatgg atagcataaa tgatatctgc attgcctaat tcgaaatcaa cagcaacgaa    6420
aaaaatccct tgtacaacat aaatagtcat cgagaaatat caactatcaa agaacagcta    6480
ttcacacgtt actattgaga ttattattgg acgagaatca cacactcaac tgtctttctc    6540
tcttctagaa atacaggtac aagtatgtac tattctcatt gttcatactt ctagtcattt    6600
catcccacat attccttgga tttctctcca atgaatgaca ttctatcttg caaattcaac    6660
aattataata agatatacca aagtagcggt atagtggcaa tcaaaaagct tctctggtgt    6720
gcttctcgta tttatttta ttctaatgat ccattaaagg tatatattta tttcttgtta    6780
tataatcctt tgttattta catgggctgg atacataaag gtattttgat ttaattttt    6840 gcttaaattc aatccccct cgttcagtgt caactgtaat ggtaggaaat taccatactt    6900
ttgaagaagc aaaaaaatg aaagaaaaaa aaatcgtat ttccaggtta gacgttccgc    6960
agaatctaga atgcggtatg cggtacattg ttcttcgaac gtaaagttg cgctccctga    7020 gatattgtac atttttgctt ttacaagtac aagtacatcg tacaactatg tactactgtt    7080
gatgcatcca caacagtttg ttttgttttt ttttgttttt ttttttcta atgattcatt    7140 accgctatgt atacctactt gtacttgtag taagccgggt tattggcgtt caattaatca    7200
```

```
tagacttatg aatctgcacg gtgtgcgctg cgagttactt ttagcttatg catgctactt    7260
gggtgtaata ttgggatctg ttcggaaatc aacggatgct caaccgattt cgacagtaat    7320
aatttgaatc gaatcggagc ctaaaatgaa cccgagtata tctcataaaa ttctcggtga    7380
gaggtctgtg actgtcagta caaggtgcct tcattatgcc ctcaaccttg ccatacctca    7440
ctgaatgtag tgtacctcta aaatgaaat acagtgccaa aagccaaggc actgagctcg    7500
tctaacggac ttgatataca accaattaaa acaaatgaaa agaaatacag ttctttgtat    7560
catttgtaac aattaccctg tacaaactaa ggtattgaaa tcccacaata ttcccaaagt    7620 ccacccettt ccaaattgtc atgcctacaa ctcatatacc aagcactaac ctaccaaaca    7680
ccactaaaac cccacaaaat atatcttacc gaatatacag taacaagcta ccaccacact    7740
cgttgggtgc agtcgccagc ttaaagatat ctatccacat cagccacaac tcccttcctt    7800
taataaaccg actacaccct tggctattga ggttatgagt gaatactg tagacaagac      7860 actttcaaga agactgtttc caaaacgtac cactgtcctc cactacaaac acacccaatc    7920
tgcttcttct agtcaaggtt gctacaccgg taaattataa atcatcattt cattagcagg    7980 gcagggcect ttttatagag tcttatacac tagcggaccc tgccggtaga ccaacccgca    8040
ggcgcgtcag tttgctcctt ccatcaatgc gtcgtagaaa cgacttactc cttcttgagc    8100
agctccttga ccttgttggc aacaagtctc cgacctcgga ggtggaggaa gagcctccga    8160
tatcggcggt agtgatacca gcctcgacgg actccttgac ggcagcctca acagcgtcac    8220
cggcgggctt catgttaaga gagaacttga gcatcatggc ggcagacaga atggtggcaa    8280
tggggttgac cttctgcttg ccgagatcgg gggcagatcc gtgacagggc tcgtacagac    8340
cgaacgcctc gttggtgtcg ggcagagaag ccagagaggc ggaggcage agacccagag     8400 aaccggggat gacggaggcc tcgtcggaga tgatatcgcc aaacatgttg gtggtgatga    8460
tgataccatt catcttggag ggctgcttga tgaggatcat ggcggccgag tcgatcagct    8520
ggtggttgag ctcgagctgg gggaattcgt ccttgaggac tcgagtgaca gtctttcgcc    8580
aaagtcgaga ggaggccagc acgttggcct tgtcaagaga ccacgcggga agagggggt    8640 tgtgctgaag ggccaggaag gcggccattc gggcaattcg ctcaacctca ggaacggagt    8700
aggtctcggt gtcggaagcg acgccagatc cgtcatcctc ctttcgctct ccaaagtaga    8760
tacctccgac gagctctcgg acaatgatga agtcggtgcc ctcaacgttt cggatggggg    8820
agagatcggc gagcttgggc gacagcagct ggcaggtcg caggttggcg tacaggttca     8880
ggtcctttcg cagcttgagg agaccctgct cgggtcgcac gtcggttcgt ccgtcgggag    8940
tggtccatac ggtgttggca gcgcctccga cagcaccgag cataatagag tcagcctttc    9000
ggcagatgtc gagagtagcg tcggtgatgg gctcgccctc cttctcaatg gcagctcctc    9060
caatgagtcg gtcctcaaac acaaactcgg tgccggaggc ctcagcaaca gacttgagca    9120
ccttgacggc ctcggcaatc acctcggggc cacagaagtc gccgccgaga agaacaatct    9180
tcttggagtc agtcttggtc ttcttagttt cgggttccat tgtggatgtg tgtggttgta    9240
tgtgtgatgt ggtgtgtgga gtgaaaatct gtggctggca aacgctcttg tatatatacg    9300 cactttgcc cgtgctatgt ggaagactaa acctccgaag attgtgactc aggtagtgcg     9360
gtatcggcta gggacccaaa ccttgtcgat gccgatagcg ctatcgaacg taccccagcc    9420
ggccgggagt atgtcggagg ggacatacga gatcgtcaag ggtttgtggc caactggtaa    9480
ataaatgatg tcgacgttt                                                 9499
```

```
<210> SEQ ID NO 23
<211> LENGTH: 9364
<212> TYPE: DNA
<213> ORGANISM: Artificial Sequence
<220> FEATURE:
<223> OTHER INFORMATION: Plasmid

<400> SEQUENCE: 23
```

| | | | | | |
|---|---|---|---|---|---|
| catggcatgg | atggtacgtc | ctgtagaaac | cccaacccgt | gaaatcaaaa | aactcgacgg | 60 |
| cctgtgggca | ttcagtctgg | atcgcgaaaa | ctgtggaatt | gatcagcgtt | ggtgggaaag | 120 |
| cgcgttacaa | gaaagccggg | caattgctgt | gccaggcagt | tttaacgatc | agttcgccga | 180 |
| tgcagatatt | cgtaattatg | cgggcaacgt | ctggtatcag | cgcgaagtct | ttataccgaa | 240 |
| aggttgggca | ggccagcgta | tcgtgctgcg | tttcgatgcg | gtcactcatt | acggcaaagt | 300 |
| gtgggtcaat | aatcaggaag | tgatggagca | tcagggcggc | tatacgccat | ttgaagccga | 360 |
| tgtcacgccg | tatgttattg | ccgggaaaag | tgtacgtatc | accgtttgtg | tgaacaacga | 420 |
| actgaactgg | cagactatcc | cgccgggaat | ggtgattacc | gacgaaaacg | gcaagaaaaa | 480 |
| gcagtcttac | ttccatgatt | tctttaacta | tgccgggatc | catcgcagcg | taatgctcta | 540 |
| caccacgccg | aacacctggg | tggacgatat | caccgtggtg | acgcatgtcg | cgcaagactg | 600 |
| taaccacgcg | tctgttgact | ggcaggtggt | ggccaatggt | gatgtcagcg | ttgaactgcg | 660 |
| tgatgcggat | caacaggtgg | ttgcaactgg | acaaggcact | agcgggactt | tgcaagtggt | 720 |
| gaatccgcac | ctctggcaac | cgggtgaagg | ttatctctat | gaactgtgcg | tcacagccaa | 780 |
| aagccagaca | gagtgtgata | tctacccgct | tcgcgtcggc | atccggtcag | tggcagtgaa | 840 |
| gggcgaacag | ttcctgatta | accacaaacc | gttctacttt | actggctttg | gtcgtcatga | 900 |
| agatgcggac | ttacgtggca | aaggattcga | taacgtgctg | atggtgcacg | accacgcatt | 960 |
| aatggactgg | attggggcca | actcctaccg | tacctcgcat | tacccttacg | ctgaagagat | 1020 |
| gctcgactgg | gcagatgaac | atggcatcgt | ggtgattgat | gaaactgctg | ctgtcggctt | 1080 |
| taacctctct | ttaggcattg | gtttcgaagc | gggcaacaag | ccgaaagaac | tgtacagcga | 1140 |
| agaggcagtc | aacggggaaa | ctcagcaagc | gcacttacag | gcgattaaag | agctgatagc | 1200 |
| gcgtgacaaa | aaccacccaa | gcgtggtgat | gtggagtatt | gccaacgaac | cggataccog | 1260 |
| tccgcaagtg | cacgggaata | tttcgccact | ggcggaagca | acgcgtaaac | tcgacccgac | 1320 |
| gcgtccgatc | acctgcgtca | atgtaatgtt | ctgcgacgct | cacaccgata | ccatcagcga | 1380 |
| tctctttgat | gtgctgtgcc | tgaaccgtta | ttacggatgg | tatgtccaaa | gcggcgattt | 1440 |
| ggaaacggca | gagaaggtac | tggaaaaaga | acttctggcc | tggcaggaga | aactgcatca | 1500 |
| gccgattatc | atcaccgaat | acggcgtgga | tacgttagcc | gggctgcact | caatgtacac | 1560 |
| cgacatgtgg | agtgaagagt | atcagtgtgc | atggctggat | atgtatcacc | gcgtctttga | 1620 |
| tcgcgtcagc | gccgtcgtcg | gtgaacaggt | atggaatttc | gccgattttg | cgacctcgca | 1680 |
| aggcatattg | cgcgttggcg | gtaacaagaa | agggatcttc | actcgcgacc | gcaaaccgaa | 1740 |
| gtcggcggct | tttctgctgc | aaaaacgctg | gactggcatg | aacttcggtg | aaaaaccgca | 1800 |
| gcagggaggc | aaacaatgat | taattaacta | gagcggccgc | caccgcggcc | cgagattccg | 1860 |
| gcctcttcgg | ccgccaagcg | acccgggtgg | acgtctagag | gtacctagca | attaacagat | 1920 |
| agtttgccgg | tgataattct | cttaacctcc | cacactcctt | tgcataacg | atttatgtaa | 1980 |
| cgaaactgaa | atttgaccag | atattgtgtc | cgcggtggag | ctccagcttt | tgttcccttt | 2040 |
| agtgagggtt | aatttcgagc | ttggcgtaat | catggtcata | gctgtttcct | gtgtgaaatt | 2100 |
| gttatccgct | cacaattcca | cacaacatac | gagccggaag | cataaagtgt | aaagcctggg | 2160 |

```
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
tgcggcgagc ggtatcagct cactcaaagg cggtaatacg gttatccaca gaatcagggg    2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgcccttga    4500 cgttggagtc cacgttcttt aatagtggac tcttgttcca aactggaaca acactcaacc    4560
```

```
ctatctcggt ctattctttt gatttataag ggattttgcc gatttcggcc tattggttaa       4620
aaaatgagct gatttaacaa aaatttaacg cgaatttaa caaaatatta acgcttacaa        4680
tttccattcg ccattcaggc tgcgcaactg ttgggaaggg cgatcggtgc gggcctcttc       4740
gctattacgc cagctggcga agggggatg tgctgcaagg cgattaagtt gggtaacgcc        4800
agggttttcc cagtcacgac gttgtaaaac gacggccagt gaattgtaat acgactcact       4860
atagggcgaa ttgggtaccg ggccccccct cgaggtcgat ggtgtcgata agcttgatat       4920
cgaattcatg tcacacaaac cgatcttcgc ctcaaggaaa cctaattcta catccgagag       4980
actgccgaga tccagtctac actgattaat tttcgggcca ataatttaaa aaaatcgtgt      5040
tatataatat tatatgtatt atatatatac atcatgatga tactgacagt catgtcccat       5100
tgctaaatag acagactcca tctgccgcct ccaactgatg ttctcaatat ttaaggggtc      5160
atctcgcatt gtttaataat aaacagactc catctaccgc ctccaaatga tgttctcaaa      5220
atatattgta tgaacttatt tttattactt agtattatta gacaacttac ttgctttatg      5280
aaaaacactt cctatttagg aaacaattta taatggcagt tcgttcattt aacaatttat      5340
gtagaataaa tgttataaat gcgtatggga aatcttaaat atggatagca taatgatat       5400 ctgcattgcc taattcgaaa tcaacagcaa cgaaaaaaat cccttgtaca acataaatag      5460
tcatcgagaa atatcaacta tcaaagaaca gctattcaca cgttactatt gagattatta      5520
ttggacgaga atcacacact caactgtctt tctctcttct agaaatacag gtacaagtat      5580
gtactattct cattgttcat acttctagtc atttcatccc acatattcct tggatttctc      5640
tccaatgaat gacattctat cttgcaaatt caacaattat aataagatat accaaagtag      5700
cggtatagtg gcaatcaaaa agcttctctg gtgtgcttct cgtatttatt tttattctaa      5760
tgatccatta aaggtatata tttatttctt gttatataat ccttttgttt attacatggg      5820
ctggatacat aaaggtattt tgattaatt ttttgcttaa attcaatccc ccctcgttca        5880
gtgtcaactg taatggtagg aaattaccat acttttgaag aagcaaaaaa aatgaaagaa      5940 aaaaaaatc gtatttccag gttagacgtt ccgcagaatc tagaatgcgg tatgcggtac        6000
attgttcttc gaacgtaaaa gttgcgctcc ctgagatatt gtacattttt gcttttacaa      6060
gtacaagtac atcgtacaac tatgtactac tgttgatgca tccacaacag tttgttttgt      6120 tttttttgt ttttttttt tctaatgatt cattaccgct atgtatacct acttgtactt        6180
gtagtaagcc gggttattgg cgttcaatta atcatagact tatgaatctg cacggtgtgc      6240
gctgcgagtt acttttagct tatgcatgct acttgggtgt aatattggga tctgttcgga      6300
aatcaacgga tgctcaaccg atttcgacag taataatttg aatcgaatcg gagcctaaaa      6360
tgaacccgag tatatctcat aaaattctcg gtgagaggtc tgtgactgtc agtacaaggt      6420
gccttcatta tgccctcaac cttaccatac ctcactgaat gtagtgtacc tctaaaaatg      6480
aaatacagtg ccaaaagcca aggcactgag ctcgtctaac ggacttgata tacaaccaat      6540
taaaacaaat gaaagaaat acagttcttt gtatcatttg taacaattac cctgtacaaa       6600
ctaaggtatt gaaatcccac aatattccca aagtccaccc ctttccaaat tgtcatgcct      6660
acaactcata taccaagcac taacctacca aacaccacta aaccccaca aaatatatct       6720 taccgaatat acagtaacaa gctaccacca cactcgttgg gtgcagtcgc cagcttaaag     6780
atatctatcc acatcagcca caactcccctt cctttaataa accgactaca cccttggcta     6840
ttgaggttat gagtgaatat actgtagaca agacactttc aagaagactg tttccaaaac     6900
gtaccactgt cctccactac aaacacaccc aatctgcttc ttctagtcaa ggttgctaca     6960
```

```
ccggtaaatt ataaatcatc atttcattag cagggcaggg cccttttat agagtcttat   7020 acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320 tcggggcag atccgtgaca gggctcgtac agaccaacg cctcgttggt gtcgggcaga     7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtaccc agccggccgg gagtatgtcg gagggacat    8460 acgagatcgt caagggtttg tggccaactg gtaaataaat gatgtcgacg tttaaacgaa   8520
ttcgccctat cgataaactc tcgtctactg atttcacatg gaacctttgc tatttcgggg   8580 ataacccct tgccattgc acgatggacg tggcaaaaga aagatcgccc tgcggggata     8640
cttatcatgt ggtcacatgc tgtgattaga aataaagaaa aaggtgcttt tttggcgctg   8700
tgattaacat ctcgtctgcc gtgctctact agtcgcaata gcaaaaactc gcttaatagt   8760
gtgcatagtg cggggtagca ggatactgaa ctacagtacg atttgcttgc tactgcttgt   8820
agcaattacc tttactgtag ggaccacacc tcctggtttc aatgtctttc ctcgcctcga   8880
caaagcaaaa ctgtcaccca atcacacctt gttcatattc attagtgcat ccgttaacct   8940
tgacatgaca cttctcatac tagtgatagg gctgtagttg agacaagttg attcacacgg   9000
atacatacaa agcctcagag agcaaatgtt atatactcag ggaccgacca atcaaaaaaa   9060
cacactccta ataaccacca tttccatcta cgcgtactca ctctgtcagc tgccccacat   9120
tgcccaatgc acaatgcaca atgatgtgtg caaacaacgc aatcaaaagt ctatggatgc   9180
tgaccaaact ctgatcacca agttgcgaac atgaaaaaga agacctgtgt atatataagt   9240
aaggggagag gccctaacta gatctttcga aaacccccg accttcacct tccacaacca   9300
tgatcatctt atacgttttg gccgttgcgg tctccttcct catcttcaag agagtcacct   9360
```

```
acac                                                              9364

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
ctctcgtcta ctgatttaaa tcacatggaa cctttgct                           38

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
agcaaaggtt ccatgtgatt taaatcagta gacgagag                           38

<210> SEQ ID NO 26
<211> LENGTH: 9419
<212> TYPE: DNA
<213> ORGANISM: Artificial Sequence
<220> FEATURE:
<223> OTHER INFORMATION: Plasmid

<400> SEQUENCE: 26
catggcatgg atggtacgtc ctgtagaaac cccaacccgt gaaatcaaaa aactcgacgg   60
cctgtgggca ttcagtctgg atcgcgaaaa ctgtggaatt gatcagcgtt ggtgggaaag  120
cgcgttacaa gaaagccggg caattgctgt gccaggcagt tttaacgatc agttcgccga  180
tgcagatatt cgtaattatg cgggcaacgt ctggtatcag cgcgaagtct ttataccgaa  240
aggttgggca ggccagcgta tcgtgctgcg tttcgatgcg gtcactcatt acggcaaagt  300
gtgggtcaat aatcaggaag tgatggagca tcagggcggc tatacgccat ttgaagccga  360
tgtcacgccg tatgttattg ccgggaaaag tgtacgtatc accgtttgtg tgaacaacga  420
actgaactgg cagactatcc cgccgggaat ggtgattacc gacgaaaacg gcaagaaaaa  480
gcagtcttac ttccatgatt tctttaacta tgccgggatc catcgcagcg taatgctcta  540
caccacgccg aacacctggg tggacgatat caccgtggtg acgcatgtcg cgcaagactg  600
taaccacgcg tctgttgact ggcaggtggt ggccaatggt gatgtcagcg ttgaactgcg  660
tgatgcggat caacaggtgg ttgcaactgg acaaggcact agcgggactt tgcaagtggt  720
gaatccgcac ctctggcaac cgggtgaagg ttatctctat gaactgtgcg tcacagccaa  780
aagccagaca gagtgtgata tctacccgct tcgcgtcggc atccggtcag tggcagtgaa  840
gggcgaacag ttcctgatta ccacaaaacc gttctacttt actggctttg gtcgtcatga  900
agatgcggac ttacgtggca aaggattcga taacgtgctg atggtgcacg accacgcatt  960
aatgactggg attggggcca actcctaccg tacctcgcat taccccttacg ctgaagagat 1020 gctcgactgg gcagatgaac atggcatcgt ggtgattgat gaaactgctg ctgtcggctt 1080
taacctctct ttaggcattg gtttcgaagc gggcaacaag ccgaaagaac tgtacagcga 1140
agaggcagtc aacgggggaaa ctcagcaagc gcacttacag gcgattaaag agctgatagc 1200
gcgtgacaaa aaccacccaa gcgtggtgat gtggagtatt gccaacgaac cggatacccg 1260
tccgcaagtg cacgggaata tttcgccact ggcggaagca acgcgtaaac tcgacccgac 1320
```

```
gcgtccgatc acctgcgtca atgtaatgtt ctgcgacgct cacaccgata ccatcagcga    1380
tctctttgat gtgctgtgcc tgaaccgtta ttacggatgg tatgtccaaa gcggcgattt    1440
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc accgcgccc cgagattccg      1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg tcgttcggc     2340
tgcggcgagc ggtatcagct cactcaaagg cggtaatacg ttatccaca gaatcagggg      2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat     3060
ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaccagc     3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
```

```
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttttc gccctttga    4500 cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaatatta acgcttacaa    4680 tttccattcg ccattcaggc tgcgcaactg ttgggaaggg cgatcggtgc gggcctcttc    4740
gctattacgc cagctggcga aggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taatgatat    5400 ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacatttt gcttttacaa    6060 gtacaagtac atcgtacaac tatgtactac tgttgatgca tccacaacag tttgttttgt    6120
```

```
tttttttttgt ttttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg agcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata taacccaat    6540
taaaacaaat gaaagaaat acagttcttt gtatcatttg taacaattac cctgtacaaa    6600
ctaaggtatt gaaatcccac aatattccca aagtccaccc cttttccaaat tgtcatgcct    6660
acaactcata taccaagcac taacctacca aacaccacta aaacccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320
tcgggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggggaat    7560
tcgtccttga ggactcgagt gacagtctttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gagggacat    8460
acgagatcgt caagggtttg tggccaactg gtaaataaat gatgtcgacg tttaaatttt    8520
```

| | |
|---|---|
| cgagatttta cagatatttc tcgcagtttt tcacgtcccc ttgtccttgt cctattgttt | 8580 |
| caaataaact ctcgtctact gatttaaatc acatggaacc tttgctattt cggggataac | 8640 |
| cccctttgcc attgcacgat ggacgtggca aagaaaagat cgccctgcgg ggatacttat | 8700 |
| catgtggtca catgctgtga ttagaaataa agaaaaaggt gcttttttgg cgctgtgatt | 8760 |
| aacatctcgt ctgccgtgct ctactagtcg caatagcaaa aactcgctta atagtgtgca | 8820 |
| tagtgcgggg tagcaggata ctgaactaca gtacgatttg cttgctactg cttgtagcaa | 8880 |
| ttacctttac tgtagggacc acacctcctg gtttcaatgt ctttcctcgc ctcgacaaag | 8940 |
| caaaactgtc acccaatcac accttgttca tattcattag tgcatccgtt aaccttgaca | 9000 |
| tgacacttct catactagtg atagggctgt agttgagaca agttgattca cacggataca | 9060 |
| tacaaagcct cagagagcaa atgttatata ctcagggacc gaccaatcaa aaaacacac | 9120 |
| tcctaataac caccatttcc atctacgcgt actcactctg tcagctgccc cacattgccc | 9180 |
| aatgcacaat gcacaatgat gtgtgcaaac aacgcaatca aaagtctatg gatgctgacc | 9240 |
| aaactctgat caccaagttg cgaacatgaa aaagaagacc tgtgtatata taagtaaggg | 9300 |
| ggagagccct aactagatct ttcgaaaacc ccccgacctt caccttccac aaccatgatc | 9360 |
| atcttatacg ttttggccgt tgcggtctcc ttcctcatct tcaagagagt cacctacac | 9419 |

<210> SEQ ID NO 27
<211> LENGTH: 838
<212> TYPE: DNA
<213> ORGANISM: Yarrowia lipolytica

<400> SEQUENCE: 27

| | |
|---|---|
| ttttcgagat tttacagata tttctcgcag ttttcacgt cccttgtcc ttgtcctatt | 60 |
| gtttcaaata aactctcgtc tactgattta aatcacatgg aacctttgct atttcgggga | 120 |
| taaccccctt tgccattgca cgatggacgt ggcaaaagaa agatcgccct gcggggatac | 180 |
| ttatcatgtg gtcacatgct gtgattagaa ataagaaaa aggtgctttt ttggcgctgt | 240 |
| gattaacatc tcgtctgccg tgctctacta gtcgcaatag caaaaactcg cttaatagtg | 300 |
| tgcatagtgc ggggtagcag gatactgaac tacagtacga tttgcttgct actgcttgta | 360 |
| gcaattacct ttactgtagg gaccacacct cctggtttca atgtctttcc tcgcctcgac | 420 |
| aaagcaaaac tgtcacccaa tcacaccttg ttcatattca ttagtgcatc cgttaacctt | 480 |
| gacatgacac ttctcatact agtgataggg ctgtagttga caagttga ttcacacgga | 540 |
| tacatacaaa gcctcagaga gcaaatgtta tatactcagg gaccgaccaa tcaaaaaaac | 600 |
| acactcctaa taaccaccat ttccatctac gcgtactcac tctgtcagct gccccacatt | 660 |
| gcccaatgca caatgcacaa tgatgtgtgc aaacaacgca atcaaaagtc tatggatgct | 720 |
| gaccaaactc tgatcaccaa gttgcgaaca tgaaaaagaa gacctgtgta tatataagta | 780 |
| agggggagag ccctaactag atctttcgaa aaccccccga ccttcacctt ccacaacc | 838 |

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28

| | |
|---|---|
| gatatttctc gcagtttaaa cacgtcccct tgtccttg | 38 |

```
<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
caaggacaag gggacgtgtt taaactgcga gaaatatc                               38

<210> SEQ ID NO 30
<211> LENGTH: 9414
<212> TYPE: DNA
<213> ORGANISM: Artificial Sequence
<220> FEATURE:
<223> OTHER INFORMATION: Plasmid

<400> SEQUENCE: 30
catggcatgg atggtacgtc ctgtagaaac cccaacccgt gaaatcaaaa aactcgacgg        60
cctgtgggca ttcagtctgg atcgcgaaaa ctgtggaatt gatcagcgtt ggtgggaaag      120
cgcgttacaa gaaagccggg caattgctgt gccaggcagt tttaacgatc agttcgccga      180
tgcagatatt cgtaattatg cgggcaacgt ctggtatcag cgcgaagtct ttataccgaa      240
aggttgggca ggccagcgta tcgtgctgcg tttcgatgcg gtcactcatt acggcaaagt      300
gtgggtcaat aatcaggaag tgatggagca tcagggcggc tatacgccat ttgaagccga      360
tgtcacgccg tatgttattg ccgggaaaag tgtacgtatc accgtttgtg tgaacaacga      420
actgaactgg cagactatcc cgccgggaat ggtgattacc gacgaaaacg gcaagaaaaa      480
gcagtcttac ttccatgatt tctttaacta tgccgggatc catcgcagcg taatgctcta      540
caccacgccg aacacctggg tggacgatat caccgtggtg acgcatgtcg cgcaagactg      600
taaccacgcg tctgttgact ggcaggtggt ggccaatggt gatgtcagcg ttgaactgcg      660
tgatgcggat caacaggtgg ttgcaactgg acaaggcact agcgggactt tgcaagtggt      720
gaatccgcac ctctggcaac cgggtgaagg ttatctctat gaactgtgcg tcacagccaa      780
aagccagaca gagtgtgata tctacccgct tcgcgtcggc atccggtcag tggcagtgaa      840
gggcgaacag ttcctgatta accacaaacc gttctacttt actggctttg gtcgtcatga      900
agatgcggac ttacgtggca aaggattcga taacgtgctg atggtgcacg accacgcatt      960
aatggactgg attggggcca actcctaccg tacctcgcat taccccttacg ctgaagagat     1020 gctcgactgg gcagatgaac atggcatcgt ggtgattgat gaaactgctg ctgtcggctt     1080
taacctctct ttaggcattg gtttcgaagc gggcaacaag ccgaaagaac tgtacagcga     1140
agaggcagtc aacggggaaa ctcagcaagc gcacttacag gcgattaaag agctgatagc     1200
gcgtgacaaa aaccacccaa gcgtggtgat gtggagtatt gccaacgaac cggataccccg     1260 tccgcaagtg cacgggaata tttcgccact ggcggaagca acgcgtaaac tcgacccgac     1320
gcgtccgatc acctgcgtca atgtaatgtt ctgcgacgct cacaccgata ccatcagcga     1380
tctctttgat gtgctgtgcc tgaaccgtta ttacggatgg tatgtccaaa gcggcgattt     1440
ggaaacggca gagaaggtac tggaaaaaga acttctggcc tggcaggaga aactgcatca     1500
gccgattatc atcaccgaat acggcgtgga tacgttagcc gggctgcact caatgtacac     1560
cgacatgtgg agtgaagagt atcagtgtgc atggctggat atgtatcacc gcgtctttga     1620
tcgcgtcagc gccgtcgtcg gtgaacaggt atggaatttc gccgattttg cgacctcgca     1680
aggcatattg cgcgttggcg gtaacaagaa agggatcttc actcgcgacc gcaaaccgaa     1740
gtcggcggct tttctgctgc aaaaacgctg gactggcatg aacttcggtg aaaaaccgca     1800
```

```
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg cgctcttcc gcttcctcgc tcactgactc gctgcgctcg tcgttcggc    2340 tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat    3060 ctcaagaaga tccttttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
```

```
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata gacggttttt cgcccttga    4500 cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aaggggatg tgctgcaagg cgattaagtt gggtaacgcc    4800
agggttttcc cagtcacgac gttgtaaaac gacggccagt gaattgtaat acgactcact    4860
atagggcgaa ttgggtaccg ggccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga atcttaaat atggatagca taatgatat     5400 ctgcattgcc taattcgaaa tcaacagcaa cgaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacatttt gctttacaa     6060 gtacaagtac atcgtacaac tatgtactac tgttgatgca tccacaacag tttgttttgt    6120 tttttttgt tttttttttt tctaatgatt cattaccgct atgtatacct acttgtactt     6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaatg     6480 aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
```

```
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttttat agagtcttat    7020 acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagataccctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttatttttcg    8520 agattttaca gatatttctc gcagtttaaa cacgtcccct tgtccttgtc ctattgtttc    8580
aaataaactc tcgtctactg atttcacatg gaacctttgc tatttcgggg ataacccct    8640 ttgccattgc acgatggacg tggcaaaaga agatcgccc tgcggggata cttatcatgt    8700
ggtcacatgc tgtgattaga aataaagaaa aaggtgcttt tttggcgctg tgattaacat    8760
ctcgtctgcc gtgctctact agtcgcaata gcaaaaactc gcttaatagt gtgcatagtg    8820
cggggtagca ggatactgaa ctacagtacg atttgcttgc tactgcttgt agcaattacc    8880
tttactgtag ggaccacacc tcctggtttc aatgtctttc ctcgcctcga caaagcaaaa    8940
ctgtcaccca atcacacctt gttcatattc attagtgcat ccgttaacct tgacatgaca    9000
```

-continued

| | | |
|---|---|---|
| cttctcatac tagtgatagg gctgtagttg agacaagttg attcacacgg atacatacaa | 9060 |
| agcctcagag agcaaatgtt atatactcag ggaccgacca atcaaaaaaa cacactccta | 9120 |
| ataaccacca tttccatcta cgcgtactca ctctgtcagc tgccccacat tgcccaatgc | 9180 |
| acaatgcaca atgatgtgtg caaacaacgc aatcaaaagt ctatggatgc tgaccaaact | 9240 |
| ctgatcacca agttgcgaac atgaaaaaga agacctgtgt atatataagt aaggggggaga | 9300 |
| gccctaacta gatctttcga aaaccccccg accttcacct tccacaacca tgatcatctt | 9360 |
| atacgttttg gccgttgcgg tctccttcct catcttcaag agagtcacct acac | 9414 |

<210> SEQ ID NO 31
<211> LENGTH: 835
<212> TYPE: DNA
<213> ORGANISM: Yarrowia lipolytica

<400> SEQUENCE: 31

| | | |
|---|---|---|
| ttttcgagat tttacagata tttctcgcag tttaaacacg tccccttgtc cttgtcctat | 60 |
| tgtttcaaat aaactctcgt ctactgattt cacatggaac ctttgctatt tcggggataa | 120 |
| ccccctttgc cattgcacga tggacgtggc aaaagaaaga tcgccctgcg ggatactta | 180 |
| tcatgtggtc acatgctgtg attagaaata agaaaaagg tgcttttttg gcgctgtgat | 240 |
| taacatctcg tctgccgtgc tctactagtc gcaatagcaa aaactcgctt aatagtgtgc | 300 |
| atagtgcggg gtagcaggat actgaactac agtacgattt gcttgctact gcttgtagca | 360 |
| attacctta ctgtagggac cacacctcct ggtttcaatg tctttcctcg cctcgacaaa | 420 |
| gcaaaactgt cacccaatca caccttgttc atattcatta gtgcatccgt taaccttgac | 480 |
| atgcacttc tcatactagt gatagggctg tagttgagac aagttgattc acacggatac | 540 |
| atacaaagcc tcagagagca atgttatat actcagggac cgaccaatca aaaaacaca | 600 |
| ctcctaataa ccaccatttc catctacgcg tactcactct gtcagctgcc ccacattgcc | 660 |
| caatgcacaa tgcacaatga tgtgtgcaaa caacgcaatc aaaagtctat ggatgctgac | 720 |
| caaactctga tcaccaagtt gcgaacatga aaagaagac ctgtgtatat ataagtaagg | 780 |
| gggagagccc taactagatc tttcgaaaac ccccgacct tcaccttcca caacc | 835 |

<210> SEQ ID NO 32
<211> LENGTH: 38
<212> TYPE: DNA
<213> ORGANISM: Artificial Sequence
<220> FEATURE:
<223> OTHER INFORMATION: Primer

<400> SEQUENCE: 32

| | |
|---|---|
| cagggaccga ccaatcgttt aaacacactc ctaataac | 38 |

<210> SEQ ID NO 33
<211> LENGTH: 38
<212> TYPE: DNA
<213> ORGANISM: Artificial Sequence
<220> FEATURE:
<223> OTHER INFORMATION: Primer

<400> SEQUENCE: 33

| | |
|---|---|
| gttattagga gtgtgtttaa acgattggtc ggtccctg | 38 |

<210> SEQ ID NO 34
<211> LENGTH: 9414
<212> TYPE: DNA
<213> ORGANISM: Artificial Sequence

```
<220> FEATURE:
<223> OTHER INFORMATION: Plasmid

<400> SEQUENCE: 34
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcaggcggc tatacgccat ttgaagccga     360
tgtcacgccg tatgttattg ccgggaaaag tgtacgtatc accgtttgtg tgaacaacga     420
actgaactgg cagactatcc cgccgggaat ggtgattacc gacgaaaacg gcaagaaaaa     480
gcagtcttac ttccatgatt tctttaacta tgccgggatc catcgcagcg taatgctcta     540
cacccacgcc aacacctggg tggacgtat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt tgcaagtggt     720
gaatccgcac ctctggcaac cgggtgaagg ttatctctat gaactgtgcg tcacagccaa     780
aagccagaca gagtgtgata tctacccgct tcgcgtcggc atccggtcag tggcagtgaa     840
gggcgaacag ttcctgatta accacaaacc gttctacttt actggctttg gtcgtcatga     900
agatgcggac ttacgtggca aaggattcga taacgtgctg atggtgcacg accacgcatt     960
aatggactgg attggggcca actcctaccg tacctcgcat tacccttacg ctgaagagat    1020
gctcgactgg gcagatgaac atggcatcgt ggtgattgat gaaactgctg ctgtcggctt    1080
taacctctct ttaggcattg gtttcgaagc gggcaacaag ccgaaagaac tgtacagcga    1140
agaggcagtc aacggggaaa ctcagcaagc gcacttacag gcgattaaag agctgatagc    1200
gcgtgacaaa aaccacccaa gcgtggtgat gtggagtatt gccaacgaac cggatacccg    1260
tccgcaagtg cacgggaata tttcgccact ggcggaagca acgcgtaaac tcgacccgac    1320
gcgtccgatc acctgcgtca atgtaatgtt ctgcgacgct cacaccgata ccatcagcga    1380
tctctttgat gtgctgtgcc tgaaccgtta ttacggatgg tatgtccaaa gcggcgattt    1440
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
```

```
tgcgtattgg gcgctcttcc gcttcctcgc tcactgactc gctgcgctcg gtcgttcggc    2340
tgcggcgagc ggtatcagct cactcaaagg cggtaatacg gttatccaca gaatcagggg    2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt ccccgtcaa gctctaaatc    4380 gggggctccc tttagggttc cgatttagtg ctttacggca cctcgacccc aaaaaacttg    4440
attagggtga tggttcacgt agtgggccat cgccctgata cggttttt cgcccttga    4500 cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta cgcttacaa    4680
```

```
tttccattcg ccattcaggc tgcgcaactg ttgggaaggg cgatcggtgc gggcctcttc    4740
gctattacgc cagctggcga aaggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taatgatat    5400 ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat cctttgttt attacatggg    5820 ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120
ttttttttgt ttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactcccct cctttaataa accgactaca ccttggcta    6840 ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttttat agagtcttat    7020 acactagcgg accctgccgg tagaccaacc cgcaggcgcg tcagtttgct ccttccatca    7080
```

```
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggcag atccgtgaca gggctcgtac agaccgaacg cctcgttggt gtcgggcaga     7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttattttcg    8520
agattttaca gatatttctc gcagtttaaa cacgtcccct tgtccttgtc ctattgtttc    8580
aaataaactc tcgtctactg atttcacatg gaacctttgc tatttcgggg ataaccccct    8640
ttgccattgc acgatggacg tggcaaaaga agatcgccc tgcggggata cttatcatgt     8700
ggtcacatgc tgtgattaga aataaagaaa aaggtgcttt tttggcgctg tgattaacat    8760
ctcgtctgcc gtgctctact agtcgcaata gcaaaaactc gcttaatagt gtgcatagtg    8820
cggggtagca ggatactgaa ctacagtacg atttgcttgc tactgcttgt agcaattacc    8880
tttactgtag ggaccacacc tcctggtttc aatgtctttc ctcgcctcga caaagcaaaa    8940
ctgtcaccca atcacacctt gttcatattc attagtgcat ccgttaacct tgacatgaca    9000
cttctcatac tagtgatagg gctgtagttg agacaagttg attcacacgg atacatacaa    9060
agcctcagag agcaaatgtt atatactcag ggaccgacca atcgtttaaa cacactccta    9120
ataaccacca tttccatcta cgcgtactca ctctgtcagc tgcccacat tgcccaatgc     9180 acaatgcaca atgatgtgtg caaacaacgc aatcaaaagt ctatggatgc tgaccaaact    9240
ctgatcacca agttgcgaac atgaaaaaga agacctgtgt atatataagt aagggggaga    9300
gccctaacta gatctttcga aaaccccccg accttcacct tccacaacca tgatcatctt    9360
atacgttttg gccgttgcgg tctccttcct catcttcaag agagtcacct acac          9414
```

-continued

```
<210> SEQ ID NO 35
<211> LENGTH: 835
<212> TYPE: DNA
<213> ORGANISM: Yarrowia lipolytica

<400> SEQUENCE: 35
ttttcgagat ttacagata tttctcgcag tttaaacacg tccccttgtc cttgtcctat      60
tgtttcaaat aaactctcgt ctactgattt cacatggaac ctttgctatt tcggggataa    120 cccccttttgc cattgcacga tggacgtggc aaaagaaaga tcgccctgcg gggatactta   180
tcatgtggtc acatgctgtg attagaaata agaaaaagg tgcttttttg gcgctgtgat     240
taacatctcg tctgccgtgc tctactagtc gcaatagcaa aaactcgctt aatagtgtgc    300
atagtgcggg gtagcaggat actgaactac agtacgattt gcttgctact gcttgtagca    360
attaccttta ctgtagggac cacacctcct ggtttcaatg tctttcctcg cctcgacaaa    420
gcaaaactgt cacccaatca caccttgttc atattcatta gtgcatccgt taaccttgac    480
atgacacttc tcatactagt gatagggctg tagttgagac aagttgattc acacggatac    540
atacaaagcc tcagagagca aatgttatat actcagggac cgaccaatcg tttaaacaca    600
ctcctaataa ccaccatttc catctacgcg tactcactct gtcagctgcc ccacattgcc    660
caatgcacaa tgcacaatga tgtgtgcaaa caacgcaatc aaaagtctat ggatgctgac    720
caaactctga tcaccaagtt gcgaacatga aaagaagac ctgtgtatat ataagtaagg     780
gggagagccc taactagatc tttcgaaaac cccccgacct tcaccttcca caacc          835

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
tcattagtgc atccgtttaa accttgacat gacact                                36

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
agtgtcatgt caaggtttaa acggatgcac taatga                                36

<210> SEQ ID NO 38
<211> LENGTH: 9416
<212> TYPE: DNA
<213> ORGANISM: Artificial Sequence
<220> FEATURE:
<223> OTHER INFORMATION: Plasmid

<400> SEQUENCE: 38
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
```

```
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccgaaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg tcgttcggc    2340 tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
```

```
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgccctttga     4500 cgttggagtc cacgttcttt aatagtggac tcttgttcca aactggaaca cactcaacc     4560 ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg ggccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaagggtc     5160
```

```
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga atcttaaat atggatagca taaatgatat     5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc cctcgttca    5880 gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120
ttttttttgt ttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata taacaaccat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactcccct cctttaataa accgactaca cccttggcta    6840
ttgaggttat gagtgaatat actgtagaca agacactttc aagaagactg ttccaaaac    6900 gtaccactgt cctccactac aaacacaccc aatctgcttc ttctagtcaa ggttgctaca    6960
ccggtaaatt ataaatcatc atttcattag cagggcaggg cccttttat agagtcttat    7020 acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560
```

```
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc  gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttatttttcg   8520
agattttaca gatatttctc gcagtttaaa cacgtcccct tgtccttgtc ctattgtttc    8580
aaataaactc tcgtctactg atttcacatg gaacctttgc tatttcgggg ataaccccct    8640
ttgccattgc acgatggacg tggcaaaaga agatcgccc  tgcggggata cttatcatgt    8700
ggtcacatgt tgtgattaga aataaagaaa aaggtgcttt tttggcgctg tgattaacat    8760
ctcgtctgcc gtgctctact agtcgcaata gcaaaaactc gcttaatagt gtgcatagtg    8820
cggggtagca ggatactgaa ctacagtacg atttgcttgc tactgcttgt agcaattacc    8880
tttactgtag ggaccacacc tcctggtttc aatgtctttc ctcgcctcga caaagcaaaa    8940
ctgtcaccca atcacacctt gttcatattc attagtgcat ccgtttaaac cttgacatga    9000
cacttctcat actagtgata gggctgtagt tgagacaagt tgattcacac ggatacatac    9060
aaagcctcag agagcaaatg ttatatactc agggaccgac caatcaaaaa aacacactcc    9120
taataaccac catttccatc tacgcgtact cactctgtca gctgcccac  attgcccaat    9180
gcacaatgca caatgatgtg tgcaaacaac gcaatcaaaa gtctatggat gctgaccaaa    9240
ctctgatcac caagttgcga acatgaaaaa gaagacctgt gtatatataa gtaaggggga    9300
gagccctaac tagatctttc gaaaaccccc cgaccttcac cttccacaac catgatcatc    9360
ttatacgttt tggccgttgc ggtctccttc ctcatcttca agagagtcac ctacac       9416

<210> SEQ ID NO 39
<211> LENGTH: 837
<212> TYPE: DNA
<213> ORGANISM: Yarrowia lipolytica

<400> SEQUENCE: 39
ttttcgagat tttacagata tttctcgcag tttaaacacg tccccttgtc cttgtcctat      60
tgtttcaaat aaactctcgt ctactgattt cacatggaac ctttgctatt tcggggataa    120
ccccctttgc cattgcacga tggacgtggc aaaagaaaga tcgccctgcg gggatactta    180
tcatgtggtc acatgctgtg attagaaata agaaaaagg  tgcttttttg gcgctgtgat    240
taacatctcg tctgccgtgc tctactagtc gcaatagcaa aaactcgctt aatagtgtgc    300
```

```
atagtgcggg gtagcaggat actgaactac agtacgattt gcttgctact gcttgtagca    360
attaccttta ctgtagggac cacacctcct ggtttcaatg tctttcctcg cctcgacaaa    420
gcaaaactgt cacccaatca caccttgttc atattcatta gtgcatccgt ttaaaccttg    480
acatgacact tctcatacta gtgatagggc tgtagttgag acaagttgat tcacacggat    540
acatacaaag cctcagagag caaatgttat atactcaggg accgaccaat caaaaaaaca    600
cactcctaat aaccaccatt tccatctacg cgtactcact ctgtcagctg ccccacattg    660
cccaatgcac aatgcacaat gatgtgtgca acaacgcaa tcaaaagtct atggatgctg    720
accaaactct gatcaccaag ttgcgaacat gaaaagaag acctgtgtat atataagtaa    780
gggggagagc cctaactaga tctttcgaaa accccccgac cttcaccttc cacaacc      837
```

<210> SEQ ID NO 40
<211> LENGTH: 43
<212> TYPE: DNA
<213> ORGANISM: Artificial Sequence
<220> FEATURE:
<223> OTHER INFORMATION: Primer

<400> SEQUENCE: 40

```
tgcggggtag caggatactg tttaaactac agtacgattt gct                       43
```

<210> SEQ ID NO 41
<211> LENGTH: 43
<212> TYPE: DNA
<213> ORGANISM: Artificial Sequence
<220> FEATURE:
<223> OTHER INFORMATION: Primer

<400> SEQUENCE: 41

```
agcaaatcgt actgtagttt aaacagtatc ctgctacccc gca                       43
```

<210> SEQ ID NO 42
<211> LENGTH: 9418
<212> TYPE: DNA
<213> ORGANISM: Artificial Sequence
<220> FEATURE:
<223> OTHER INFORMATION: Plasmid

<400> SEQUENCE: 42

```
catggcatgg atggtacgtc ctgtagaaac cccaacccgt gaaatcaaaa aactcgacgg    60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccggatc atcgcagcg taatgctcta    540 caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt gcaagtggt    720 gaatccgcac ctctgcaac cgggtgaagg ttatctctat gaactgtgcg tcacagccaa    780
aagccagaca gagtgtgata tctacccgct tcgcgtcggc atccggtcag tggcagtgaa    840
```

```
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacgggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttccctt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg tcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060
ctcaagaaga tcctttgatc ttttctacgg ggtctgacgc tcagtggaac gaaaactcac   3120
gttaaggat tttggtcatg agattatcaa aaaggatctt cacctagatc cttttaaatt   3180
aaaaatgaag ttttaaatca atctaaagta tatatgagta aacttggtct gacagttacc   3240
```

```
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttccttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata cggttttt cgccctttga   4500 cgttggagtc cacgttcttt aatagtggac tcttgttcca aactgaaca acactcaacc   4560 ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggcccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaat atggatagca taatgatat   5400 ctgcattgcc taattcgaaa tcaacagcaa cgaaaaaaat cccttgtaca acataaaatag   5460 tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
```

```
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat cctttgtttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacttttt gcttttacaa    6060 gtacaagtac atcgtacaac tatgtactac tgttgatgca tccacaacag tttgttttgt    6120 tttttttgt ttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttat agagtcttat    7020 acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagataccctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
```

```
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcactt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg aggggacat    8460 acgagatcgt caagggtttg tggccaactg gtaaataaat gatgtcgacg tttattttcg    8520
agattttaca gatatttctc gcagtttaaa cacgtcccct tgtccttgtc ctattgtttc    8580
aaataaactc tcgtctactg atttcacatg gaacctttgc tatttcgggg ataaccccct    8640
ttgccattgc acgatggacg tggcaaaaga aagatcgccc tgcggggata cttatcatgt    8700
ggtcacatgc tgtgattaga aataaagaaa aaggtgcttt tttggcgctg tgattaacat    8760
ctcgtctgcc gtgctctact agtcgcaata gcaaaaactc gcttaatagt gtgcatagtg    8820
cggggtagca ggatactgtt taaactacag tacgatttgc ttgctactgc ttgtagcaat    8880 taccttact gtagggacca cacctcctgg tttcaatgtc tttcctcgcc tcgacaaagc    8940
aaaactgtca cccaatcaca ccttgttcat attcattagt gcatccgtta accttgacat    9000
gacacttctc atactagtga tagggctgta gttgagacaa gttgattcac acggatacat    9060
acaaagcctc agagagcaaa tgttatatac tcagggaccg accaatcaaa aaaacacact    9120
cctaataacc accatttcca tctacgcgta ctcactctgt cagctgcccc acattgccca    9180
atgcacaatg cacaatgatg tgtgcaaaca acgcaatcaa aagtctatgg atgctgacca    9240
aactctgatc accaagttgc gaacatgaaa agaagacct gtgtatatat aagtaagggg    9300
gagagcccta actagatctt tcgaaaaccc cccgaccttc accttccaca accatgatca    9360
tcttatacgt tttggccgtt gcggtctcct tcctcatctt caagagagtc acctacac     9418
```

<210> SEQ ID NO 43
<211> LENGTH: 839
<212> TYPE: DNA
<213> ORGANISM: Yarrowia lipolytica

<400> SEQUENCE: 43

```
ttttcgagat tttacagata tttctcgcag tttaaacacg tcccttgtc cttgtcctat      60 tgtttcaaat aaactctcgt ctactgattt cacatggaac ctttgctatt tcggggataa    120 cccccttgc cattgcacga tggacgtggc aaagaaaga tcgccctgcg ggatactta    180 tcatgtggtc acatgctgtg attagaaata agaaaaagg tgcttttttg gcgctgtgat    240
taacatctcg tctgccgtgc tctactagtc gcaatagcaa aaactcgctt aatagtgtgc    300
atagtgcggg gtagcaggat actgtttaaa ctacagtacg atttgcttgc tactgcttgt    360
agcaattacc tttactgtag ggaccacacc tcctggtttc aatgtctttc ctcgcctcga    420
caaagcaaaa ctgtcaccca atcacacctt gttcatattc attagtgcat ccgttaacct    480
tgacatgaca cttctcatac tagtgatagg gctgtagttg agacaagttg attcacacgg    540
atacatacaa agcctcagag agcaaatgtt atatactcag ggaccgacca atcaaaaaaa    600
cacactccta ataaccacca tttccatcta cgcgtactca ctctgtcagc tgccccacat    660
tgcccaatgc acaatgcaca atgatgtgtg caaacaacgc aatcaaaagt ctatggatgc    720
tgaccaaact ctgatcacca agttgcgaac atgaaaaaga gacctgtgt atatataagt    780
```

```
aaggggggaga gccctaacta gatctttcga aaaccccccg accttcacct tccacaacc      839

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44
ggatacttat catgtggttt aaacacatgc tgtgattaga aa                         42

<210> SEQ ID NO 45
<211> LENGTH: 42
<212> TYPE: DNA
<213> ORGANISM: Artificial Sequence
<220> FEATURE:
<223> OTHER INFORMATION: Primer

<400> SEQUENCE: 45
tttctaatca cagcatgtgt ttaaaccaca tgataagtat cc                         42

<210> SEQ ID NO 46
<211> LENGTH: 9419
<212> TYPE: DNA
<213> ORGANISM: Artificial Sequence
<220> FEATURE:
<223> OTHER INFORMATION: Plasmid

<400> SEQUENCE: 46
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat ttgaagccga     360
tgtcacgccg tatgttattg ccgggaaaag tgtacgtatc accgtttgtg tgaacaacga     420
actgaactgg cagactatcc cgccgggaat ggtgattacc gacgaaaacg gcaagaaaaa     480
gcagtcttac ttccatgatt tctttaacta tgccgggatc catcgcagcg taatgctcta     540
caccacgccg aacacctggg tggacgatat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt tgcaagtggt     720
gaatccgcac ctctggcaac cgggtgaagg ttatctctat gaactgtgcg tcacagccaa     780
aagccagaca gagtgtgata tctacccgct tcgcgtcggc atccggtcag tggcagtgaa     840
gggcgaacag ttcctgatta ccacaaaacc gttctacttt actggctttg gtcgtcatga     900
agatgcggac ttacgtggca aaggattcga taacgtgctg atggtgcacg accacgcatt     960
aatggactgg attggggcca actcctaccg tacctcgcat taccccttacg ctgaagagat    1020 gctcgactgg gcagatgaac atggcatcgt ggtgattgat gaaactgctg ctgtcggctt    1080
taacctctct ttaggcattg gtttcgaagc gggcaacaag ccgaaagaac tgtacagcga    1140
agaggcagtc aacggggaaa ctcagcaagc gcacttacag gcgattaaag agctgatagc    1200
gcgtgacaaa aaccacccaa gcgtggtgat gtggagtatt gccaacgaac cggataccccg    1260 tccgcaagtg cacgggaata tttcgccact ggcggaagca acgcgtaaac tcgacccgac    1320
```

```
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcgccc gagattccg   1860 gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc gcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg tcgttcggc   2340 tgcggcgagc ggtatcagct cactcaaagg cggtaatacg ttatccaca gaatcagggg   2400 ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060 ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaccagc   3420 cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatccccat gttgtgcaaa aaagcggtta   3660
gctccttcgg tcctccgatc gttgtcagaa gtaagttggc cgcagtgtta tcactcatgg   3720
```

```
ttatggcagc actgcataat tctcttactg tcatgccatc cgtaagatgc ttttctgtga      3780
ctggtgagta ctcaaccaag tcattctgag aatagtgtat gcggcgaccg agttgctctt      3840
gcccggcgtc aatacgggat aataccgcgc cacatagcag aactttaaaa gtgctcatca      3900
ttggaaaacg ttcttcgggg cgaaaactct caaggatctt accgctgttg agatccagtt      3960
cgatgtaacc cactcgtgca cccaactgat cttcagcatc ttttactttc accagcgttt      4020
ctgggtgagc aaaaacagga aggcaaaatg ccgcaaaaaa gggaataagg gcgacacgga      4080
aatgttgaat actcatactc ttcctttttc aatattattg aagcatttat cagggttatt      4140
gtctcatgag cggatacata tttgaatgta tttagaaaaa taaacaaata ggggttccgc      4200
gcacatttcc ccgaaaagtg ccacctgacg cgccctgtag cggcgcatta agcgcggcgg      4260
gtgtggtggt tacgcgcagc gtgaccgcta cacttgccag cgccctagcg cccgctcctt      4320
tcgctttctt cccttccttt ctcgccacgt tcgccggctt tccccgtcaa gctctaaatc      4380
gggggctccc tttagggttc cgatttagtg ctttacggca cctcgacccc aaaaaacttg      4440
attagggtga tggttcacgt agtgggccat cgccctgata cggttttt cgccctttga       4500 cgttggagtc cacgttcttt aatagtggac tcttgttcca aactgaaca acactcaacc       4560 ctatctcggt ctattctttt gatttataag ggattttgcc gatttcggcc tattggttaa      4620
aaaatgagct gatttaacaa aaatttaacg cgaattttaa caaatatta acgcttacaa       4680 tttccattcg ccattcaggc tgcgcaactg ttgggaaggg cgatcggtgc gggcctcttc      4740
gctattacgc cagctggcga aagggggatg tgctgcaagg cgattaagtt gggtaacgcc      4800
agggttttcc cagtcacgac gttgtaaaac gacggccagt gaattgtaat acgactcact      4860
atagggcgaa ttgggtaccg gccccccct cgaggtcgat ggtgtcgata agcttgatat      4920
cgaattcatg tcacacaaac cgatcttcgc ctcaaggaaa cctaattcta catccgagag      4980
actgccgaga tccagtctac actgattaat tttcgggcca ataatttaaa aaaatcgtgt      5040
tatataatat tatatgtatt atatatatac atcatgatga tactgacagt catgtcccat      5100
tgctaaatag acagactcca tctgccgcct ccaactgatg ttctcaatat ttaaggggtc      5160
atctcgcatt gtttaataat aaacagactc catctaccgc ctccaaatga tgttctcaaa      5220
atatattgta tgaacttatt tttattactt agtattatta gacaacttac ttgctttatg      5280
aaaaacactt cctatttagg aaacaattta taatggcagt tcgttcattt aacaatttat      5340
gtagaataaa tgttataaat gcgtatggga aatcttaaat atggatagca taatgatat      5400 ctgcattgcc taattcgaaa tcaacagcaa cgaaaaaat cccttgtaca acataaatag      5460
tcatcgagaa atatcaacta tcaaagaaca gctattcaca cgttactatt gagattatta      5520
ttggacgaga atcacacact caactgtctt tctctcttct agaaatacag gtacaagtat      5580
gtactattct cattgttcat acttctagtc atttcatccc acatattcct tggatttctc      5640
tccaatgaat gacattctat cttgcaaatt caacaattat aataagatat accaaagtag      5700
cggtatagtg gcaatcaaaa agcttctctg gtgtgcttct cgtatttatt tttattctaa      5760
tgatccatta aaggtatata tttatttctt gttatataat cctttgtttt attacatggg      5820
ctggatacat aaaggtattt tgatttaatt ttttgcttaa attcaatccc ccctcgttca      5880
gtgtcaactg taatggtagg aaattaccat acttttgaag aagcaaaaaa aatgaaagaa      5940
aaaaaaaatc gtatttccag gttagacgtt ccgcagaatc tagaatgcgg tatgcggtac      6000
attgttcttc gaacgtaaaa gttgcgctcc ctgagatatt gtacatttt gcttttacaa      6060 gtacaagtac atcgtacaac tatgtactac tgttgatgca tccacaacag tttgttttgt      6120
```

```
tttttttttgt ttttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg agcctaaaa    6360 tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca acaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gagggacat    8460 acgagatcgt caagggtttg tggccaactg gtaaataaat gatgtcgacg tttatttttcg    8520
```

```
agattttaca gatatttctc gcagtttaaa cacgtcccct tgtccttgtc ctattgtttc   8580
aaataaactc tcgtctactg atttcacatg gaacctttgc tatttcgggg ataaccccct   8640
ttgccattgc acgatggacg tggcaaaaga aagatcgccc tgcggggata cttatcatgt   8700
ggtttaaaca catgctgtga ttagaaataa agaaaaaggt gcttttttgg cgctgtgatt   8760
aacatctcgt ctgccgtgct ctactagtcg caatagcaaa aactcgctta atagtgtgca   8820
tagtgcgggg tagcaggata ctgaactaca gtacgatttg cttgctactg cttgtagcaa   8880
ttacctttac tgtagggacc acacctcctg gtttcaatgt cttccctcgc ctcgacaaag   8940
caaaactgtc acccaatcac accttgttca tattcattag tgcatccgtt aaccttgaca   9000
tgacacttct catactagtg atagggctgt agttgagaca agttgattca cacggataca   9060
tacaaagcct cagagagcaa atgttatata ctcagggacc gaccaatcaa aaaaacacac   9120
tcctaataac caccatttcc atctacgcgt actcactctg tcagctgccc cacattgccc   9180
aatgcacaat gcacaatgat gtgtgcaaac aacgcaatca aaagtctatg gatgctgacc   9240
aaactctgat caccaagttg cgaacatgaa aagaagacc  tgtgtatata taagtaaggg   9300
ggagagccct aactagatct ttcgaaaacc ccccgacctt caccttccac aaccatgatc   9360
atcttatacg ttttggccgt tgcggtctcc ttcctcatct tcaagagagt cacctacac    9419

<210> SEQ ID NO 47
<211> LENGTH: 840
<212> TYPE: DNA
<213> ORGANISM: Yarrowia lipolytica

<400> SEQUENCE: 47
ttttcgagat tttacagata tttctcgcag tttaaacacg tccccttgtc cttgtcctat     60
tgtttcaaat aaactctcgt ctactgattt cacatggaac ctttgctatt cggggataa    120 ccccctttgc cattgcacga tggacgtggc aaaagaaaga tcgccctgcg ggatactta    180 tcatgtggtt taaacacatg ctgtgattag aaataaagaa aaggtgctt ttttggcgct    240 gtgattaaca tctcgtctgc cgtgctctac tagtcgcaat agcaaaaact cgcttaatag    300
tgtgcatagt gcggggtagc aggatactga actacagtac gatttgcttg ctactgcttg    360
tagcaattac ctttactgta gggaccacac ctcctggttt caatgtcttt cctcgcctcg    420
acaaagcaaa actgtcaccc aatcacacct tgttcatatt cattagtgca tccgttaacc    480
ttgacatgac acttctcata ctagtgatag ggctgtagtt gagacaagtt gattcacacg    540
gatacataca aagcctcaga gagcaaatgt tatatactca gggaccgacc aatcaaaaaa    600
acacactcct aataaccacc atttccatct acgcgtactc actctgtcag ctgccccaca    660
ttgcccaatg cacaatgcac aatgatgtgt gcaaacaacg caatcaaaag tctatggatg    720
ctgaccaaac tctgatcacc aagttgcgaa catgaaaaag aagacctgtg tatatataag    780 taaggggag agccctaact agatctttcg aaaaccccc  gaccttcacc ttccacaacc    840

<210> SEQ ID NO 48
<211> LENGTH: 9261
<212> TYPE: DNA
<213> ORGANISM: Artificial Sequence
<220> FEATURE:
<223> OTHER INFORMATION: Plasmid

<400> SEQUENCE: 48
aaacacatgc tgtgattaga aataaagaaa aggtgctttt ttggcgctgt gattaacat     60 ctcgtctgcc gtgctctact agtcgcaata gcaaaaactc gcttaatagt gtgcatagtg    120
```

```
cggggtagca ggatactgaa ctacagtacg atttgcttgc tactgcttgt agcaattacc    180
tttactgtag ggaccacacc tcctggtttc aatgtctttc ctcgcctcga caaagcaaaa    240
ctgtcaccca atcacacctt gttcatattc attagtgcat ccgttaacct tgacatgaca    300
cttctcatac tagtgatagg gctgtagttg agacaagttg attcacacgg atacatacaa    360
agcctcagag agcaaatgtt atatactcag ggaccgacca atcaaaaaaa cacactccta    420
ataaccacca tttccatcta cgcgtactca ctctgtcagc tgccccacat tgcccaatgc    480
acaatgcaca atgatgtgtg caaacaacgc aatcaaaagt ctatggatgc tgaccaaact    540
ctgatcacca agttgcgaac atgaaaaaga agacctgtgt atatataagt aaggggggaga   600
gccctaacta gatctttcga aaaccccccg accttcacct tccacaacca tgatcatctt    660
atacgttttg gccgttgcgg tctccttcct catcttcaag agagtcacct acaccatggc    720
atggatggta cgtcctgtag aaaccccaac ccgtgaaatc aaaaaactcg acggcctgtg    780
ggcattcagt ctggatcgcg aaaactgtgg aattgatcag cgttggtggg aaagcgcgtt    840
acaagaaagc cgggcaattg ctgtgccagg cagttttaac gatcagttcg ccgatgcaga    900
tattcgtaat tatgcgggca acgtctggta tcagcgcgaa gtctttatac cgaaaggttg    960
ggcaggccag cgtatcgtgc tgcgtttcga tgcggtcact cattacggca aagtgtgggt   1020
caataatcag gaagtgatgg agcatcaggg cggctatacg ccatttgaag ccgatgtcac   1080
gccgtatgtt attgccggga aaagtgtacg tatcaccgtt tgtgtgaaca acgaactgaa   1140
ctggcagact atcccgccgg gaatggtgat taccgacgaa aacggcaaga aaaagcagtc   1200
ttacttccat gatttcttta actatgccgg gatccatcgc agcgtaatgc tctacaccac   1260
gccgaacacc tgggtggacg atatcaccgt ggtgacgcat gtcgcgcaag actgtaacca   1320
cgcgtctgtt gactggcagg tggtggccaa tggtgatgtc agcgttgaac tgcgtgatgc   1380
ggatcaacag gtggttgcaa ctggacaagg cactagcggg actttgcaag tggtgaatcc   1440
gcacctctgg caaccgggtg aaggttatct ctatgaactg tgcgtcacag ccaaaagcca   1500
gacagagtgt gatatctacc cgcttcgcgt cggcatccgg tcagtggcag tgaagggcga   1560
acagttcctg attaaccaca aaccgttcta ctttactggc tttggtcgtc atgaagatgc   1620
ggacttacgt ggcaaaggat tcgataacgt gctgatggtg cacgaccacg cattaatgga   1680
ctggattggg gccaactcct accgtacctc gcattaccct tacgctgaag atgctcga    1740
ctgggcagat gaacatggca tcgtggtgat tgatgaaact gctgctgtcg gcttaacct   1800
ctctttaggc attggtttcg aagcgggcaa caagccgaaa gaactgtaca gcgaagaggc    1860
agtcaacggg gaaactcagc aagcgcactt acaggcgatt aaagagctga tagcgcgtga   1920
caaaaaccac ccaagcgtgg tgatgtggag tattgccaac gaaccggata cccgtccgca   1980
agtgcacggg aatatttcgc cactggcgga agcaacgcgt aaactcgacc cgacgcgtcc   2040
gatcacctgc gtcaatgtaa tgttctgcga cgctcacacc gataccatca gcgatctctt   2100
tgatgtgctg tgcctgaacc gttattacga tggtatgtc caaagcggcg atttggaaac   2160
ggcagagaag gtactggaaa aagaacttct ggcctggcag agaaactgc atcagccgat   2220
tatcatcacc gaatacggcg tggatacgtt agccgggctg cactcaatgt acaccgacat   2280
gtggagtgaa gagtatcagt gtgcatggct ggatatgtat caccgcgtct ttgatcgcgt   2340
cagcgccgtc gtcggtgaac aggtatggaa tttcgccgat tttgcgacct cgcaaggcat   2400
attgcgcgtt ggcggtaaca agaaagggat cttcactcgc gaccgcaaac cgaagtcggc   2460
ggctttttctg ctgcaaaaac gctggactgg catgaacttc ggtgaaaaac cgcagcaggg   2520
```

```
aggcaaacaa tgattaatta actagagcgg ccgccaccgc ggcccgagat tccggcctct   2580
tcggccgcca agcgacccgg gtggacgtct agaggtacct agcaattaac agatagtttg   2640
ccggtgataa ttctcttaac ctcccacact cctttgacat aacgatttat gtaacgaaac   2700
tgaaatttga ccagatattg tgtccgcggt ggagctccag cttttgttcc ctttagtgag   2760
ggttaatttc gagcttggcg taatcatggt catagctgtt tcctgtgtga aattgttatc   2820
cgctcacaat tccacacaac atacgagccg gaagcataaa gtgtaaagcc tggggtgcct   2880
aatgagtgag ctaactcaca ttaattgcgt tgcgctcact gcccgctttc cagtcgggaa   2940
acctgtcgtg ccagctgcat taatgaatcg gccaacgcgc ggggagaggc ggtttgcgta   3000
ttgggcgctc ttccgcttcc tcgctcactg actcgctgcg ctcggtcgtt cggctgcggc   3060
gagcggtatc agctcactca aaggcggtaa tacggttatc cacagaatca ggggataacg   3120
caggaaagaa catgtgagca aaaggccagc aaaaggccag gaaccgtaaa aaggccgcgt   3180
tgctggcgtt tttccatagg ctccgccccc ctgacgagca tcacaaaaat cgacgctcaa   3240
gtcagaggtg gcgaaacccg acaggactat aaagatacca ggcgtttccc cctggaagct   3300
ccctcgtgcg ctctcctgtt ccgaccctgc cgcttaccgg atacctgtcc gcctttctcc   3360
cttcgggaag cgtggcgctt tctcatagct cacgctgtag gtatctcagt tcggtgtagg   3420
tcgttcgctc caagctgggc tgtgtgcacg aaccccccgt tcagcccgac cgctgcgcct   3480
tatccggtaa ctatcgtctt gagtccaacc cggtaagaca cgacttatcg ccactggcag   3540
cagccactgg taacaggatt agcagagcga ggtatgtagg cggtgctaca gagttcttga   3600
agtggtggcc taactacggc tacactagaa ggacagtatt tggtatctgc gctctgctga   3660
agccagttac cttcggaaaa agagttggta gctcttgatc cggcaaacaa accaccgctg   3720
gtagcggtgg tttttttgtt tgcaagcagc agattacgcg cagaaaaaaa ggatctcaag   3780
aagatccttt gatcttttct acggggtctg acgctcagtg gaacgaaaac tcacgttaag   3840
ggattttggt catgagatta tcaaaaagga tcttcaccta gatcctttta aattaaaaat   3900
gaagttttaa atcaatctaa agtatatatg agtaaacttg gtctgacagt taccaatgct   3960
taatcagtga ggcacctatc tcagcgatct gtctatttcg ttcatccata gttgcctgac   4020
tccccgtcgt gtagataact acgatacggg agggcttacc atctggcccc agtgctgcaa   4080
tgataccgcg agacccacgc tcaccggctc cagatttatc agcaataaac cagccagccg   4140
gaagggccga gcgcagaagt ggtcctgcaa ctttatccgc ctccatccag tctattaatt   4200
gttgccggga agctagagta agtagttcgc cagttaatag tttgcgcaac gttgttgcca   4260
ttgctacagg catcgtggtg tcacgctcgt cgtttggtat ggcttcattc agctccggtt   4320
cccaacgatc aaggcgagtt acatgatccc ccatgttgtg caaaaaagcg gttagctcct   4380
tcggtcctcc gatcgttgtc agaagtaagt tggccgcagt gttatcactc atggttatgg   4440
cagcactgca taattctctt actgtcatgc catccgtaag atgcttttct gtgactggtg   4500
agtactcaac caagtcattc tgagaatagt gtatgcggcg accgagttgc tcttgcccgg   4560
cgtcaatacg ggataatacc gcgccacata gcagaacttt aaaagtgctc atcattggaa   4620
aacgttcttc ggggcgaaaa ctctcaagga tcttaccgct gttgagatcc agttcgatgt   4680
aacccactcg tgcacccaac tgatcttcag catcttttac tttcaccagc gtttctgggt   4740
gagcaaaaac aggaaggcaa aatgccgcaa aaaagggaat aagggcgaca cggaaatgtt   4800
gaatactcat actcttcctt tttcaatatt attgaagcat ttatcagggt tattgtctca   4860
tgagcggata catatttgaa tgtatttaga aaaataaaca aataggggtt ccgcgcacat   4920
```

```
ttccccgaaa agtgccacct gacgcgccct gtagcggcgc attaagcgcg gcgggtgtgg    4980
tggttacgcg cagcgtgacc gctacacttg ccagcgccct agcgcccgct cctttcgctt    5040
tcttcccttc ctttctcgcc acgttcgccg gctttccccg tcaagctcta aatcgggggc    5100 tcccttagg gttccgattt agtgctttac ggcacctcga ccccaaaaaa cttgattagg     5160
gtgatggttc acgtagtggg ccatcgccct gatagacggt ttttcgccct ttgacgttgg    5220
agtccacgtt ctttaatagt ggactcttgt tccaaactgg aacaacactc aaccctatct    5280
cggtctattc ttttgattta aagggatttt gccgatttc ggcctattgg ttaaaaaatg     5340
agctgattta acaaaaattt aacgcgaatt ttaacaaaat attaacgctt acaatttcca    5400
ttcgccattc aggctgcgca actgttggga agggcgatcg gtgcgggcct cttcgctatt    5460
acgccagctg gcgaaagggg gatgtgctgc aaggcgatta agttgggtaa cgccagggtt    5520
ttcccagtca cgacgttgta aaacgacggc cagtgaattg taatacgact cactataggg    5580
cgaattgggt accgggcccc cctcgaggt cgatggtgtc gataagcttg atatcgaatt     5640
catgtcacac aaaccgatct tcgcctcaag gaaacctaat tctacatccg agagactgcc    5700
gagatccagt ctacactgat taattttcgg gccaataatt taaaaaaatc gtgttatata    5760
atattatatg tattatatat atacatcatg atgatactga cagtcatgtc ccattgctaa    5820
atagacagac tccatctgcc gcctccaact gatgttctca atatttaagg ggtcatctcg    5880
cattgtttaa taataaacag actccatcta ccgcctccaa atgatgttct caaaatatat    5940
tgtatgaact tattttttatt acttagtatt attagacaac ttacttgctt tatgaaaaac    6000
acttcctatt taggaaacaa tttataatgg cagttcgttc atttaacaat ttatgtagaa    6060
taaatgttat aaatgcgtat gggaaatctt aaatatggat agcataaatg atatctgcat    6120
tgcctaattc gaaatcaaca gcaacgaaaa aaatcccttg tacaacataa atagtcatcg    6180
agaaatatca actatcaaag aacagctatt cacacgttac tattgagatt attattggac    6240
gagaatcaca cactcaactg tctttctctc ttctagaaat acaggtacaa gtatgtacta    6300
ttctcattgt tcatacttct agtcatttca tcccacatat tccttggatt tctctccaat    6360
gaatgacatt ctatcttgca aattcaacaa ttataataag atataccaaa gtagcggtat    6420
agtggcaatc aaaaagcttc tctggtgtgc ttctcgtatt tatttttatt ctaatgatcc    6480
attaaaggta tatatttatt tcttgttata taatcctttt gtttattaca tgggctggat    6540
acataaaggt attttgattt aatttttttgc ttaaattcaa tccccctcg ttcagtgtca     6600 actgtaatgg taggaaatta ccatactttt gaagaagcaa aaaaaatgaa agaaaaaaaa    6660
aatcgtattt ccaggttaga cgttccgcag aatctagaat gcggtatgcg gtacattgtt    6720
cttcgaacgt aaaagttgcg ctccctgaga tattgtacat ttttgctttt acaagtacaa    6780
gtacatcgta caactatgta ctactgttga tgcatccaca acagtttgtt ttgttttttt    6840
ttgttttttt tttttctaat gattcattac cgctatgtat acctacttgt acttgtagta    6900 agccggtta ttggcgttca attaatcata gacttatgaa tctgcacggt gtgcgctgcg     6960
agttactttt agcttatgca tgctacttgg gtgtaatatt gggatctgtt cggaaatcaa    7020
cggatgctca accgatttcg acagtaataa tttgaatcga atcggagcct aaaatgaacc    7080
cgagtatatc tcataaaatt ctcggtgaga ggtctgtgac tgtcagtaca aggtgccttc    7140
attatgccct caaccttacc atacctcact gaatgtagtg tacctctaaa atgaaatac     7200 agtgccaaaa gccaaggcac tgagctcgtc taacggactt gatatacaac caattaaaac    7260
aaatgaaaag aaatacagtt ctttgtatca tttgtaacaa ttaccctgta caaactaagg    7320
```

| | |
|---|---:|
| tattgaaatc ccacaatatt cccaaagtcc acccctttcc aaattgtcat gcctacaact | 7380 |
| catataccaa gcactaacct accaaacacc actaaaaccc cacaaaatat atcttaccga | 7440 |
| atatacagta acaagctacc accacactcg ttgggtgcag tcgccagctt aaagatatct | 7500 |
| atccacatca gccacaactc ccttccttta ataaaccgac tacacccttg gctattgagg | 7560 |
| ttatgagtga atatactgta gacaagacac tttcaagaag actgtttcca aaacgtacca | 7620 |
| ctgtcctcca ctacaaacac acccaatctg cttcttctag tcaaggttgc tacaccggta | 7680 |
| aattataaat catcatttca ttagcagggc agggcccttt ttatagagtc ttatacacta | 7740 |
| gcggaccctg ccggtagacc aacccgcagg cgcgtcagtt tgctccttcc atcaatgcgt | 7800 |
| cgtagaaacg acttactcct tcttgagcag ctccttgacc ttgttggcaa caagtctccg | 7860 |
| acctcggagg tggaggaaga gcctccgata tcggcggtag tgataccagc ctcgacggac | 7920 |
| tccttgacgg cagcctcaac agcgtcaccg gcgggcttca tgttaagaga aacttgagc | 7980 |
| atcatggcgg cagacagaat ggtggcaatg gggttgacct tctgcttgcc gagatcgggg | 8040 |
| gcagatccgt gacagggctc gtacagaccg aacgcctcgt tggtgtcggg cagagaagcc | 8100 |
| agagaggcgg agggcagcag acccagagaa ccggggatga cggaggcctc gtcggagatg | 8160 |
| atatcgccaa acatgttggt ggtgatgatg ataccattca tcttggaggg ctgcttgatg | 8220 |
| aggatcatgg cggccgagtc gatcagctgg tggttgagct cgagctgggg gaattcgtcc | 8280 |
| ttgaggactc gagtgacagt cttctcgccaa agtcgagagg aggccagcac gttggccttg | 8340 |
| tcaagagacc acacgggaag aggggggttg tgctgaaggg ccaggaaggc ggccattcgg | 8400 |
| gcaattcgct caacctcagg aacggagtag gtctcggtgt cggaagcgac gccagatccg | 8460 |
| tcatcctcct ttcgctctcc aaagtagata cctccgacga gctctcggac aatgatgaag | 8520 |
| tcggtgccct caacgtttcg gatggggag agatcggcga gcttgggcga cagcagctgg | 8580 |
| cagggtcgca ggttggcgta caggttcagg tcctttcgca gcttgaggag accctgctcg | 8640 |
| ggtcgcacgt cggttcgtcc gtcgggagtg gtccatacgg tgttggcagc gcctccgaca | 8700 |
| gcaccgagca taatagagtc agcctttcgg cagatgtcga gagtagcgtc ggtgatgggc | 8760 |
| tcgccctcct tctcaatggc agctcctcca atgagtcggt cctcaaacac aaactcggtg | 8820 |
| ccggaggcct cagcaacaga cttgagcacc ttgacggcct cggcaatcac ctcggggcca | 8880 |
| cagaagtcgc cgccgagaag aacaatcttc ttggagtcag tcttggtctt cttagtttcg | 8940 |
| ggttccattg tggatgtgtg tggttgtatg tgtgatgtgg tgtgtggagt gaaaatctgt | 9000 |
| ggctggcaaa cgctcttgta tatatacgca cttttgcccg tgctatgtgg aagactaaac | 9060 |
| ctccgaagat tgtgactcag gtagtgcggt atcggctagg gacccaaacc ttgtcgatgc | 9120 |
| cgatagcgct atcgaacgta ccccagccgg ccgggagtat gtcggagggg acatacgaga | 9180 |
| tcgtcaaggg tttgtggcca actggtaaat aaatgatgtc gacgtttatt ttcgagattt | 9240 |
| tacagatatt tctcgcagtt t | 9261 |

<210> SEQ ID NO 49
<211> LENGTH: 646
<212> TYPE: DNA
<213> ORGANISM: Yarrowia lipolytica

<400> SEQUENCE: 49

| | |
|---|---:|
| cacatgctgt gattagaaat aaagaaaaag gtgcttttttt ggcgctgtga ttaacatctc | 60 |
| gtctgccgtg ctctactagt cgcaatagca aaaactcgct taatagtgtg catagtgcgg | 120 |
| ggtagcagga tactgaacta cagtacgatt tgcttgctac tgcttgtagc aattaccttt | 180 |

```
actgtaggga ccacacctcc tggtttcaat gtctttcctc gcctcgacaa agcaaaactg    240
tcacccaatc acaccttgtt catattcatt agtgcatccg ttaaccttga catgacactt    300
ctcatactag tgatagggct gtagttgaga caagttgatt cacacggata catacaaagc    360
ctcagagagc aaatgttata tactcaggga ccgaccaatc aaaaaaacac actcctaata    420
accaccattt ccatctacgc gtactcactc tgtcagctgc cccacattgc caatgcaca     480 atgcacaatg atgtgtgcaa acaacgcaat caaaagtcta tggatgctga ccaaactctg    540
atcaccaagt tgcgaacatg aaaaagaaga cctgtgtata tataagtaag ggggagagcc    600
ctaactagat ctttcgaaaa ccccccgacc ttcaccttcc acaacc                   646

<210> SEQ ID NO 50
<211> LENGTH: 9124
<212> TYPE: DNA
<213> ORGANISM: Artificial Sequence
<220> FEATURE:
<223> OTHER INFORMATION: Plasmid

<400> SEQUENCE: 50
aaactacagt acgatttgct tgctactgct tgtagcaatt acctttactg tagggaccac     60
acctcctggt ttcaatgtct ttcctcgcct cgacaaagca aaactgtcac ccaatcacac    120
cttgttcata ttcattagtg catccgttaa ccttgacatg acacttctca tactagtgat    180
agggctgtag ttgagacaag ttgattcaca cggatacata caaagcctca gagagcaaat    240
gttatatact cagggaccga ccaatcaaaa aacacactc ctaataacca ccatttccat     300
ctacgcgtac tcactctgtc agctgcccca cattgcccaa tgcacaatgc acaatgatgt    360
gtgcaaacaa cgcaatcaaa agtctatgga tgctgaccaa actctgatca ccaagttgcg    420
aacatgaaaa agaagacctg tgtatatata agtaagggg agagccctaa ctagatcttt     480
cgaaaacccc ccgaccttca ccttccacaa ccatgatcat cttatacgtt ttggccgttg    540
cggtctcctt cctcatcttc aagagagtca cctacaccat ggcatggatg gtacgtcctg    600
tagaaacccc aacccgtgaa atcaaaaaac tcgacggcct gtgggcattc agtctggatc    660
gcgaaaactg tggaattgat cagcgttggt gggaaagcgc gttacaagaa agccgggcaa    720
ttgctgtgcc aggcagtttt aacgatcagt tcgccgatgc agatattcgt aattatgcgg    780
gcaacgtctg gtatcagcgc gaagtcttta taccgaaagg ttgggcaggc cagcgtatcg    840
tgctgcgttt cgatgcggtc actcattacg gcaaagtgtg gtcaataat caggaagtga     900 tggagcatca gggcggctat acgccatttg aagccgatgt cacgccgtat gttattgccg    960
ggaaaagtgt acgtatcacc gtttgtgtga caacgaact gaactggcag actatcccgc    1020
cgggaatggt gattaccgac gaaaacggca agaaaaagca gtcttacttc catgatttct    1080
ttaactatgc cgggatccat cgcagcgtaa tgctctacac cacgccgaac acctgggtgg    1140
acgatatcac cgtggtgacg catgtcgcgc aagactgtaa ccacgcgtct gttgactggc    1200
aggtggtggc caatggtgat gtcagcgttg aactgcgtga tgcggatcaa caggtggttg    1260
caactggaca aggcactagc gggactttgc aagtggtgaa tccgcacctc tggcaaccgg    1320
gtgaaggtta tctctatgaa ctgtgcgtca cagccaaaag ccagacagag tgtgatatct    1380
acccgcttcg cgtcggcatc cggtcagtgg cagtgaaggg cgaacagttc ctgattaacc    1440
acaaaccgtt ctactttact ggctttggtc gtcatgaaga tgcggactta cgtggcaaag    1500
gattcgataa cgtgctgatg gtgcacgacc acgcattaat ggactggatt ggggccaact    1560
cctaccgtac ctcgcattac ccttacgctg aagagatgct cgactgggca gatgaacatg    1620
```

```
gcatcgtggt gattgatgaa actgctgctg tcggctttaa cctctcttta ggcattggtt    1680
tcgaagcggg caacaagccg aaagaactgt acagcgaaga ggcagtcaac ggggaaactc    1740
agcaagcgca cttacaggcg attaaagagc tgatagcgcg tgacaaaaac cacccaagcg    1800
tggtgatgtg gagtattgcc aacgaaccgg atacccgtcc gcaagtgcac gggaatattt    1860
cgccactggc ggaagcaacg cgtaaactcg acccgacgcg tccgatcacc tgcgtcaatg    1920
taatgttctg cgacgctcac accgatacca tcagcgatct ctttgatgtg ctgtgcctga    1980
accgttatta cggatggtat gtccaaagcg gcgatttgga aacggcagag aaggtactgg    2040
aaaaagaact tctggcctgg caggagaaac tgcatcagcc gattatcatc accgaatacg    2100
gcgtggatac gttagccggg ctgcactcaa tgtacaccga catgtggagt gaagagtatc    2160
agtgtgcatg gctggatatg tatcaccgcg tctttgatcg cgtcagcgcc gtcgtcggtg    2220
aacaggtatg gaatttcgcc gattttgcga cctcgcaagg catattgcgc gttggcggta    2280
acaagaaagg gatcttcact cgcgaccgca aaccgaagtc ggcggctttt ctgctgcaaa    2340
aacgctggac tggcatgaac ttcggtgaaa accgcagca gggaggcaaa caatgattaa    2400
ttaactagag cggccgccac cgcggcccga gattccggcc tcttcggccg ccaagcgacc    2460
cgggtggacg tctagaggta cctagcaatt aacagatagt ttgccggtga taattctctt    2520
aacctcccac actcctttga cataacgatt tatgtaacga aactgaaatt tgaccagata    2580
ttgtgtccgc ggtggagctc cagcttttgt tccctttagt gagggttaat ttcgagcttg    2640
gcgtaatcat ggtcatagct gtttcctgtg tgaaattgtt atccgctcac aattccacac    2700
aacatacgag ccggaagcat aaagtgtaaa gcctggggtg cctaatgagt gagctaactc    2760
acattaattg cgttgcgctc actgcccgct ttccagtcgg gaaacctgtc gtgccagctg    2820
cattaatgaa tcggccaacg cgcggggaga ggcggtttgc gtattgggcg ctcttccgct    2880
tcctcgctca ctgactcgct gcgctcggtc gttcggctgc ggcgagcggt atcagctcac    2940
tcaaaggcgg taatacggtt atccacagaa tcaggggata acgcaggaaa gaacatgtga    3000
gcaaaaggcc agcaaaaggc caggaaccgt aaaaaggccg cgttgctggc gttttttccat   3060 aggctccgcc cccctgacga gcatcacaaa aatcgacgct caagtcagag gtggcgaaac    3120
ccgacaggac tataaagata ccaggcgttt cccctggaa gctccctcgt gcgctctcct    3180
gttccgaccc tgccgcttac cggatacctg tccgccttc tcccttcggg aagcgtggcg    3240
ctttctcata gctcacgctg taggtatctc agttcggtgt aggtcgttcg ctccaagctg    3300
ggctgtgtgc acgaaccccc cgttcagccc gaccgctgcg ccttatccgg taactatcgt    3360
cttgagtcca acccggtaag acacgactta tcgccactgg cagcagccac tggtaacagg    3420
attagcagag cgaggtatgt aggcggtgct acagagttct tgaagtggtg gcctaactac    3480
ggctacacta aaggacagt atttggtatc tgcgctctgc tgaagccagt taccttcgga    3540
aaaagagttg gtagctcttg atccggcaaa caaaccaccg ctggtagcgg tggtttttt     3600 gtttgcaagc agcagattac gcgcagaaaa aaaggatctc aagaagatcc tttgatcttt    3660
tctacggggt ctgacgctca gtggaacgaa aactcacgtt aagggatttt ggtcatgaga    3720
ttatcaaaaa ggatcttcac ctagatcctt ttaaattaaa aatgaagttt taaatcaatc    3780
taaagtatat atgagtaaac ttggtctgac agttaccaat gcttaatcag tgaggcacct    3840
atctcagcga tctgtctatt tcgttcatcc atagttgcct gactccccgt cgtgtagata    3900
actacgatac gggagggctt accatctggc cccagtgctg caatgatacc gcgagaccca    3960
cgctcaccgg ctccagattt atcagcaata aaccagccag ccggaagggc cgagcgcaga    4020
```

```
agtggtcctg caactttatc cgcctccatc cagtctatta attgttgccg ggaagctaga    4080
gtaagtagtt cgccagttaa tagtttgcgc aacgttgttg ccattgctac aggcatcgtg    4140
gtgtcacgct cgtcgtttgg tatggcttca ttcagctccg gttcccaacg atcaaggcga    4200
gttacatgat cccccatgtt gtgcaaaaaa gcggttagct ccttcggtcc tccgatcgtt    4260
gtcagaagta agttggccgc agtgttatca ctcatggtta tggcagcact gcataattct    4320
cttactgtca tgccatccgt aagatgcttt tctgtgactg gtgagtactc aaccaagtca    4380
ttctgagaat agtgtatgcg cgaccgagt tgctcttgcc cggcgtcaat acggataat     4440 accgcgccac atagcagaac tttaaaagtg ctcatcattg gaaaacgttc ttcggggcga    4500
aaactctcaa ggatcttacc gctgttgaga tccagttcga tgtaacccac tcgtgcaccc    4560
aactgatctt cagcatcttt tactttcacc agcgtttctg ggtgagcaaa aacaggaagg    4620
caaaatgccg caaaaaaggg aataaggggcg cacggaaat gttgaatact catactcttc     4680
ctttttcaat attattgaag catttatcag ggttattgtc tcatgagcgg atacatattt    4740
gaatgtattt agaaaaataa acaaataggg gttccgcgca catttccccg aaaagtgcca    4800
cctgacgcgc cctgtagcgg cgcattaagc gcggcgggtg tggtggttac gcgcagcgtg    4860
accgctacac ttgccagcgc cctagcgccc gctcctttcg cttcttccc ttcctttctc     4920 gccacgttcg ccggctttcc ccgtcaagct ctaaatcggg ggctcccttt agggttccga    4980
tttagtgctt tacggcacct cgaccccaaa aaacttgatt agggtgatgg ttcacgtagt    5040
gggccatcgc cctgatagac ggtttttcgc cctttgacgt tggagtccac gttctttaat    5100
agtggactct tgttccaaac tggaacaaca ctcaaccta tctcggtcta ttcttttgat     5160
ttataaggga ttttgccgat ttcggcctat tggttaaaaa atgagctgat ttaacaaaaa    5220
tttaacgcga attttaacaa atattaacg cttacaattt ccattcgcca ttcaggctgc     5280
gcaactgttg ggaagggcga tcggtgcggg cctcttcgct attacgccag ctggcgaaag    5340
ggggatgtgc tgcaaggcga ttaagttggg taacgccagg gttttcccag tcacgacgtt    5400
gtaaaacgac ggccagtgaa ttgtaatacg actcactata gggcgaattg ggtaccgggc    5460 ccccccctcga ggtcgatggt gtcgataagc ttgatatcga attcatgtca cacaaaccga    5520
tcttcgcctc aaggaaacct aattctacat ccgagagact gccgagatcc agtctacact    5580
gattaatttt cgggccaata atttaaaaaa atcgtgttat ataatattat atgtattata    5640
tatatacatc atgatgatac tgacagtcat gtcccattgc taaatagaca gactccatct    5700
gccgcctcca actgatgttc tcaatattta aggggtcatc tcgcattgtt taataataaa    5760
cagactccat ctaccgcctc caaatgatgt tctcaaaata tattgtatga acttattttt    5820
attacttagt attattagac aacttacttg ctttatgaaa aacacttcct atttaggaaa    5880
caatttataa tggcagttcg ttcatttaac aatttatgta gaataaatgt tataaatgcg    5940
tatgggaaat cttaaatatg gatagcataa atgatatctg cattgcctaa ttcgaaatca    6000
acagcaacga aaaaaatccc ttgtacaaca taaatagtca tcgagaaata tcaactatca    6060
aagaacagct attcacacgt tactattgag attattattg gacgagaatc acacactcaa    6120
ctgtctttct ctcttctaga aatacaggta caagtatgta ctattctcat tgttcatact    6180
tctagtcatt tcatcccaca tattccttgg atttctctcc aatgaatgac attctatctt    6240
gcaaattcaa caattataat aagatatacc aaagtagcgg tatagtggca atcaaaaagc    6300
ttctctggtg tgcttctcgt atttattttt attctaatga tccattaaag gtatatattt    6360
atttcttgtt atataatcct tttgtttatt acatgggctg gatacataaa ggtattttga    6420
```

-continued

```
tttaatttttt tgcttaaatt caatcccccc tcgttcagtg tcaactgtaa tggtaggaaa    6480
ttaccatact tttgaagaag caaaaaaaat gaaagaaaaa aaaaatcgta tttccaggtt    6540
agacgttccg cagaatctag aatgcggtat gcggtacatt gttcttcgaa cgtaaaagtt    6600
gcgctccctg agatattgta cattttttgct tttacaagta caagtacatc gtacaactat    6660
gtactactgt tgatgcatcc acaacagttt gttttgtttt ttttttgtttt ttttttttct    6720 aatgattcat taccgctatg tatacctact tgtacttgta gtaagccggg ttattggcgt    6780
tcaattaatc atagacttat gaatctgcac ggtgtgcgct gcgagttact tttagcttat    6840
gcatgctact tgggtgtaat attgggatct gttcggaaat caacggatgc tcaaccgatt    6900
tcgacagtaa taatttgaat cgaatcggag cctaaaatga acccgagtat atctcataaa    6960
attctcggtg agaggtctgt gactgtcagt acaaggtgcc ttcattatgc cctcaacctt    7020
accatacctc actgaatgta gtgtacctct aaaaatgaaa tacagtgcca aaagccaagg    7080
cactgagctc gtctaacgga cttgatatac aaccaattaa aacaaatgaa agaaataca    7140 gttctttgta tcatttgtaa caattacct gtacaaacta aggtattgaa atcccacaat    7200
attcccaaag tccacccctt tccaaattgt catgcctaca actcatatac caagcactaa    7260
cctaccaaac accactaaaa ccccacaaaa tatatcttac cgaatataca gtaacaagct    7320
accaccacac tcgttgggtg cagtcgccag cttaaagata tctatccaca tcagccacaa    7380
ctcccttcct ttaataaacc gactacaccc ttggctattg aggttatgag tgaatatact    7440
gtagacaaga cactttcaag aagactgttt ccaaaacgta ccactgtcct ccactacaaa    7500
cacacccaat ctgcttcttc tagtcaaggt tgctacaccg gtaaattata aatcatcatt    7560
tcattagcag ggcagggccc ttttttataga gtcttataca ctagcggacc ctgccggtag    7620
accaacccgc aggcgcgtca gtttgctcct tccatcaatg cgtcgtagaa acgacttact    7680
ccttcttgag cagctccttg accttgttgg caacaagtct ccgacctcgg aggtggagga    7740
agagcctccg atatcggcgg tagtgatacc agcctcgacg gactccttga cggcagcctc    7800
aacagcgtca ccggcgggct tcatgttaag agagaacttg agcatcatgg cggcagacag    7860
aatggtggca atggggttga ccttctgctt gccgagatcg ggggcagatc cgtgacaggg    7920
ctcgtacaga ccgaacgcct cgttggtgtc gggcagagaa gccagagagg cggagggcag    7980
cagacccaga gaaccgggga tgacggaggc ctcgtcggag atgatatcgc caaacatgtt    8040
ggtggtgatg atgataccat tcatcttgga gggctgcttg atgaggatca tggcggccga    8100
gtcgatcagc tggtggttga gctcgagctg ggggaattcg tccttgagga ctcgagtgac    8160
agtctttcgc caaagtcgag aggaggccag cacgttggcc ttgtcaagag accacacggg    8220
aagagggggg ttgtgctgaa gggccaggaa ggcggccatt cgggcaattc gctcaacctc    8280
aggaacggag taggtctcgg tgtcggaagc gacgccagat ccgtcatcct cctttcgctc    8340
tccaaagtag atacctccga cgagctctcg gacaatgatg aagtcggtgc cctcaacgtt    8400
tcggatgggg gagagatcgg cgagcttggg cgacagcagc tggcagggtc gcaggttggc    8460
gtacaggttc aggtccttc gcagcttgag gagaccctgc tcgggtcgca cgtcggttcg    8520
tccgtcggga gtggtccata cggtgttggc agcgcctccg acagcaccga gcataataga    8580
gtcagccttt cggcagatgt cgagagtagc gtcggtgatg ggctcgccct ccttctcaat    8640
ggcagctcct ccaatgagtc ggtcctcaaa cacaaactcg gtgccggagg cctcagcaac    8700
agacttgagc accttgacgg cctcggcaat cacctcgggg ccacagaagt cgccgccgag    8760
aagaacaatc ttcttggagt cagtcttggt cttcttagtt tcgggttcca ttgtggatgt    8820
```

```
gtgtggttgt atgtgtgatg tggtgtgtgg agtgaaaatc tgtggctggc aaacgctctt    8880
gtatatatac gcacttttgc ccgtgctatg tggaagacta aacctccgaa gattgtgact    8940
caggtagtgc ggtatcggct agggacccaa accttgtcga tgccgatagc gctatcgaac    9000
gtaccccagc cggccgggag tatgtcggag gggacatacg agatcgtcaa gggtttgtgg    9060
ccaactggta aataaatgat gtcgacgttt attttcgaga ttttacagat atttctcgca    9120
gttt                                                                 9124

<210> SEQ ID NO 51
<211> LENGTH: 511
<212> TYPE: DNA
<213> ORGANISM: Yarrowia lipolytica

<400> SEQUENCE: 51
aactacagta cgatttgctt gctactgctt gtagcaatta cctttactgt agggaccaca      60
cctcctggtt tcaatgtctt tcctcgcctc gacaaagcaa aactgtcacc caatcacacc     120
ttgttcatat tcattagtgc atccgttaac cttgacatga cacttctcat actagtgata     180
gggctgtagt tgagacaagt tgattcacac ggatacatac aaagcctcag agagcaaatg     240
ttatatactc agggaccgac caatcaaaaa aacacactcc taataaccac catttccatc     300
tacgcgtact cactctgtca gctgccccac attgcccaat gcacaatgca caatgatgtg     360
tgcaaacaac gcaatcaaaa gtctatggat gctgaccaaa ctctgatcac caagttgcga     420
acatgaaaaa aagacctgt gtatatataa gtaaggggga gagccctaac tagatctttc      480
gaaaaccccc cgaccttcac cttccacaac c                                    511

<210> SEQ ID NO 52
<211> LENGTH: 8977
<212> TYPE: DNA
<213> ORGANISM: Artificial Sequence
<220> FEATURE:
<223> OTHER INFORMATION: Plasmid

<400> SEQUENCE: 52
aaaccttgac atgacacttc tcatactagt gatagggctg tagttgagac aagttgattc      60
acacggatac atacaaagcc tcagagagca aatgttatat actcagggac cgaccaatca     120 aaaaacaca ctcctaataa ccaccatttc catctacgcg tactcactct gtcagctgcc      180
ccacattgcc caatgcacaa tgcacaatga tgtgtgcaaa caacgcaatc aaaagtctat     240
ggatgctgac caaactctga tcaccaagtt gcgaacatga aaagaagac ctgtgtatat      300 ataagtaagg gggagagccc taactagatc tttcgaaaac cccccgacct tcaccttcca     360
caaccatgat catcttatac gttttggccg ttgcggtctc cttcctcatc ttcaagagag     420
tcacctacac catggcatgg atggtacgtc ctgtagaaac cccaacccgt gaaatcaaaa     480
aactcgacgg cctgtgggca ttcagtctgg atcgcgaaaa ctgtggaatt gatcagcgtt     540
ggtgggaaag cgcgttacaa gaaagccggg caattgctgt gccaggcagt tttaacgatc     600
agttcgccga tgcagatatt cgtaattatg cgggcaacgt ctggtatcag cgcgaagtct     660
ttataccgaa aggttgggca ggccagcgta tcgtgctgcg tttcgatgcg gtcactcatt     720
acggcaaagt gtgggtcaat aatcaggaag tgatggagca tcagggcggc tatacgccat     780
ttgaagccga tgtcacgccg tatgttattg ccgggaaaag tgtacgtatc accgtttgtg     840
tgaacaacga actgaactgg cagactatcc cgccgggaat ggtgattacc gacgaaaacg     900
gcaagaaaaa gcagtcttac ttccatgatt tctttaacta tgccgggatc catcgcagcg     960
```

```
taatgctcta caccacgccg aacacctggg tggacgatat caccgtggtg acgcatgtcg    1020
cgcaagactg taaccacgcg tctgttgact ggcaggtggt ggccaatggt gatgtcagcg    1080
ttgaactgcg tgatgcggat caacaggtgg ttgcaactgg acaaggcact agcgggactt    1140
tgcaagtggt gaatccgcac ctctggcaac cgggtgaagg ttatctctat gaactgtgcg    1200
tcacagccaa aagccagaca gagtgtgata tctacccgct tcgcgtcggc atccggtcag    1260
tggcagtgaa gggcgaacag ttcctgatta accacaaacc gttctacttt actggctttg    1320
gtcgtcatga agatgcggac ttacgtggca aaggattcga taacgtgctg atggtgcacg    1380
accacgcatt aatggactgg attggggcca actcctaccg tacctcgcat taccttacg     1440 ctgaagagat gctcgactgg gcagatgaac atggcatcgt ggtgattgat gaaactgctg    1500
ctgtcggctt taacctctct ttaggcattg gtttcgaagc gggcaacaag ccgaaagaac    1560
tgtacagcga agaggcagtc aacggggaaa ctcagcaagc gcacttacag gcgattaaag    1620
agctgatagc gcgtgacaaa aaccacccaa gcgtggtgat gtggagtatt gccaacgaac    1680
cggatacccg tccgcaagtg cacgggaata tttcgccact ggcggaagca acgcgtaaac    1740
tcgacccgac gcgtccgatc acctgcgtca atgtaatgtt ctgcgacgct cacaccgata    1800
ccatcagcga tctctttgat gtgctgtgcc tgaaccgtta ttacggatgg tatgtccaaa    1860
gcggcgattt ggaaacggca gagaaggtac tggaaaaaga acttctggcc tggcaggaga    1920
aactgcatca gccgattatc atcaccgaat acggcgtgga tacgttagcc gggctgcact    1980
caatgtacac cgacatgtgg agtgaagagt atcagtgtgc atggctggat atgtatcacc    2040
gcgtctttga tcgcgtcagc gccgtcgtcg gtgaacaggt atggaatttc gccgattttg    2100
cgacctcgca aggcatattg cgcgttggcg gtaacaagaa agggatcttc actcgcgacc    2160
gcaaaccgaa gtcggcggct tttctgctgc aaaaacgctg gactggcatg aacttcggtg    2220
aaaaaccgca gcagggaggc aaacaatgat taattaacta gagcggccgc caccgcggcc    2280
cgagattccg gcctcttcgg ccgccaagcg acccgggtgg acgtctagag gtacctagca    2340
attaacagat agtttgccgg tgataattct cttaacctcc cacactcctt tgacataacg    2400
atttatgtaa cgaaactgaa atttgaccag atattgtgtc cgcggtggag ctccagcttt    2460
tgttcccttt agtgagggtt aatttcgagc ttggcgtaat catggtcata gctgtttcct    2520
gtgtgaaatt gttatccgct cacaattcca cacaacatac gagccggaag cataaagtgt    2580
aaagcctggg gtgcctaatg agtgagctaa ctcacattaa ttgcgttgcg ctcactgccc    2640
gctttccagt cgggaaacct gtcgtgccag ctgcattaat gaatcggcca acgcgcgggg    2700
agaggcggtt tgcgtattgg gcgctcttcc gcttcctcgc tcactgactc gctgcgctcg    2760
gtcgttcggc tgcggcgagc ggtatcagct cactcaaagg cggtaatacg gttatccaca    2820
gaatcagggg ataacgcagg aaagaacatg tgagcaaaag gccagcaaaa ggccaggaac    2880
cgtaaaaagg ccgcgttgct ggcgtttttc cataggctcc gcccccctga cgagcatcac    2940
aaaaatcgac gctcaagtca gaggtggcga aacccgacag gactataaag ataccaggcg    3000
tttccccctg gaagctccct cgtgcgctct cctgttccga ccctgccgct taccggatac    3060
ctgtccgcct ttctcccttc gggaagcgtg gcgctttctc atagctcacg ctgtaggtat    3120
ctcagttcgg tgtaggtcgt tcgctccaag ctgggctgtg tgcacgaacc cccgttcag    3180 cccgaccgct gcgccttatc cggtaactat cgtcttgagt ccaacccggt aagacacgac    3240
ttatcgccac tggcagcagc cactggtaac aggattagca gagcgaggta tgtaggcggt    3300
gctacagagt tcttgaagtg gtggcctaac tacggctaca ctagaaggac agtatttggt    3360
```

```
atctgcgctc tgctgaagcc agttaccttc ggaaaaagag ttggtagctc ttgatccggc   3420
aaacaaacca ccgctggtag cggtggtttt tttgtttgca agcagcagat tacgcgcaga   3480
aaaaaaggat ctcaagaaga tcctttgatc ttttctacgg ggtctgacgc tcagtggaac   3540
gaaaactcac gttaagggat tttggtcatg agattatcaa aaaggatctt cacctagatc   3600
cttttaaatt aaaaatgaag ttttaaatca atctaaagta tatatgagta aacttggtct   3660
gacagttacc aatgcttaat cagtgaggca cctatctcag cgatctgtct atttcgttca   3720
tccatagttg cctgactccc cgtcgtgtag ataactacga tacggagggc ttaccatct   3780 ggccccagtg ctgcaatgat accgcgagac ccacgctcac cggctccaga tttatcagca   3840
ataaaccagc cagccggaag ggccgagcgc agaagtggtc ctgcaacttt atccgcctcc   3900
atccagtcta ttaattgttg ccgggaagct agagtaagta gttcgccagt taatagtttg   3960
cgcaacgttg ttgccattgc tacaggcatc gtggtgtcac gctcgtcgtt tggtatggct   4020
tcattcagct ccggttccca acgatcaagg cgagttacat gatccccat gttgtgcaaa   4080 aaagcggtta gctccttcgg tcctccgatc gttgtcagaa gtaagttggc cgcagtgtta   4140
tcactcatgg ttatggcagc actgcataat tctcttactg tcatgccatc cgtaagatgc   4200
ttttctgtga ctggtgagta ctcaaccaag tcattctgag aatagtgtat gcggcgaccg   4260
agttgctctt gcccggcgtc aatacggat aataccgcgc cacatagcag aactttaaaa   4320
gtgctcatca ttggaaaacg ttcttcgggg cgaaaactct caaggatctt accgctgttg   4380
agatccagtt cgatgtaacc cactcgtgca cccaactgat cttcagcatc ttttactttc   4440
accagcgttt ctgggtgagc aaaaacagga aggcaaaatg ccgcaaaaaa gggaataagg   4500
gcgacacgga aatgttgaat actcatactc ttccttttc aatattattg aagcatttat   4560
cagggttatt gtctcatgag cggatacata tttgaatgta tttagaaaaa taaacaaata   4620
ggggttccgc gcacatttcc ccgaaaagtg ccacctgacg cgccctgtag cggcgcatta   4680
agcgcggcgg gtgtggtggt tacgcgcagc gtgaccgcta cacttgccag cgccctagcg   4740
cccgctcctt tcgctttctt cccttccttt ctcgccacgt tcgccggctt tccccgtcaa   4800
gctctaaatc gggggctccc tttagggttc cgatttagtg ctttacggca cctcgacccc   4860
aaaaaacttg attagggtga tggttcacgt agtgggccat cgccctgata gacggttttt   4920
cgccctttga cgttggagtc acgttctttt aatagtggac tcttgttcca aactggaaca   4980
acactcaacc ctatctcggt ctattctttt gatttataag ggattttgcc gatttcggcc   5040
tattggttaa aaaatgagct gatttaacaa aaatttaacg cgaattttaa caaaatatta   5100
acgcttacaa tttccattcg ccattcaggc tgcgcaactg ttgggaaggg cgatcggtgc   5160
gggcctcttc gctattacgc cagctggcga aggggggatg tgctgcaagg cgattaagtt   5220
gggtaacgcc agggttttcc cagtcacgac gttgtaaaac gacggccagt gaattgtaat   5280
acgactcact atagggcgaa ttgggtaccg ggccccccct cgaggtcgat ggtgtcgata   5340
agcttgatat cgaattcatg tcacacaaac cgatcttcgc ctcaaggaaa cctaattcta   5400
catccgagag actgccgaga tccagtctac actgattaat tttcgggcca ataatttaaa   5460
aaaatcgtgt tatataatat tatatgtatt atatatatac atcatgatga tactgacagt   5520
catgtcccat tgctaaatag acagactcca tctgccgcct ccaactgatg ttctcaatat   5580
ttaaggggtc atctcgcatt gtttaataat aaacagactc catctaccgc ctccaaatga   5640
tgttctcaaa atatattgta tgaacttatt tttattactt agtattatta gacaacttac   5700
ttgctttatg aaaaacactt cctatttagg aaacaattta taatggcagt tcgttcattt   5760
```

```
aacaatttat gtagaataaa tgttataaat gcgtatggga aatcttaaat atggatagca    5820
taaatgatat ctgcattgcc taattcgaaa tcaacagcaa cgaaaaaaat cccttgtaca    5880
acataaatag tcatcgagaa atatcaacta tcaaagaaca gctattcaca cgttactatt    5940
gagattatta ttggacgaga atcacacact caactgtctt tctctcttct agaaatacag    6000
gtacaagtat gtactattct cattgttcat acttctagtc atttcatccc acatattcct    6060
tggatttctc tccaatgaat gacattctat cttgcaaatt caacaattat aataagatat    6120
accaaagtag cggtatagtg gcaatcaaaa agcttctctg gtgtgcttct cgtatttatt    6180
tttattctaa tgatccatta aaggtatata tttatttctt gttatataat cctttgttt     6240 attacatggg ctggatacat aaaggtattt tgatttaatt ttttgcttaa attcaatccc    6300
ccctcgttca gtgtcaactg taatggtagg aaattaccat acttttgaag aagcaaaaaa    6360
aatgaaagaa aaaaaaaatc gtatttccag gttagacgtt ccgcagaatc tagaatgcgg    6420
tatgcggtac attgttcttc gaacgtaaaa gttgcgctcc ctgagatatt gtacattttt    6480
gcttttacaa gtacaagtac atcgtacaac tatgtactac tgttgatgca tccacaacag    6540
tttgttttgt tttttttgt tttttttttt tctaatgatt cattaccgct atgtatacct      6600
acttgtactt gtagtaagcc gggttattgg cgttcaatta atcatagact tatgaatctg    6660
cacggtgtgc gctgcgagtt acttttagct tatgcatgct acttgggtgt aatattggga    6720
tctgttcgga aatcaacgga tgctcaaccg atttcgacag taataatttg aatcgaatcg    6780
gagcctaaaa tgaacccgag tatatctcat aaaattctcg gtgagaggtc tgtgactgtc    6840
agtacaaggt gccttcatta tgccctcaac cttaccatac ctcactgaat gtagtgtacc    6900
tctaaaaatg aaatacagtg ccaaaagcca aggcactgag ctcgtctaac ggacttgata    6960
tacaaccaat taaaacaaat gaaagaaat acagttcttt gtatcatttg taacaattac       7020
cctgtacaaa ctaaggtatt gaatcccac aatattccca aagtccaccc ctttccaaat       7080
tgtcatgcct acaactcata taccaagcac taacctacca aacaccacta aaaccccaca    7140
aaatatatct taccgaatat acagtaacaa gctaccacca cactcgttgg gtgcagtcgc    7200
cagcttaaag atatctatcc acatcagcca caactccctt cctttaataa accgactaca    7260
cccttggcta ttgaggttat gagtgaatat actgtagaca agacactttc aagaagactg    7320
tttccaaaac gtaccactgt cctccactac aaacacaccc aatctgcttc ttctagtcaa    7380
ggttgctaca ccgtaaaatt ataaatcatc atttcattag cagggcaggg ccctttttat    7440
agagtcttat acactagcgg accctgccgg tagaccaacc cgcaggcgcg tcagtttgct    7500
ccttccatca atgcgtcgta gaaacgactt actccttctt gagcagctcc ttgaccttgt    7560
tggcaacaag tctccgacct cggaggtgga ggaagagcct ccgatatcgg cggtagtgat    7620
accagcctcg acggactcct tgacggcagc ctcaacagcg tcaccggcgg gcttcatgtt    7680
aagagagaac ttgagcatca tggcggcaga cagaatggtg gcaatggggt tgaccttctg    7740
cttgccgaga tcgggggcag atccgtgaca gggctcgtac agaccgaacg cctcgttggt    7800
gtcgggcaga gaagccagag aggcggaggg cagcagaccc agaaccgg ggatgacgga      7860 ggcctcgtcg gagatgatat cgccaaacat gttggtggtg atgatgatac cattcatctt    7920
ggagggctgc ttgatgagga tcatggcggc cgagtcgatc agctggtggt tgagctcgag    7980
ctgggggaat tcgtccttga ggactcgagt gacagtcttt cgccaaagtc gagaggaggc    8040
cagcacgttg gccttgtcaa gagaccacac gggaagaggg gggttgtgct gaagggccag    8100
gaaggcggcc attcgggcaa ttcgctcaac ctcaggaacg gagtaggtct cggtgtcgga    8160
```

```
agcgacgcca gatccgtcat cctcctttcg ctctccaaag tagatacctc cgacgagctc    8220
tcggacaatg atgaagtcgg tgccctcaac gtttcggatg ggggagagat cggcgagctt    8280
gggcgacagc agctggcagg gtcgcaggtt ggcgtacagg ttcagtcct ttcgcagctt     8340 gaggagaccc tgctcgggtc gcacgtcggt tcgtccgtcg ggagtggtcc atacggtgtt    8400
ggcagcgcct ccgacagcac cgagcataat agagtcagcc tttcggcaga tgtcgagagt    8460
agcgtcggtg atgggctcgc cctccttctc aatggcagct cctccaatga gtcggtcctc    8520
aaacacaaac tcggtgccgg aggcctcagc aacagacttg agcacttga cggcctcggc     8580 aatcacctcg gggccacaga gtcgccgcc gagaagaaca atcttcttgg agtcagtctt     8640
ggtcttctta gtttcgggtt ccattgtgga tgtgtgtggt tgtatgtgtg atgtggtgtg    8700
tggagtgaaa atctgtggct ggcaaacgct cttgtatata tacgcacttt tgcccgtgct    8760
atgtggaaga ctaaacctcc gaagattgtg actcaggtag tgcggtatcg gctagggacc    8820
caaaccttgt cgatgccgat agcgctatcg aacgtacccc agccggccgg gagtatgtcg    8880
gaggggacat acgagatcgt caagggtttg tggccaactg gtaaataaat gatgtcgacg    8940
tttattttcg agattttaca gatatttctc gcagttt                            8977
```

```
<210> SEQ ID NO 53
<211> LENGTH: 364
<212> TYPE: DNA
<213> ORGANISM: Yarrowia lipolytica

<400> SEQUENCE: 53
aaccttgaca tgacacttct catactagtg atagggctgt agttgagaca agttgattca      60
cacggataca tacaaagcct cagagagcaa atgttatata ctcagggacc gaccaatcaa     120
aaaaacacac tcctaataac caccatttcc atctacgcgt actcactctg tcagctgccc     180
cacattgccc aatgcacaat gcacaatgat gtgtgcaaac aacgcaatca aaagtctatg     240
gatgctgacc aaactctgat caccaagttg cgaacatgaa aaagaagacc tgtgtatata     300
taagtaaggg ggagagccct aactagatct ttcgaaaacc ccccgacctt caccttccac     360
aacc                                                                 364
```

```
<210> SEQ ID NO 54
<211> LENGTH: 8854
<212> TYPE: DNA
<213> ORGANISM: Artificial Sequence
<220> FEATURE:
<223> OTHER INFORMATION: Plasmid

<400> SEQUENCE: 54
aaacacactc ctaataacca ccatttccat ctacgcgtac tcactctgtc agctgcccca      60
cattgcccaa tgcacaatgc acaatgatgt gtgcaaacaa cgcaatcaaa agtctatgga     120
tgctgaccaa actctgatca ccaagttgcg aacatgaaaa agaagacctg tgtatatata     180
agtaaggggg agagccctaa ctagatcttt cgaaaacccc ccgaccttca ccttccacaa     240
ccatgatcat cttatacgtt ttggccgttg cggtctcctt cctcatcttc aagagagtca     300
cctacaccat ggcatggatg gtacgtcctg tagaaacccc aacccgtgaa atcaaaaaac     360
tcgacggcct gtgggcattc agtctggatc gcgaaaactg tggaattgat cagcgttggt     420
gggaaagcgc gttacaagaa agccgggcaa ttgctgtgcc aggcagtttt aacgatcagt     480
tcgccgatga gatattcgt aattatgcgg gcaacgtctg gtatcagcgc gaagtcttta     540
taccgaaagg ttgggcaggc cagcgtatcg tgctgcgttt cgatgcggtc actcattacg     600
```

```
gcaaagtgtg ggtcaataat caggaagtga tggagcatca gggcggctat acgccatttg    660
aagccgatgt cacgccgtat gttattgccg ggaaaagtgt acgtatcacc gtttgtgtga    720
acaacgaact gaactggcag actatcccgc cgggaatggt gattaccgac gaaaacggca    780
agaaaaagca gtcttacttc catgatttct ttaactatgc cgggatccat cgcagcgtaa    840
tgctctacac cacgccgaac acctgggtgg acgatatcac cgtggtgacg catgtcgcgc    900
aagactgtaa ccacgcgtct gttgactggc aggtggtggc caatggtgat gtcagcgttg    960
aactgcgtga tgcggatcaa caggtggttg caactggaca aggcactagc gggactttgc   1020
aagtggtgaa tccgcacctc tggcaaccgg gtgaaggtta tctctatgaa ctgtgcgtca   1080
cagccaaaag ccagacagag tgtgatatct acccgcttcg cgtcggcatc cggtcagtgg   1140
cagtgaaggg cgaacagttc ctgattaacc acaaaccgtt ctactttact ggctttggtc   1200
gtcatgaaga tgcggactta cgtggcaaag gattcgataa cgtgctgatg gtgcacgacc   1260
acgcattaat ggactggatt ggggccaact cctaccgtac ctcgcattac ccttacgctg   1320
aagagatgct cgactgggca gatgaacatg gcatcgtggt gattgatgaa actgctgctg   1380
tcggctttaa cctctcttta ggcattggtt tcgaagcggg caacaagccg aaagaactgt   1440
acagcgaaga ggcagtcaac ggggaaactc agcaagcgca cttacaggcg attaagagc    1500
tgatagcgcg tgacaaaaac cacccaagcg tggtgatgtg gagtattgcc aacgaaccgg   1560
ataccegtcc gcaagtgcac gggaatattt cgccactggc ggaagcaacg cgtaaactcg   1620
acccgacgcg tccgatcacc tgcgtcaatg taatgttctg cgacgctcac accgatacca   1680
tcagcgatct ctttgatgtg ctgtgcctga accgttatta cggatggtat gtccaaagcg   1740
gcgatttgga acggcagag aaggtactgg aaaaagaact tctggcctgg caggagaaac   1800
tgcatcagcc gattatcatc accgaatacg gcgtggatac gttagccggg ctgcactcaa   1860
tgtacaccga catgtggagt gaagagtatc agtgtgcatg gctggatatg tatcaccgcg   1920
tctttgatcg cgtcagcgcc gtcgtcggtg aacaggtatg gaatttcgcc gattttgcga   1980
cctcgcaagg catattgcgc gttggcggta caagaaagg gatcttcact cgcgaccgca   2040
aaccgaagtc ggcggctttt ctgctgcaaa aacgctggac tggcatgaac ttcggtgaaa   2100
aaccgcagca gggaggcaaa caatgattaa ttaactagag cggccgccac cgcggcccga   2160
gattccggcc tcttcggccg ccaagcgacc cgggtggacg tctagaggta cctagcaatt   2220
aacagatagt ttgccggtga taattctctt aacctccac actcctttga cataacgatt    2280
tatgtaacga aactgaaatt tgaccagata ttgtgtccgc ggtggagctc cagcttttgt   2340
tccctttagt gagggttaat ttcgagcttg gcgtaatcat ggtcatagct gtttcctgtg   2400
tgaaattgtt atccgctcac aattccacac aacatacgag ccggaagcat aaagtgtaaa   2460
gcctggggtg cctaatgagt gagctaactc acattaattg cgttgcgctc actgcccgct   2520
ttccagtcgg gaaacctgtc gtgccagctg cattaatgaa tcggccaacg cgcggggaga   2580
ggcggtttgc gtattgggcg ctcttccgct tcctcgctca ctgactcgct gcgctcggtc   2640
gttcggctgc ggcgagcggt atcagctcac tcaaaggcgg taatacggtt atccacagaa   2700
tcaggggata acgcaggaaa gaacatgtga gcaaaaggcc agcaaaaggc caggaaccgt   2760
aaaaaggccg cgttgctggc gtttttccat aggctccgcc cccctgacga gcatcacaaa   2820
aatcgacgct caagtcagag gtggcgaaac ccgacaggac tataaagata ccaggcgttt   2880
ccccctggaa gctccctcgt gcgctctcct gttccgaccc tgccgcttac cggatacctg   2940
tccgcctttc tcccttcggg aagcgtggcg ctttctcata gctcacgctg taggtatctc   3000
```

```
agttcggtgt aggtcgttcg ctccaagctg ggctgtgtgc acgaacccc cgttcagccc    3060 gaccgctgcg ccttatccgg taactatcgt cttgagtcca acccgtaag acacgactta    3120 tcgccactgg cagcagccac tggtaacagg attagcagag cgaggtatgt aggcggtgct    3180
acagagttct tgaagtggtg gcctaactac ggctacacta aaggacagt atttggtatc     3240 tgcgctctgc tgaagccagt taccttcgga aaaagagttg gtagctcttg atccggcaaa    3300
caaaccaccg ctggtagcgg tggtttttt gtttgcaagc agcagattac gcgcagaaaa     3360
aaaggatctc aagaagatcc tttgatcttt tctacggggt ctgacgctca gtggaacgaa    3420
aactcacgtt aagggatttt ggtcatgaga ttatcaaaaa ggatcttcac ctagatcctt    3480
ttaaattaaa aatgaagttt taaatcaatc taaagtatat atgagtaaac ttggtctgac    3540
agttaccaat gcttaatcag tgaggcacct atctcagcga tctgtctatt tcgttcatcc    3600
atagttgcct gactcccgt cgtgtagata actacgatac ggggagggctt accatctggc     3660 cccagtgctg caatgatacc gcgagaccca cgctcaccgg ctccagattt atcagcaata    3720
aaccagccag ccggaagggc cgagcgcaga agtggtcctg caactttatc cgcctccatc    3780
cagtctatta attgttgccg ggaagctaga gtaagtagtt cgccagttaa tagtttgcgc    3840
aacgttgttg ccattgctac aggcatcgtg gtgtcacgct cgtcgtttgg tatggcttca    3900
ttcagctccg gttcccaacg atcaaggcga gttacatgat cccccatgtt gtgcaaaaaa    3960
gcggttagct ccttcggtcc tccgatcgtt gtcagaagta agttggccgc agtgttatca    4020
ctcatggtta tggcagcact gcataattct cttactgtca tgccatccgt aagatgcttt    4080
tctgtgactg gtgagtactc aaccaagtca ttctgagaat agtgtatgcg gcgaccgagt    4140
tgctcttgcc cggcgtcaat acgggataat accgcgccac atagcagaac tttaaaagtg    4200
ctcatcattg gaaaacgttc ttcggggcga aaactctcaa ggatcttacc gctgttgaga    4260
tccagttcga tgtaacccac tcgtgcaccc aactgatctt cagcatcttt tactttcacc    4320
agcgtttctg ggtgagcaaa aacaggaagg caaaatgccg caaaaaaggg aataagggcg    4380
acacggaaat gttgaatact catactcttc cttttcaat attattgaag catttatcag     4440
ggttattgtc tcatgagcgg atacatattt gaatgtattt agaaaaataa acaaataggg    4500
gttccgcgca catttccccg aaaagtgcca cctgacgcgc cctgtagcgg cgcattaagc    4560
gcggcgggtg tggtggttac gcgcagcgtg accgctacac ttgccagcgc cctagcgccc    4620
gctcctttcg ctttcttccc ttcctttctc gccacgttcg ccggctttcc ccgtcaagct    4680
ctaaatcggg ggctcccttt agggttccga tttagtgctt tacggcacct cgaccccaaa    4740
aaacttgatt agggtgatgg ttcacgtagt gggccatcgc cctgatagac ggtttttcgc    4800
cctttgacgt tggagtccac gttctttaat agtggactct tgttccaaac tggaacaaca    4860
ctcaacccta tctcggtcta ttcttttgat ttataaggga ttttgccgat ttcggcctat    4920
tggttaaaaa atgagctgat ttaacaaaaa tttaacgcga attttaacaa atattaacg     4980 cttacaattt ccattcgcca ttcaggctgc gcaactgttg ggaagggcga tcggtgcggg    5040
cctcttcgct attacgccag ctggcgaaag ggggatgtgc tgcaaggcga ttaagttggg    5100
taacgccagg gttttcccag tcacgacgtt gtaaaacgac ggccagtgaa ttgtaatacg    5160
actcactata gggcgaattg ggtaccgggc ccccctcga ggtcgatggt gtcgataagc     5220
ttgatatcga attcatgtca cacaaaccga tcttcgcctc aaggaaacct aattctacat    5280
ccgagagact gccgagatcc agtctacact gattaatttt cgggccaata atttaaaaaa    5340
atcgtgttat ataatattat atgtattata tatatacatc atgatgatac tgacagtcat    5400
```

```
gtcccattgc taaatagaca gactccatct gccgcctcca actgatgttc tcaatattta    5460
aggggtcatc tcgcattgtt taataataaa cagactccat ctaccgcctc caaatgatgt    5520
tctcaaaata tattgtatga acttatttt attacttagt attattagac aacttacttg    5580
ctttatgaaa aacacttcct atttaggaaa caatttataa tggcagttcg ttcatttaac    5640
aatttatgta gaataaatgt tataaatgcg tatgggaaat cttaaatatg gatagcataa    5700
atgatatctg cattgcctaa ttcgaaatca acagcaacga aaaaaatccc ttgtacaaca    5760
taaatagtca tcgagaaata tcaactatca aagaacagct attcacacgt tactattgag    5820
attattattg gacgagaatc acacactcaa ctgtctttct ctcttctaga aatacaggta    5880
caagtatgta ctattctcat tgttcatact tctagtcatt tcatcccaca tattccttgg    5940
atttctctcc aatgaatgac attctatctt gcaaattcaa caattataat aagatatacc    6000
aaagtagcgg tatagtggca atcaaaaagc ttctctggtg tgcttctcgt atttattttt    6060
attctaatga tccattaaag gtatatattt atttcttgtt atataatcct tttgtttatt    6120
acatgggctg gatacataaa ggtattttga tttaattttt tgcttaaatt caatcccccc    6180
tcgttcagtg tcaactgtaa tggtaggaaa ttaccatact tttgaagaag caaaaaaaat    6240
gaaagaaaaa aaaaatcgta tttccaggtt agacgttccg cagaatctag aatgcggtat    6300
gcggtacatt gttcttcgaa cgtaaaagtt gcgctccctg agatattgta cattttgct    6360 tttacaagta caagtacatc gtacaactat gtactactgt tgatgcatcc acaacagttt    6420
gttttgtttt tttttgtttt tttttttct aatgattcat taccgctatg tatacctact    6480
tgtacttgta gtaagccggg ttattggcgt tcaattaatc atagacttat gaatctgcac    6540
ggtgtgcgct gcgagttact tttagcttat gcatgctact tgggtgtaat attgggatct    6600
gttcggaaat caacggatgc tcaaccgatt tcgacagtaa taatttgaat cgaatcggag    6660
cctaaaatga acccgagtat atctcataaa attctcggtg agaggtctgt gactgtcagt    6720
acaaggtgcc ttcattatgc cctcaacctt accatacctc actgaatgta gtgtacctct    6780
aaaaatgaaa tacagtgcca aaagccaagg cactgagctc gtctaacgga cttgatatac    6840
aaccaattaa aacaaatgaa aagaaataca gttctttgta tcatttgtaa caattaccct    6900
gtacaaacta aggtattgaa atcccacaat attcccaaag tccaccccct tccaaattgt    6960
catgcctaca actcatatac caagcactaa cctaccaaac accactaaaa ccccacaaaa    7020
tatatcttac cgaatataca gtaacaagct accaccacac tcgttgggtg cagtcgccag    7080
cttaaagata tctatccaca tcagccacaa ctccctccct taataaaacc gactacaccc    7140
ttggctattg aggttatgag tgaatatact gtagacaaga cactttcaag aagactgttt    7200
ccaaaacgta ccactgtcct ccactacaaa cacacccaat ctgcttcttc tagtcaaggt    7260
tgctacaccg gtaaattata aatcatcatt tcattagcag ggcagggccc ttttataga    7320 gtcttataca ctagcggacc ctgccggtag accaacccgc aggcgcgtca gtttgctcct    7380
tccatcaatg cgtcgtagaa acgacttact ccttcttgag cagctccttg accttgttgg    7440
caacaagtct ccgacctcgg aggtggagga agagcctccg atatcggcgg tagtgatacc    7500
agcctcgacg gactccttga cggcagcctc aacagcgtca ccggcgggct tcatgttaag    7560
agagaacttg agcatcatgg cggcagacag aatggtggca atgggttga ccttctgctt    7620 gccgagatcg ggggcagatc cgtgacaggg ctcgtacaga ccgaacgcct cgttggtgtc    7680
gggcagagaa gccagagagg cggagggcag cagacccaga gaaccgggga tgacggaggc    7740
ctcgtcggag atgatatcgc caaacatgtt ggtggtgatg atgataccat tcatcttgga    7800
```

```
gggctgcttg atgaggatca tggcggccga gtcgatcagc tggtggttga gctcgagctg    7860
ggggaattcg tccttgagga ctcgagtgac agtctttcgc aaagtcgag aggaggccag     7920 cacgttggcc ttgtcaagag accacacggg aagaggggg ttgtgctgaa gggccaggaa     7980
ggcggccatt cgggcaattc gctcaacctc aggaacggag taggtctcgg tgtcggaagc    8040
gacgccagat ccgtcatcct cctttcgctc tccaaagtag atacctccga cgagctctcg    8100
gacaatgatg aagtcggtgc cctcaacgtt tcggatgggg gagagatcgg cgagcttggg    8160
cgacagcagc tggcagggtc gcaggttggc gtacaggttc aggtcctttc gcagcttgag    8220
gagaccctgc tcgggtcgca cgtcggttcg tccgtcggga gtggtccata cggtgttggc    8280
agcgcctccg acagcaccga gcataataga gtcagccttt cggcagatgt cgagagtagc    8340
gtcggtgatg ggctcgccct ccttctcaat ggcagctcct ccaatgagtc ggtcctcaaa    8400
cacaaactcg gtgccggagg cctcagcaac agacttgagc accttgacgg cctcggcaat    8460
cacctcgggg ccacagaagt cgccgccgag aagaacaatc ttcttggagt cagtcttggt    8520
cttcttagtt tcgggttcca ttgtggatgt gtgtggttgt atgtgtgatg tggtgtgtgg    8580
agtgaaaatc tgtggctggc aaacgctctt gtatatatac gcacttttgc ccgtgctatg    8640
tggaagacta aacctccgaa gattgtgact caggtagtgc ggtatcggct agggacccaa    8700
accttgtcga tgccgatagc gctatcgaac gtaccccagc cggccgggag tatgtcggag    8760
gggacatacg agatcgtcaa gggtttgtgg ccaactggta aataaatgat gtcgacgttt    8820
attttcgaga ttttacagat atttctcgca gttt                                8854

<210> SEQ ID NO 55
<211> LENGTH: 242
<212> TYPE: DNA
<213> ORGANISM: Yarrowia lipolytica

<400> SEQUENCE: 55
aaacacactc ctaataacca ccatttccat ctacgcgtac tcactctgtc agctgcccca     60
cattgcccaa tgcacaatgc acaatgatgt gtgcaaacaa cgcaatcaaa agtctatgga    120
tgctgaccaa actctgatca ccaagttgcg aacatgaaaa agaagacctg tgtatatata    180
agtaaggggg agagccctaa ctagatcttt cgaaaacccc ccgaccttca ccttccacaa    240
cc                                                                   242

<210> SEQ ID NO 56
<211> LENGTH: 68
<212> TYPE: DNA
<213> ORGANISM: Yarrowia lipolytica

<400> SEQUENCE: 56
tatataagta aggggagag ccctaactag atctttcgaa aaccccccga ccttcacctt      60
ccacaacc                                                              68

<210> SEQ ID NO 57
<211> LENGTH: 147
<212> TYPE: DNA
<213> ORGANISM: Yarrowia lipolytica

<400> SEQUENCE: 57
aactacagta cgatttgctt gctactgctt gtagcaatta cctttactgt agggaccaca     60
cctcctggtt tcaatgtctt tcctcgcctc gacaaagcaa aactgtcacc caatcacacc    120
ttgttcatat tcattagtgc atccgtt                                        147
```

```
<210> SEQ ID NO 58
<211> LENGTH: 18
<212> TYPE: DNA
<213> ORGANISM: Saccharomyces cerevisiae
<220> FEATURE:
<221> NAME/KEY: misc_feature
<222> LOCATION: (1)..(18)
<223> OTHER INFORMATION: Consensus sequence located in promoter
      sequences of S. cerevisiae genes
<220> FEATURE:
<221> NAME/KEY: misc_feature
<222> LOCATION: (2)..(6)
<223> OTHER INFORMATION: Adenine-rich (see Zhang, Z., and Dietrich,
      F. S., Nucleic Acids Res., 33:2838-2851 (2005))
<220> FEATURE:
<221> NAME/KEY: misc_feature
<222> LOCATION: (8)..(8)
<223> OTHER INFORMATION: y is t or c
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (13)..(18)
<223> OTHER INFORMATION: Adenine-rich (see Zhang, Z., and Dietrich,
      F. S., Nucleic Acids Res., 33:2838-2851 (2005))

<400> SEQUENCE: 58
annnnnnyaw nnnnnnnn                                               18
```

YARROWIA N-ALKANE-HYDROXYLATING CYTOCHROME P450 PROMOTER REGIONS FOR GENE EXPRESSION IN YEAST

This application claims the benefit of U.S. Provisional Application No. 61/471,736, filed Apr. 5, 2011, which is incorporated herein by reference in its entirety.

FIELD OF THE INVENTION

This invention is in the field of biotechnology. More specifically, this invention pertains to n-alkane-hydroxylating cytochrome P450 ["ALK2"] promoter regions derived from *Yarrowia lipolytica* that are useful for gene expression in yeast.

BACKGROUND OF THE INVENTION

Oleaginous yeast are defined as those organisms that are naturally capable of oil synthesis and accumulation, wherein oil accumulation ranges from at least about 25% up to about 80% of the dry cell weight. The technology for growing oleaginous yeast with high oil content is well developed (for example, see EP 0 005 277B1; Ratledge, C., *Prog. Ind. Microbiol.*, 16:119-206 (1982)).

And, these organisms have been commercially used for a variety of purposes in the past.

Recently, the natural abilities of oleaginous yeast have been enhanced by advances in genetic engineering, resulting in organisms capable of producing polyunsaturated fatty acids ["PUFAs"], carotenoids, resveratrol and sterols. For example, significant efforts by Applicants' Assignee have demonstrated that *Yarrowia lipolytica* can be engineered for production of omega-3 and omega-6 fatty acids, by introducing and expressing genes encoding the omega-3/omega-6 biosynthetic pathway (U.S. Pat. Nos. 7,238,482; 7,465,564; 7,550,286; 7,588,931; and 7,932,077; Appl. Publ. Nos. 2009-0093543-A1 and 2010-0317072-A1).

Recombinant production of any heterologous protein is generally accomplished by constructing an expression cassette in which the DNA coding for the protein of interest is placed under the control of a promoter suitable for the host cell. The expression cassette is then introduced into the host cell (i.e., usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., transformed yeast) for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast, as shown in the Table below.

TABLE 1

Characterized *Yarrowia lipolytica* Promoters

| Promoter Name | Native Gene | Reference |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546; U.S. patent application Pub. No. 2011-0059496-A1 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. patent application Pub. Nos. 2006-0094102-A1 and 2010-0068789-A1 |
| EXP1 | export protein | U.S. Pat. No. 7,932,077 |

Additionally, Juretzek et al. (*Biotech. Bioprocess Eng.*, 5:320-326 (2000)) compares the glycerol-3-phosphate dehydrogenase ["G3P"], isocitrate lyase ["ICL1"], 3-oxo-acyl-CoA thiolase ["POT1"] and acyl-CoA oxidase ["POX1", "POX2" and "POX5"] promoters with respect to their regulation and activities during growth on different carbon sources.

Despite the utility of these known promoters, however, there is a need for new improved yeast promoters for metabolic engineering of yeast (i.e., oleaginous and non-oleaginous) and for controlling the expression of heterologous genes in yeast. Furthermore, possession of a suite of promoters that can be regulated under a variety of natural growth and induction conditions in yeast will play an important role in industrial settings, wherein economical production of heterologous and/or homologous polypeptides in commercial quantities is desirable.

It is believed that promoter regions derived from the *Yarrowia lipolytica* gene encoding n-alkane-hydroxylating cytochrome P450 ["ALK2"] will be useful in expressing heterologous and/or homologous genes in transformed yeast, including *Yarrowia*.

SUMMARY OF THE INVENTION

In a first embodiment, the invention concerns a method for expressing a coding region of interest in a transformed yeast cell comprising:

a) providing a transformed yeast cell having a recombinant construct, wherein the recombinant construct comprises:
  (1) a promoter region of an ALK2 *Yarrowia* gene; and
  (2) a coding region of interest which is expressible in the yeast cell;
  wherein the promoter region is operably linked to the coding region of interest; and,
b) growing the transformed yeast cell of step (a) under conditions whereby the recombinant construct of step (a) is expressed.

In a second embodiment, the invention concerns a method for the production of an omega-3 fatty acid or omega-6 fatty acid comprising:

a) providing a transformed oleaginous yeast cell comprising a recombinant construct, wherein the recombinant construct comprises:

i) a promoter region of an ALK2 *Yarrowia* gene; and
ii) a coding region encoding at least one omega-3 fatty acid or omega-6 fatty acid biosynthetic pathway enzyme;
wherein the promoter region and the coding region are operably linked;
b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
c) optionally recovering the omega-3 fatty acid or the omega-6 fatty acid.

In another aspect, the promoter region of a *Yarrowia* gene may comprise SEQ ID NO:56.

In yet another aspect, the promoter region of the ALK2 *Yarrowia* gene further comprises an enhancer region set forth in SEQ ID NO:57, the enhancer region being operably linked to a functional yeast promoter.

In some embodiments, the promoter region of an ALK2 *Yarrowia* gene may be as set forth in SEQ ID NO:6, wherein said promoter optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;

b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;

c) substitution of a guanine ['G'] nucleotide for the cytosine ['C'] nucleotide at position 753 of SEQ ID NO:6;

d) substitution of an adenine ['A'] nucleotide or a thymine ['T'] nucleotide for the cytosine ['C'] nucleotide at position 753 of SEQ ID NO:6;

e) substitution of the nucleotide sequence 'AA' for the nucleotide sequence 'TT' at positions 41 to 42 of SEQ ID NO:6;

f) insertion of the nucleotide sequence 'TCG' between position 109 and 110 of SEQ ID NO:6;

g) insertion of the nucleotide sequence 'AAAT' between position 131 and position 132 of SEQ ID NO:6;

h) substitution of the nucleotide sequence 'AAA' for the nucleotide sequence 'TT' at positions 76 to 77 of SEQ ID NO:6;

i) substitution of the nucleotide sequence 'GTTT' for the nucleotide sequence 'AAAA' at positions 631 to 634 of SEQ ID NO:6;

j) insertion of the nucleotide sequence 'TA' between position 512 and position 513 of SEQ ID NO:6;

k) insertion of the nucleotide sequence 'TTTA' between position 365 and position 366 of SEQ ID NO:6;

l) insertion of the nucleotide sequence 'TTAAA' between position 230 and position 231 of SEQ ID NO:6; and m) any combination of part a), part b), part c), part d), part e), part f), part g), part h), part i), part j), part k), and part l) above.

More preferably, the promoter region of an ALK2 *Yarrowia* gene may be as set forth in SEQ ID NO:55, wherein said promoter comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, or 174 consecutive nucleotides, wherein the first nucleotide deleted is the adenine nucleotide ['A'] at position 1 of SEQ ID NO:55; and b) a deletion of part (a) in combination with a substitution of a thymine ['T'] nucleotide, an adenine ['A'] nucleotide, or a cytosine ['C'] nucleotide for the guanine ['G'] nucleotide at position 119 of SEQ ID NO:55.

The promoter region of an ALK2 *Yarrowia* gene may be selected from the group consisting of SEQ ID NO:7, SEQ ID NO:11, SEQ ID NO:27, SEQ ID NO:15, SEQ ID NO:47, SEQ ID NO:43, SEQ ID NO:39, SEQ ID NO:35, SEQ ID NO:31, SEQ ID NO:19, SEQ ID NO:49, SEQ ID NO:51, SEQ ID NO:53, and SEQ ID NO:55.

In various embodiments of the methods of the invention, the transformed yeast cell is an oleaginous yeast. This oleaginous yeast may be a member of a genus selected from the group consisting of *Yarrowia*, *Candida*, *Rhodotorula*, *Rhodosporidium*, *Cryptococcus*, *Trichosporon* and *Lipomyces*.

Additionally, provided herein is an isolated nucleic acid molecule comprising a promoter region of an ALK2 *Yarrowia* selected from the group consisting of:

(a) SEQ ID NO:7;
(b) SEQ ID NO:11;
(c) SEQ ID NO:27;
(d) SEQ ID NO:15;
(e) SEQ ID NO:47;
(f) SEQ ID NO:43;
(g) SEQ ID NO:39;
(h) SEQ ID NO:35;
(i) SEQ ID NO:31;
(j) SEQ ID NO:19;
(k) SEQ ID NO:49;
(l) SEQ ID NO:51;
(m) SEQ ID NO:53;
(n) SEQ ID NO:6, wherein said promoter optionally comprises at least one modification selected from the group consisting of:
(i) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;
(ii) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;
(iii) substitution of a guanine ['G'] nucleotide for the cytosine ['C'] nucleotide at position 753 of SEQ ID NO:6;
(iv) substitution of an adenine ['A'] nucleotide or a thymine ['T'] nucleotide for the cytosine ['C'] nucleotide at position 753 of SEQ ID NO:6;
(v) substitution of the nucleotide sequence 'AA' for the nucleotide sequence 'TT' at position 41 and 42 of SEQ ID NO:6;
(vi) insertion of the nucleotide sequence 'TCG' between position 109 and 110 of SEQ ID NO:6;
(vii) insertion of the nucleotide sequence 'AAAT' between position 131 and position 132 of SEQ ID NO:6;
(viii) substitution of the nucleotide sequence 'AAA' for the nucleotide sequence 'TT' at positions 76 to 77 of SEQ ID NO:6;
(ix) substitution of the nucleotide sequence 'GTTT' for the nucleotide sequence 'AAAA' at positions 631 to 634 of SEQ ID NO:6;
(x) insertion of the nucleotide sequence 'TA' between position 512 and position 513 of SEQ ID NO:6;
(xi) insertion of the nucleotide sequence 'TTTA' between position 365 and position 366 of SEQ ID NO:6;
(xii) insertion of the nucleotide sequence 'TTAAA' between position 230 and position 231 of SEQ ID NO:6; and (xiii) any combination of part (i), part (ii), part (iii), part (iv), part (v), part (vi), part (vii), part (viii), part (ix), part (x), part (xi), and part (xii) above; and (o) a promoter region comprising SEQ ID NO:55.

Also provided herein is an isolated nucleic acid molecule comprising a promoter region of an ALK2 *Yarrowia* gene, wherein the promoter region of the ALK2 *Yarrowia* gene further comprises an enhancer region set forth in SEQ ID NO:57, the enhancer region being operably linked to a functional yeast promoter.

BRIEF DESCRIPTION OF THE DRAWINGS AND SEQUENCE DESCRIPTIONS

FIG. 1 graphically represents the relationship between SEQ ID NOs:2, 6, 7, 11, 15, 19, 49, 51, 53, 55, and 56, each of which relates to promoter regions derived from the 5' upstream region of the n-alkane-hydroxylating cytochrome P450 ["ALK2"] gene in *Yarrowia lipolytica*.

Figure 2B:
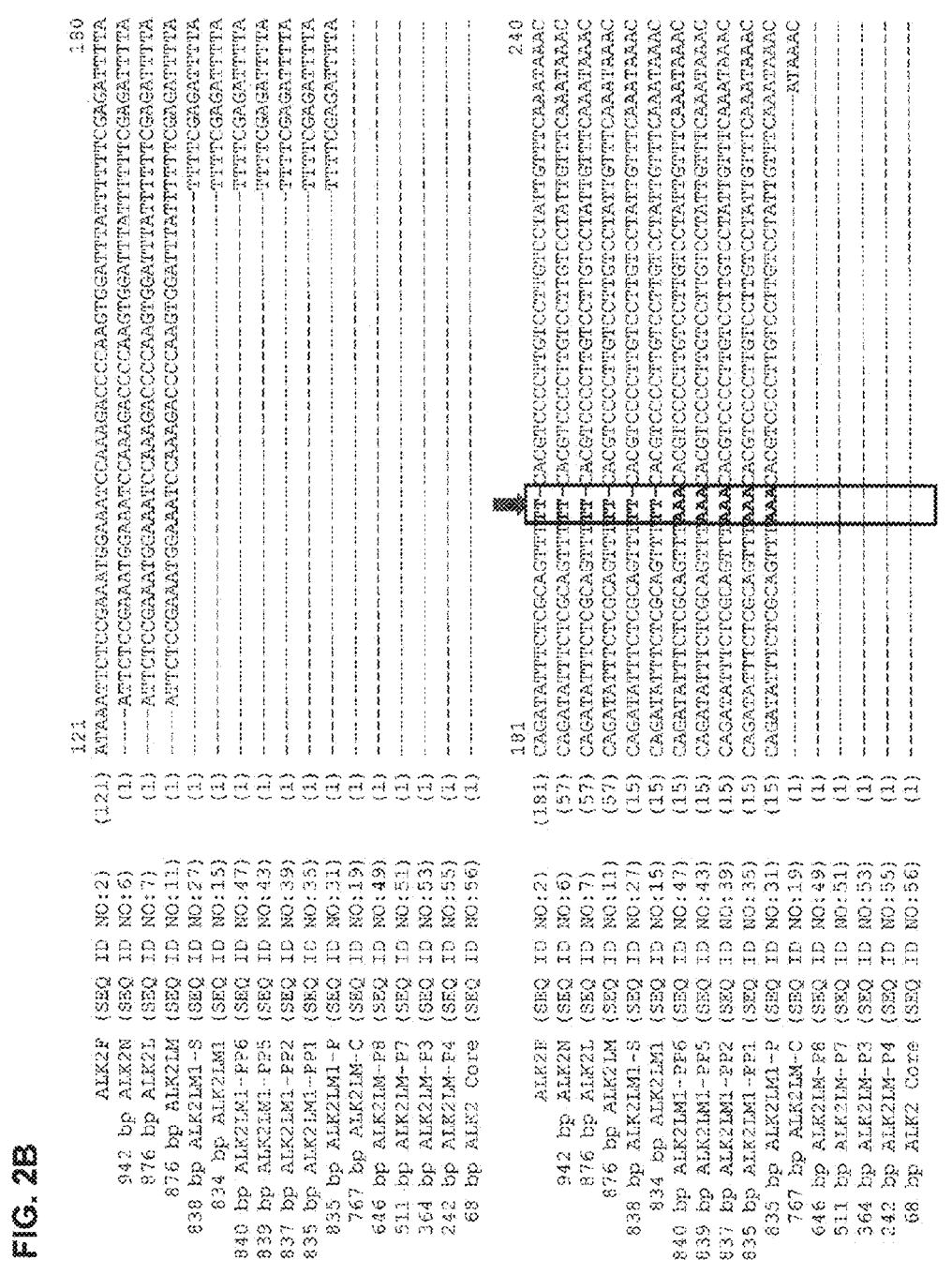
Figure 2D:
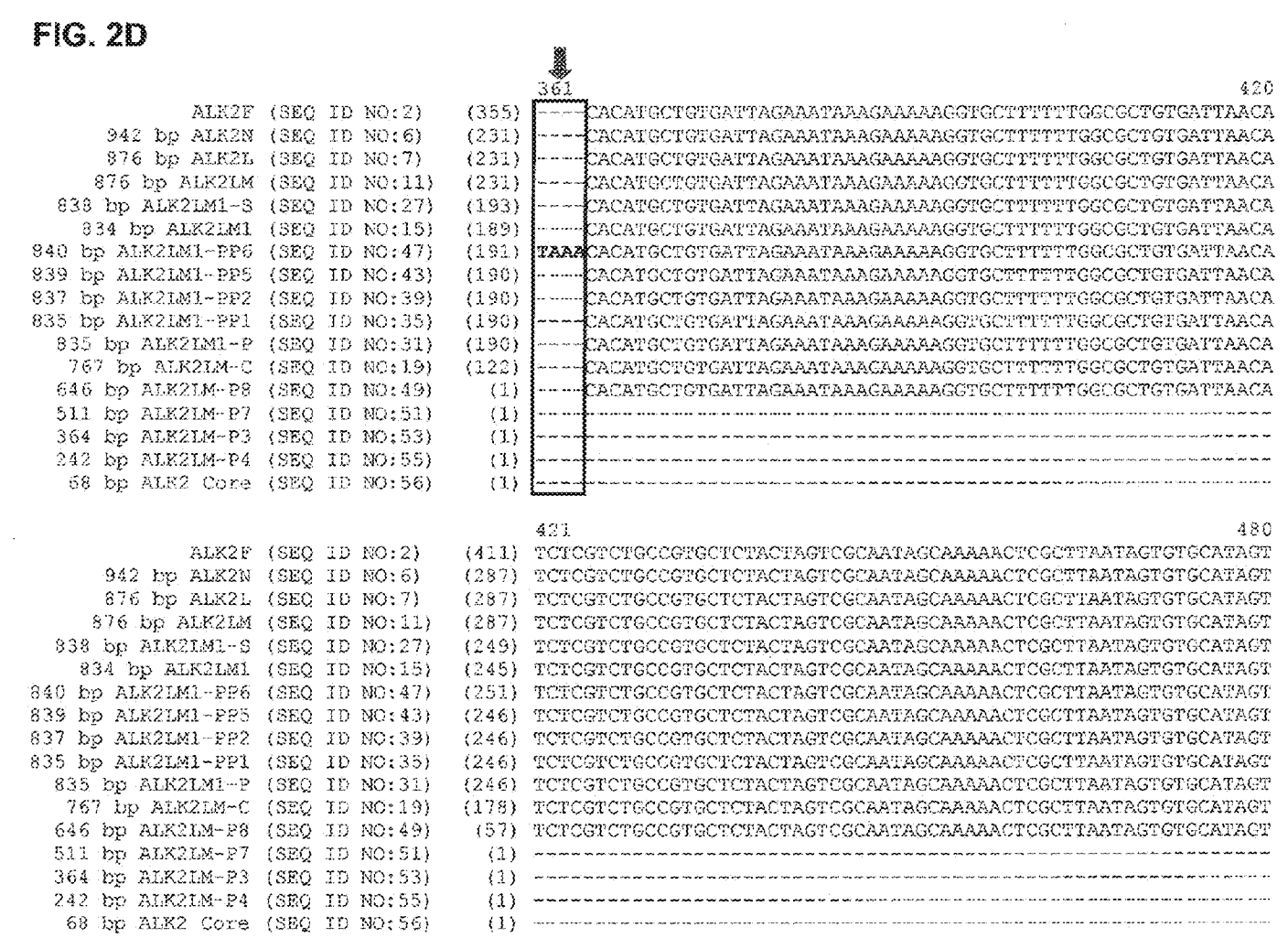
Figure 2G:
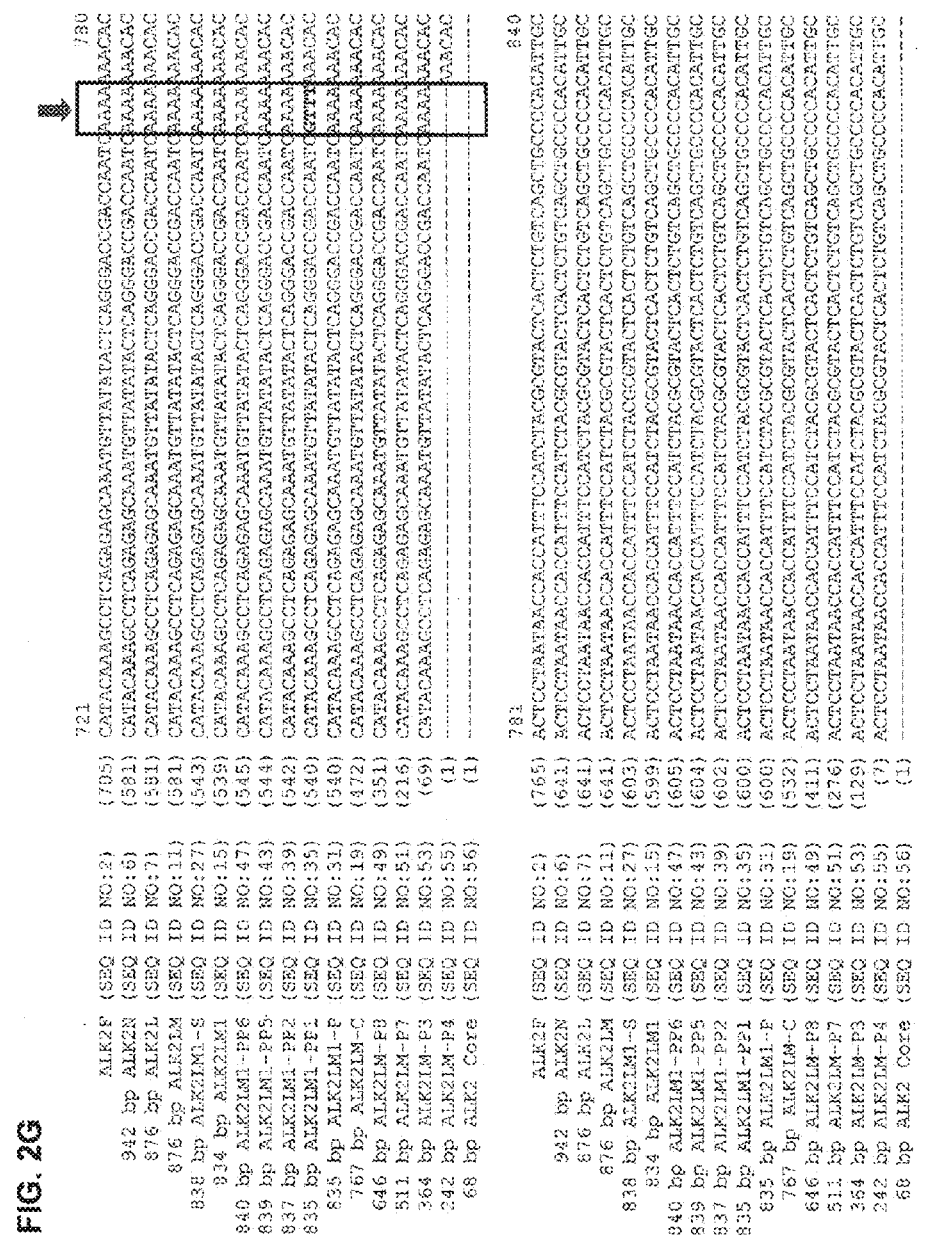
Figure 2H:
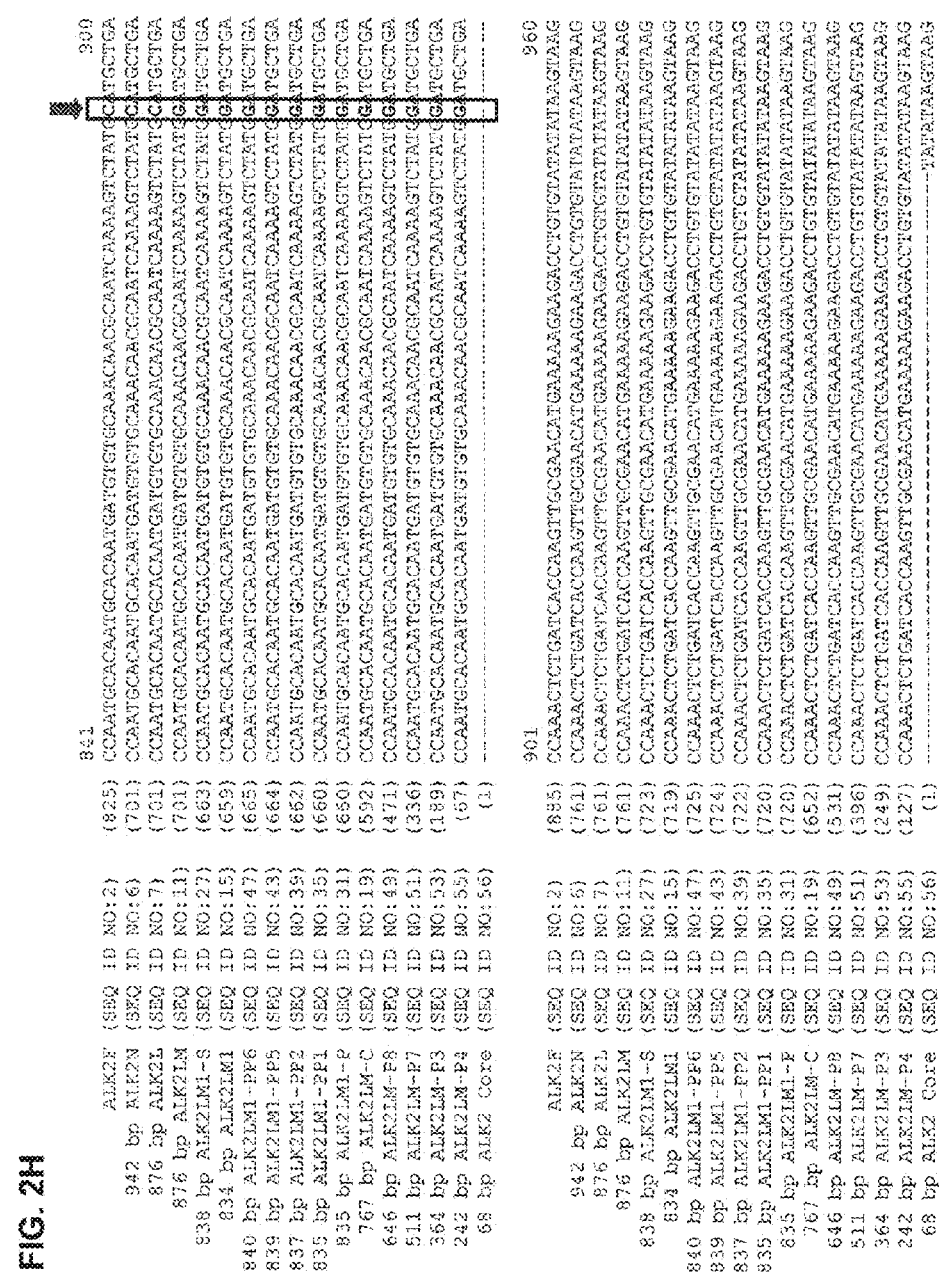

FIGS. 2A, 2B, 2C, 2D, 2E, 2F, 2G, 2H, 2I, and 2J (which should be viewed together as FIG. 2) provide an alignment of:
(a) the *Y. lipolytica* ALK2 (SEQ ID NO:2) promoter region, which is the 1000 bp 5' upstream sequence (i.e., the −1000 to −1 region) of the n-alkane-hydroxylating cytochrome P450 ["ALK2"] gene in *Y. lipolytica*, wherein the nucleotide 'A' of the ALK2 translation initiation codon 'ATG' was designated as +1 (note that the ATG codon is shown in SEQ ID NO:6);
(b) the 942 bp ALK2N (SEQ ID NO:6) promoter region, which comprises the 876 bp 5' upstream sequence (i.e., the −876 to −1 region) of the n-alkane-hydroxylating cytochrome P450 ["ALK2"] gene in *Y. lipolytica* and the first 66 bp of the coding region, wherein the nucleotide 'A' of the ALK2 translation initiation codon 'ATG' was designated as +1;
(c) the 876 bp ALK2L (SEQ ID NO:7) promoter region;
(d) the 876 bp ALK2LM (SEQ ID NO:11) promoter region;
(e) the 838 bp ALK2LM1-S (SEQ ID NO:27) promoter region;
(f) the 834 bp ALK2LM1 (SEQ ID NO:15) promoter region;
(g) the 840 bp ALK2LM1-PP6 (SEQ ID NO:47) promoter region;
(h) the 839 bp ALK2LM1-PP5 (SEQ ID NO:43) promoter region;
(i) the 837 bp ALK2LM1-PP2 (SEQ ID NO:39) promoter region;
(j) the 835 bp ALK2LM1-PP1 (SEQ ID NO:35) promoter region;
(k) the 835 bp ALK2LM1-P (SEQ ID NO:31) promoter region;
(l) the 767 bp ALK2LM-C (SEQ ID NO:19) promoter region;
(m) the 646 bp ALK2LM-P8 (SEQ ID NO:49) promoter region;
(n) the 511 bp ALK2LM-P7 (SEQ ID NO:51) promoter region;
(o) the 364 bp ALK2LM-P3 (SEQ ID NO:53) promoter region;
(p) the 242 bp ALK2LM-P4 (SEQ ID NO:55) promoter region; and
(q) the 68 bp minimal (Core) ALK2 (SEQ ID NO:56) promoter region.

Base pair differences are highlighted with an arrow and box.

Figure 3:
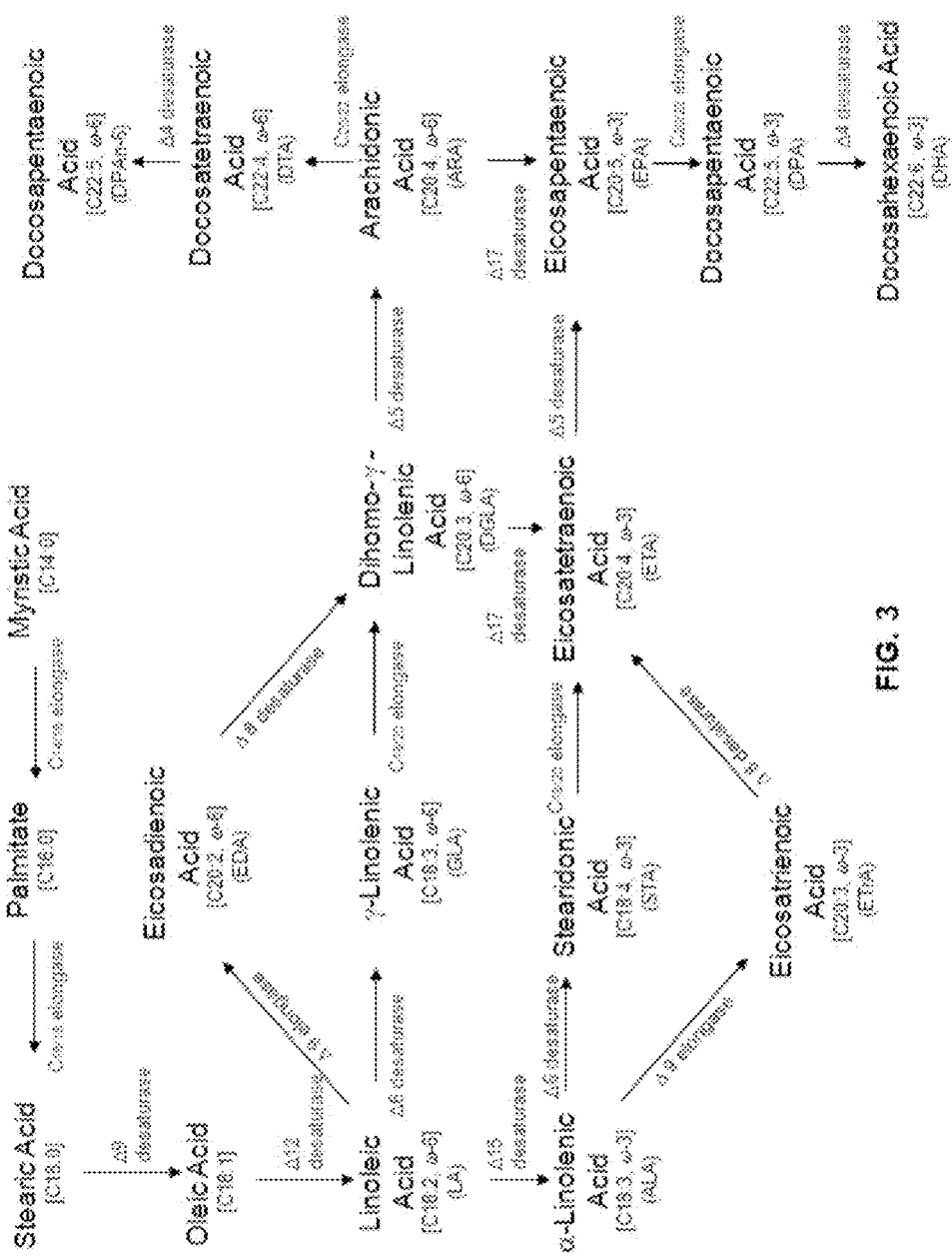

FIG. 3 illustrates the omega-3/omega-6 fatty acid biosynthetic pathway.

FIG. 4 provides plasmid maps for the following: (A) pDMW212 and (B) pAKL2GUS.

Figure 5:
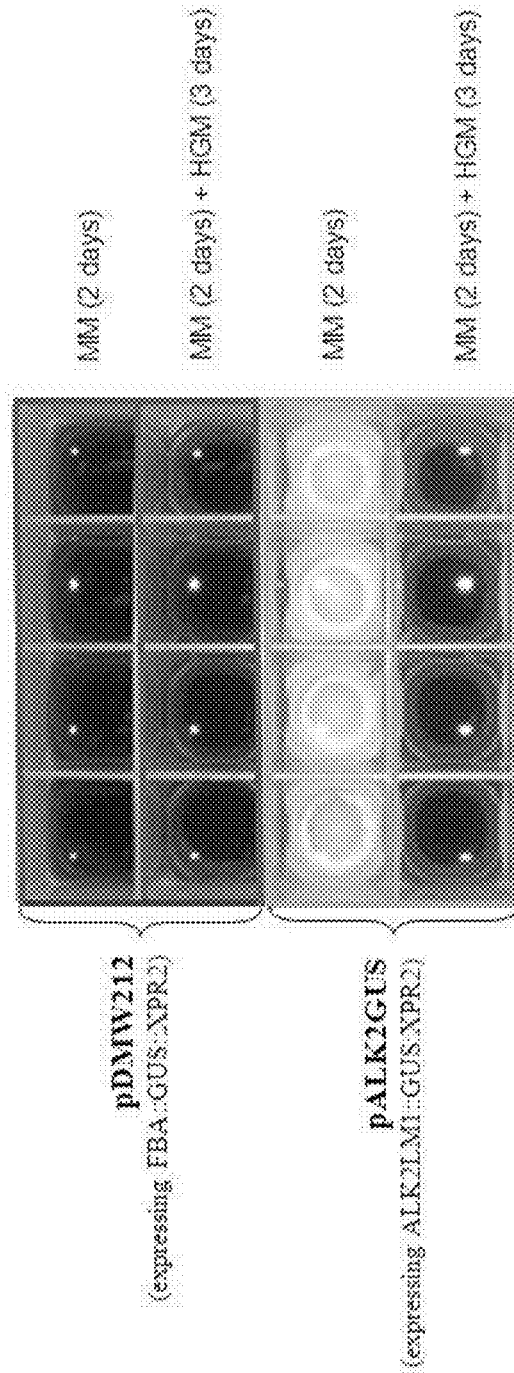

FIG. 5 is an image of cell cultures comparing the promoter activity of 834 bp AKL2LM1 (SEQ ID NO:15) and FBA in *Yarrowia lipolytica* as determined by histochemical staining.

The invention can be more fully understood from the following detailed description and the accompanying sequence descriptions, which form a part of this application.

SEQ ID NOs:1-58 are promoters, ORFs encoding genes (or portions thereof), primers, or plasmids, as identified in Table 2.

TABLE 2

Summary Of Nucleic Acid SEQ ID Numbers

| Description | Nucleic acid SEQ ID NO. |
|---|---|
| *Yarrowia* ALK2 gene ("YALI0F01320g") | 1 (2872 bp) |
| 1000 bp ALK2F *Yarrowia* promoter region | 2 (1000 bp) |
| Primer Y1198 | 3 (32 bp) |
| Primer Y1199 | 4 (33 bp) |
| Plasmid pT-ALK2Pro | 5 (4906 bp) |
| 942 bp ALK2N *Yarrowia* promoter region | 6 (942 bp) |
| 876 bp ALK2L *Yarrowia* promoter region | 7 (876 bp) |
| Plasmid pT-ALK2Pro-(S) | 8 (4906 bp) |
| Primer Y1202 | 9 (35 bp) |
| Primer Y1203 | 10 (35 bp) |
| 876 bp ALK2LM *Yarrowia* promoter region | 11 (876 bp) |
| Plasmid pT-ALK2Pro-(S)S | 12 (4906 bp) |
| Primer Y1208 | 13 (36 bp) |
| Primer Y1209 | 14 (36 bp) |
| 834 bp ALK2LM1 *Yarrowia* promoter region | 15 (834 bp) |
| Plasmid pT-ALK2Pro-(S)C | 16 (4909 bp) |
| Primer Y1262 | 17 (37 bp) |
| Primer Y1263 | 18 (37 bp) |
| 767 bp ALK2LM-C *Yarrowia* promoter region | 19 (767 bp) |
| Plasmid pALK2GUS | 20 (9415 bp) |
| Plasmid pDMW212 | 21 (9348 bp) |
| Plasmid pDG2LGUS (U.S. application Ser. No. 61/469,933, filed Mar. 31, 2011) | 22 (9499 bp) |
| Plasmid pALK2GUS-C | 23 (9364 bp) |
| Primer Y2148 | 24 (38 bp) |
| Primer Y2149 | 25 (38 bp) |
| Plasmid pALK2GUS-S | 26 (9419 bp) |
| 838 bp ALK2LM1-S *Yarrowia* promoter region | 27 (838 bp) |
| Primer Y1244 | 28 (38 bp) |
| Primer Y1245 | 29 (38 bp) |
| Plasmid pALK2GUS-P | 30 (9414 bp) |
| 835 bp ALK2LM1-P *Yarrowia* promoter region | 31 (835 bp) |
| Primer Y1250 | 32 (38 bp) |
| Primer Y1251 | 33 (38 bp) |
| Plasmid pALK2GUS-P1 | 34 (9414 bp) |
| 835 bp ALK2LM1-PP1 *Yarrowia* promoter region | 35 (835 bp) |
| Primer Y2158 | 36 (36 bp) |
| Primer Y2159 | 37 (36 bp) |
| Plasmid pALK2GUS-P2 | 38 (9416 bp) |
| 837 bp ALK2LM1-PP2 *Yarrowia* promoter region | 39 (837 bp) |
| Primer Y2170 | 40 (43 bp) |
| Primer Y2171 | 41 (43 bp) |
| Plasmid pALK2GUS-P5 | 42 (9418 bp) |
| 839 bp ALK2LM1-PP5 *Yarrowia* promoter region | 43 (839 bp) |
| Primer Y2172 | 44 (42 bp) |
| Primer Y2173 | 45 (42 bp) |
| Plasmid pALK2GUS-P6 | 46 (9419 bp) |
| 840 bp ALK2LM1-PP6 *Yarrowia* promoter region | 47 (840 bp) |
| Plasmid pALK2GUS-P8 | 48 (9261 bp) |
| 646 bp ALK2LM-P8 *Yarrowia* promoter region | 49 (646 bp) |
| Plasmid pALK2GUS-P7 | 50 (9124 bp) |
| 511 bp ALK2LM-P7 *Yarrowia* promoter region | 51 (511 bp) |
| Plasmid pALK2GUS-P3 | 52 (8977 bp) |
| 364 bp ALK2LM-P3 *Yarrowia* promoter region | 53 (364 bp) |
| Plasmid pALK2GUS-P4 | 54 (8854 bp) |
| 242 bp ALK2LM-P4 *Yarrowia* promoter region | 55 (242 bp) |
| 68 bp minimal ALK2 *Yarrowia* promoter | 56 (68 bp) |
| 147 bp ALK2 *Yarrowia* enhancer region | 57 (147 bp) |
| Consensus sequence $[A(A_{rich})_5 NY\underline{A}(A/T)NN(A_{rich})_6]$ located in promoter sequences of *S. cerevisiae* genes | 58 (18 bp) |

DETAILED DESCRIPTION OF THE INVENTION

All patents, patent applications, and publications cited herein are hereby incorporated by reference in their entirety.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

The term "yeast" refers to a phylogenetically diverse grouping of single-celled fungi. Yeast do not form a specific taxonomic or phylogenetic grouping, but instead comprise a diverse assemblage of unicellular organisms that occur in the Ascomycotina and Basidiomycotina. Collectively, about 100 genera of yeast have been identified, comprising approximately 1,500 species (Kurtzman and Fell, *Yeast Systematics And Phylogeny: Implications Of Molecular Identification Methods For Studies In Ecology*. In C. A. Rosa and G. Peter, eds., *The Yeast Handbook*. Germany: Springer-Verlag Berlin Herdelberg, 2006). Yeast reproduce principally by budding (or fission) and derive energy from fermentation, via conversion of carbohydrates to ethanol and carbon dioxide. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

The term "oleaginous" refers to those organisms that tend to store their energy source in the form of oil (Weete, In: Fungal Lipid Biochemistry, 2$^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are not limited to, the following genera: *Yarrowia, Candida, Rhodotorula, Rhodosporidium, Cryptococcus, Trichosporon* and *Lipomyces*. Alternatively, organisms classified as yeasts that are genetically modified to become oleaginous such that they can produce more than 25% of their dry cell weight as oil are also "oleaginous", e.g., yeast such as *Saccharomyces cerevisiae* (Int'l. App. Pub. No. WO 2006/102342).

The term "fermentable carbon source" will refer to a carbon source that a microorganism will metabolize to derive energy. Typical carbon sources for use in the methods herein include, but are not limited to: monosaccharides, disaccharides, oligosaccharides, polysaccharides, alkanes, fatty acids, esters of fatty acids, glycerol, monoglycerides, diglycerides, triglycerides, carbon dioxide, methanol, formaldehyde, formate and carbon-containing amines. Most preferred is glucose, sucrose, invert sucrose, fructose, glycerol and/or fatty acids containing between 10-22 carbons. The term "invert sucrose" (or "invert sugar") refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

The term "ALK2" refers to an n-alkane-hydroxylating cytochrome P450 ("YALI0F01320g", Dujon, B. et al., *Nature*, 430(6995):35-44 (2004)) encoded by the ALK2 gene. ALK2 transcription was increased in *Yarrowia* strains with their native snf1 gene knocked-out (U.S. Pat. Appl. Publ. No. 2010-0062502-A1). This enzyme catalyzes the terminal hydroxylation of n-alkanes.

An "ALK2 *Yarrowia* gene" refers to a gene encoding ALK2 from a yeast of the genus *Yarrowia*. For example, a 2872 bp DNA sequence ("YALI0F01320g") that encodes an n-alkane-hydroxylating cytochromes P450 is provided as SEQ ID NO:1 (Dujon, B. et al., *Nature*, 430(6995):35-44 (2004)).

The term "promoter region of an ALK2 *Yarrowia* gene" or "*Yarrowia* ALK2 promoter region" refers to the 5' upstream untranslated region in front of the 'ATG' translation initiation codon of a *Yarrowia* ALK2 gene, or sequences derived therefrom, and that is necessary for expression. Thus, it is believed that promoter regions of an ALK2 *Yarrowia* gene will comprise a portion of the ~1000 bp 5' upstream of an ALK2 *Yarrowia* gene. The sequence of the *Yarrowia* ALK2 promoter region may correspond exactly to native sequence upstream of the ALK2 *Yarrowia* gene (i.e., a "wildtype" or "native" *Yarrowia* ALK2 promoter); alternately, the sequence of the *Yarrowia* ALK2 promoter region may be "modified" or "mutated", thereby comprising various substitutions, deletions, and/or insertions of one or more nucleotides relative to a wildtype or native *Yarrowia* ALK2 promoter. These modifications can result in a modified *Yarrowia* ALK2 promoter having increased, decreased or equivalent promoter activity, when compared to the promoter activity of the corresponding wildtype or native *Yarrowia* ALK2 promoter. The term "mutant promoter" or "modified promoter" will encompass natural variants and in vitro generated variants obtained using methods well known in the art (e.g., classical mutagenesis, site-directed mutagenesis and "DNA shuffling").

Described herein is a wildtype *Yarrowia* ALK2 promoter region (SEQ ID NO:2 comprising the −1000 to −1 upstream region of the ALK2 gene SEQ ID NO:1) based on nucleotide numbering such that the 'A' position of the 'ATG' translation initiation codon is designated as +1. The ATG translation initiation codon is located at nucleotide positions 1001-1003 in SEQ ID NO:1. Alternately, and yet by no means limiting in nature, a wildtype *Yarrowia* ALK2 promoter region may comprise the −876 to −1 region of SEQ ID NO:1, the −840 to −1 region of SEQ ID NO:1, the −839 to −1 region of SEQ ID NO:1, the −838 to −1 region of SEQ ID NO:1, the −837 to −1 region of SEQ ID NO:1, the −835 to −1 region of SEQ ID NO:1, the −834 to −1 region of SEQ ID NO:1; the −767 to −1 region of SEQ ID NO:1; the −646 to −1 region of SEQ ID NO:1; the −511 to −1 region of SEQ ID NO:1; the −364 to −1 region of SEQ ID NO:1; the −242 to −1 region of SEQ ID NO:1, or the −68 to −1 region of SEQ ID NO:1 (where the "−1" position in SEQ ID NO:1 is the nucleotide that is 5′-adjacent to the ATG translation initiation codon). Similarly, a modified *Yarrowia* ALK2 promoter region may comprise the promoter region of an ALK2 *Yarrowia* gene as set forth in SEQ ID NO:6, wherein said promoter optionally comprises at least one modification selected from the group consisting of:

a) a deletion at the 5′-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;

b) a deletion at the 3′-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;

c) substitution of a guanine ['G'] nucleotide for the cytosine ['C'] nucleotide at position 753 of SEQ ID NO:6;

d) substitution of an adenine ['A'] nucleotide or a thymine ['T'] nucleotide for the cytosine ['C'] nucleotide at position 753 of SEQ ID NO:6;

e) substitution of the nucleotide sequence 'AA' for the nucleotide sequence 'TT' at positions 41 to 42 of SEQ ID NO:6;

f) insertion of the nucleotide sequence 'TCG' between position 109 and 110 of SEQ ID NO:6;

g) insertion of the nucleotide sequence 'AAAT' between position 131 and position 132 of SEQ ID NO:6;

h) substitution of the nucleotide sequence 'AAA' for the nucleotide sequence 'TT' at positions 76 to 77 of SEQ ID NO:6;

i) substitution of the nucleotide sequence 'GTTT' for the nucleotide sequence 'AAAA' at positions 631 to 634 of SEQ ID NO:6;

j) insertion of the nucleotide sequence 'TA' between position 512 and position 513 of SEQ ID NO:6;

k) insertion of the nucleotide sequence 'TTTA' between position 365 and position 366 of SEQ ID NO:6;

l) insertion of the nucleotide sequence 'TTAAA' between position 230 and position 231 of SEQ ID NO:6; and m) any combination of part a), part b), part c), part d), part e), part f), part g), part h), part i), part j), part k), and part l) above.

These examples are not intended to be limiting in nature and will be elaborated below. FIG. 1 graphically illustrates various *Yarrowia* ALK2 promoter regions (i.e., SEQ ID NO:6 [942 bp ALK2LN, comprising an 876 bp promoter region plus a 66 bp N-terminal protein coding region], SEQ ID NO:7 [876 bp ALK2L], SEQ ID NO:11 [876 bp ALK2LM], SEQ ID NO:15 [834 bp ALK2LM1], SEQ ID NO:19 [767 bp ALK2LM-C], SEQ ID NO:49 [646 bp ALK2LM-P8], SEQ ID NO:51 [511 bp ALK2LM-P7], SEQ ID NO:53 [364 bp ALK2LM-P3], SEQ ID NO:55 [242 bp ALK2LM-P4], and SEQ ID NO:56 [68 bp minimal/core promoter]), with the 1000 bp 5′ upstream region (SEQ ID NO:2) of the ALK2 initiation codon of the *Yarrowia* ALK2 gene as a reference.

The term "promoter activity" will refer to an assessment of the transcriptional efficiency of a promoter. This may, for instance, be determined directly by measurement of the amount of mRNA transcription from the promoter (e.g., by quantitative PCR or Northern blotting or primer extension methods) or indirectly by measuring the amount of gene product expressed from the promoter.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid sequence or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The disclosure herein teaches partial or complete nucleotide sequences containing one or more particular yeast promoters. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the disclosure herein encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, CABIOS, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides from other species, wherein such polypeptides have the same or similar function or activity. Likewise, suitable promoter regions (isolated polynucleotides of the present invention) are at least about 70-85% identical, and more preferably at least about 85-95% identical to the nucleotide sequences reported herein. Although preferred ranges are described above, useful examples of percent identities include any integer percentage from 70% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable *Yarrowia* ALK2 promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes herein will typically comprise a promoter region of an ALK2 *Yarrowia* gene operably linked to a coding region of interest. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. The terms "coding sequence" and "coding region" are used interchangeably herein. A "coding region of interest" is a coding region which is desired to be expressed. Such coding regions are discussed more fully hereinbelow. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

"Promoter" refers to a DNA sequence that facilitates transcription of a coding sequence, thereby enabling gene expression. In general, a promoter is typically located on the same strand and upstream of the coding sequence (i.e., 5' of the coding sequence). Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

"Minimal promoter" refers to the minimal length of DNA sequence that is necessary to initiate basal level transcription of an operably linked coding sequence. The "minimal promoter" usually does not include the untranslated region located between transcription start site and translation start site. Although promoters often interact with the TATA binding protein ["TBP"] to create a transcription initiation complex from which RNA polymerase II transcribes the DNA coding sequence, only some promoters contain a TATA box to which TBP binds directly. In yeast, the TATA-box is usually located about 20 to 130 bp upstream of the transcription start site. For those TATA-less promoters, it is thought that transcription factor TFIID coordinates delivery of TBP and functions largely to stabilize TBP binding in lieu of a TATA box (Basehoar et al., *Cell*, 116:699-709 (2004)). Some TATA-less promoters contain an "initiator" element [A(A$_{rich}$)$_5$NY A(A/T)NN(A$_{rich}$)$_6$ (SEQ ID NO:58), Zhang, Z. and Dietrich, F. S., *Nucleic Acids Res.*, 33:2838-2851 (2005), incorporated herein by reference] located around the transcription start site, which can direct basal level transcription.

Thus, the minimal promoter region for the ALK2 TATA-containing promoters is herein defined as the −68 to −1 region upstream of the ALK2 gene (i.e., as set forth in SEQ ID NO:56), which contains a TATA box sufficient to initiate basal level transcription of an operably linked coding sequence.

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "enhancer" refers to a cis-regulatory sequence that can elevate levels of transcription from an adjacent eukaryotic promoter, thereby increasing transcription of the gene. Enhancers can act on promoters over many kilobases of DNA and can be 5' or 3' to the promoter they regulate. Enhancers can also be located within introns (Giacopelli F. et al., *Gene Expr.*, 11:95-104 (2003)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

"Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism.

Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise one or more expression cassettes. In another example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain strains displaying the desired expression level and pattern. Such screening may be accomplished by Southern analysis of DNA, Northern analysis of mRNA expression, Western and/or Elisa analyses of protein expression, formation of a specific product, phenotypic analysis or GC analysis of the PUFA products, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

N-alkane-hydroxylating cytochrome P450 enzymes include those enzymes that catalyze the terminal hydroxylation of n-alkanes. Within *Yarrowia lipolytica*, a gene encoding an n-alkane-hydroxylating cytochrome P450 enzyme has been identified (SEQ ID NO:1, "YALI0F01320g" locus, Dujon, B. et al., *Nature*, 430(6995):35-44 (2004)).

*Yarrowia* mutants having their native snf1 gene knocked-out can constitutively accumulate high levels of oil, even in nitrogenous growth media, when compared to the wild-type strains (U.S. Pat. Appl. Publ. No. 2010-0062502-A1). The snf1 gene encodes the alpha subunit of the SNF1 protein kinase, a heterotrimeric serine/threonine protein kinase that appears to function as a global regulator of gene expression. Particularly, SNF1 protein kinase regulates the transcription of numerous glucose-repressed genes, with a significant portion of those genes functioning in transcription and signal transduction. In general, when the heterotrimeric kinase is activated by phosphorylation, for example, in response to glucose limitation, ATP-producing catabolic pathways increase.

Based on microarray analysis in *Y. lipolytica*, it has been determined that over 200 genes are differentially expressed by more than 1.3-fold in snf1 knock-out strains, when compared to their expression in control strains (U.S. Pat. Appl. Publ. No. 2010-0062502-A1, Example 11 therein). Interestingly, the transcription of ALK2 in these snf1 knock-out strains was increased as much as three times that of the wild-type strains.

Based on the above, the ALK2 gene was identified as a potential source of new and improved yeast promoters for metabolic engineering of yeast and for controlling heterologous genes in yeast. In order to understand the means by which ALK2 expression is regulated in *Yarrowia*, the ALK2 promoter was isolated and its functional structure was mechanistically analyzed.

In general, a promoter useful for controlling the expression of heterologous genes in yeast should preferably meet criteria with respect to strength, activities, pH tolerance and inducibility, as described in U.S. Pat. No. 7,259,255. Additionally, today's complex metabolic engineering utilized for construction of yeast having the capability to produce a variety of heterologous polypeptides in commercial quantities requires a suite of promoters that are regulatable under a variety of natural growth and induction conditions.

Thus, described herein are a suite of promoter regions of an ALK2 *Yarrowia* gene, useful for driving expression of any suitable coding region of interest in a transformed yeast cell. More specifically, described herein is an isolated nucleic acid molecule comprising a promoter region of an ALK2 *Yarrowia* gene, wherein said promoter region of an ALK2 *Yarrowia* gene is set forth in SEQ ID NO:6 (corresponding to the 5' upstream −876 to −1 region plus the first 66 bp of the N-terminal protein coding region of the *Yarrowia* ALK2 gene), and wherein said promoter optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;

b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;

c) substitution of a guanine ['G'] nucleotide for the cytosine ['C'] nucleotide at position 753 of SEQ ID NO:6;

d) substitution of an adenine ['A'] nucleotide or a thymine ['T'] nucleotide for the cytosine ['C'] nucleotide at position 753 of SEQ ID NO:6;
e) substitution of the nucleotide sequence 'AA' for the nucleotide sequence "TT" at positions 41 to 42 of SEQ ID NO:6;
f) insertion of the nucleotide sequence 'TCG' between position 109 and 110 of SEQ ID NO:6;
g) insertion of the nucleotide sequence 'AAAT' between position 131 and position 132 of SEQ ID NO:6;
h) substitution of the nucleotide sequence 'AAA' for the nucleotide sequence 'TT' at positions 76 to 77 of SEQ ID NO:6;
i) substitution of the nucleotide sequence 'GTTT' for the nucleotide sequence 'AAAA' at positions 631 to 634 of SEQ ID NO:6;
j) insertion of the nucleotide sequence 'TA' between position 512 and position 513 of SEQ ID NO:6;
k) insertion of the nucleotide sequence 'TTTA' between position 365 and position 366 of SEQ ID NO:6;
l) insertion of the nucleotide sequence 'TTAAA' between position 230 and position 231 of SEQ ID NO:6; and
m) any combination of part a), part b), part c), part d), part e), part f), part g), part h), part i), part j), part k), and part l) above.

In some embodiments, the promoter region of an ALK2 *Yarrowia* gene is selected from the group consisting of SEQ ID NOs:7, 11, 15, 19, 27, 31, 35, 39, 43, 47, 49, 51, 53 and 55. These promoter regions are preferred to provide relatively high levels of inducible promoter activity when operably linked to a coding region of interest.

The relationship between the promoter regions of a *Yarrowia* ALK2 gene selected from the group consisting of SEQ ID NOs:2, 6, 7, 11, 27, 15, 47, 43, 39, 35, 31, 19, 49, 51, 53, 55, 56, supra, is readily observed upon alignment of the individual promoter sequences. Specifically, FIG. 2 (comprising FIGS. 2A, 2B, 2C, 2D, 2E, 2F, 2G, 2H, 2I, and 2J) provides an alignment of:

(a) the 1000 bp promoter region ALK2F (SEQ ID NO:2);
(b) the 942 bp promoter region ALK2N (SEQ ID NO:6);
(c) the 876 bp promoter region ALK2L (SEQ ID NO:7);
(d) the 876 bp promoter region ALK2LM (SEQ ID NO:11);
(e) the 838 bp promoter region ALK2LM1-S (SEQ ID NO:27);
(f) the 834 bp promoter region ALK2LM1 (SEQ ID NO:15);
(g) the 840 bp promoter region ALK2LM1-PP6 (SEQ ID NO:47);
(h) the 839 bp promoter region ALK2LM1-PP5 (SEQ ID NO:43);
(i) the 837 bp promoter region ALK2LM1-PP2 (SEQ ID NO:39);
(j) the 835 bp promoter region ALK2LM1-PP1 (SEQ ID NO:35);
(k) the 835 bp promoter region ALK2LM1-P (SEQ ID NO:31);
(l) the 767 bp promoter region ALK2LM-C (SEQ ID NO:19);
(m) the 646 bp promoter region ALK2LM-P8 (SEQ ID NO:49);
(n) the 511 bp promoter region ALK2LM-P7 (SEQ ID NO:51);
(o) the 364 bp promoter region ALK2LM-P3 (SEQ ID NO:53);
(p) the 242 bp promoter region ALK2LM-P4 (SEQ ID NO:55); and,
(q) the 68 bp *Yarrowia* promoter region ALK2 minimal/core promoter (SEQ ID NO:56).

Nucleotide differences are highlighted with a box and an arrow.

As will be obvious to one of skill in the art, the above discussion is by no means limiting to the description of suitable promoter regions of an ALK2 *Yarrowia* gene. For example, alternate *Yarrowia* ALK2 promoter regions may be longer than the 1000 bp sequence 5'upstream of the nucleotide 'A' (designated as +1) of the translation initiation codon 'ATG' of SEQ ID NO:1, thereby encompassing additional nucleotides.

Similarly, it should be recognized that promoter fragments of various diminishing lengths may have identical promoter activity, since the exact boundaries of the regulatory sequences have not been completely defined. Thus, for example, it is also contemplated that a suitable promoter region of an ALK2 *Yarrowia* gene could also include a promoter region of SEQ ID NO:6, wherein the 5'-terminus deletion was greater than 634 consecutive nucleotides.

More specifically, based on sequence analysis of the promoter region set forth in SEQ ID NO:55, and identification of a TATA box spanning positions −68 to −62 5' upstream of the ATG translation initiation codon, it is hypothesized herein that the minimal promoter region that could function for basal level transcription initiation of an operably linked coding region of interest encompasses (at least) the 68 bp 5' upstream untranslated region from the 'ATG' translation initiation codon of an ALK2 *Yarrowia* gene comprising the −68 to −1 region of SEQ ID NO:1; this 68 bp region is set forth independently as SEQ ID NO:56.

In alternate embodiments, SEQ ID NO:56 could be utilized as a minimal promoter to fuse with enhancers to drive increased transcription from a coding region of interest. One of skill in the art would readily be able to conduct appropriate deletion studies to determine the appropriate length of a promoter region of an ALK2 *Yarrowia* gene required to enable the desired level of promoter activity.

In alternate embodiments, SEQ ID NO:57 could be used as an enhancer to elevate levels of transcription from an adjacent eukaryotic coding region of interest, or fused with a minimal promoter to form a recombinant promoter to drive expression of a coding region of interest. One of skill in the art would readily be able to conduct appropriate deletion studies to determine the minimal length of the enhancer region (SEQ ID NO:57) to enable the desired level of promoter activity.

Thus, in alternate embodiments, described herein is an isolated nucleic acid molecule comprising a promoter region of an ALK2 *Yarrowia* gene, wherein said isolated nucleic acid molecule is selected from the group consisting of SEQ ID NO:7, SEQ ID NO:11, SEQ ID NO:27, SEQ ID NO:15, SEQ ID NO:47, SEQ ID NO:43, SEQ ID NO:39, SEQ ID NO:35, SEQ ID NO:31, SEQ ID NO:19, SEQ ID NO:49, SEQ ID NO:51, SEQ ID NO:53, and SEQ ID NO:55 More specifically, additional variant *Yarrowia* ALK2 promoter regions may be constructed, wherein the DNA sequence of the promoter has one or more nucleotide substitutions (i.e., deletions, insertions, substitutions, or addition of one or more nucleotides in the sequence) which do not affect (in particular, impair) the yeast promoter activity. Regions that can be modified without significantly affecting the yeast promoter activity can be identified by deletion studies. A variant promoter of the present invention has at least about 10%, more preferably at least about 20%, more preferably at least about 40%, more preferably at least about 60%, more preferably at least about 80%, more preferably at least about 90%, more preferably at least about 100%, more preferably at least about 200%, more preferably at least about 300% and most preferably at least about 500% of the promoter activity of any of the *Yarrowia* ALK2 promoter regions described herein as SEQ ID NO:7, SEQ ID NO:11, SEQ ID NO:27, SEQ ID NO:15, SEQ ID NO:47, SEQ ID NO:43, SEQ ID NO:39, SEQ ID NO:35, SEQ ID NO:31, SEQ ID NO:19, SEQ ID NO:49, SEQ ID NO:51, SEQ ID NO:53, and SEQ ID NO:55.

U.S. Pat. No. 7,259,255 describes a variety of methods for mutagenesis, suitable for the generation of mutant promoters. This would permit production of a putative promoter having, for example, a more desirable level of promoter activity in the host cell or a more desirable sequence for purposes of cloning (e.g., removal of a restriction enzyme site within the native promoter region). Similarly, the cited reference also discusses means to examine regions of a nucleotide of interest important for promoter activity (i.e., functional analysis via deletion mutagenesis to determine the minimum portion of the putative promoter necessary for activity).

All variant promoter regions of an ALK2 *Yarrowia* gene, derived from the promoter regions described herein, are within the scope of the present disclosure.

Similarly, it should be noted that one could isolate regions upstream of the ALK2 translation initiation codon in various *Yarrowia* species and strains, other than the region isolated herein from *Yarrowia lipolytica* ATCC #20362, and thereby identify alternate promoter regions of an ALK2 *Yarrowia* gene. As is well known in the art, isolation of homologous promoter regions or genes using sequence-dependent protocols is readily possible using various techniques (see, U.S. Pat. No. 7,259,255). Examples of sequence-dependent protocols useful to isolate homologous promoter regions include, but are not limited to: 1) methods of nucleic acid hybridization; 2) methods of DNA and RNA amplification, as exemplified by various uses of nucleic acid amplification technologies [e.g., polymerase chain reaction ["PCR"], Mullis et al., U.S. Pat. No. 4,683,202; ligase chain reaction ["LCR"], Tabor, S. et al., *Proc. Acad. Sci. U.S.A.*, 82:1074 (1985); or strand displacement amplification (SDA), Walker, et al., *Proc. Natl. Acad. Sci. U.S.A.*, 89:392 (1992)]; 3) methods of library construction and screening by complementation; and, 4) methods of genome sequencing. Based on sequence conservation between related organisms, one would expect that the promoter regions would likely share significant homology (i.e., at least about 70-85% identity, more preferably at least about 85-90% identity and more preferably at least about 90-95% identity); however, one or more differences in nucleotide sequence could be observed when aligned with promoter regions of comparable length derived from the upstream region of SEQ ID NO:2. For example, one of skill in the art could readily isolate the *Yarrowia* ALK2 promoter region from any of the various *Y. lipolytica* strains available through the American Type Culture Collection ["ATCC"], including, for example #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847. Similarly, the following strains of *Yarrowia lipolytica* could be obtained from the Herman J. Phaff Yeast Culture Collection, University of California Davis (Davis, Calif.): *Y. lipolytica* 49-14, *Y. lipolytica* 49-49, *Y. lipolytica* 50-140, *Y. lipolytica* 50-46, *Y. lipolytica* 50-47, *Y. lipolytica* 51-30, *Y. lipolytica* 60-26, *Y. lipolytica* 70-17, *Y. lipolytica* 70-18, *Y. lipolytica* 70-19, *Y. lipolytica* 70-20, *Y. lipolytica* 74-78, *Y. lipolytica* 74-87, *Y. lipolytica* 74-88, *Y. lipolytica* 74-89, *Y. lipolytica* 76-72, *Y. lipolytica* 76-93, *Y. lipolytica* 77-12T and *Y. lipolytica* 77-17. Or, strains could be obtained from the Laboratoire de Microbiologie et Génétique Moléculaire of Dr. Jean-Marc Nicaud, INRA Centre de Grignon, France, including for example, *Yarrowia lipolytica* JMY798 (Mlíčková, K. et al., *Appl Environ Microbiol.* 70(7): 3918-24 (2004)), *Y. lipolytica* JMY399 (Barth, G., and C. Gaillardin. In, *Nonconventional Yeasts In Biotechnology*; Wolf, W. K., Ed.; Springer-Verlag: Berlin, Germany, 1996; pp 313-388) and *Y. lipolytica* JMY154 (Wang, H. J., et al., *J. Bacteriol.* 181(17):5140-8 (1999)).

In general, microbial expression systems and expression vectors containing regulatory sequences that direct high level expression of foreign proteins are well known to those skilled in the art. Any of these could be used to construct chimeric genes, which could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products, the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination, i.e., a terminator. It is most preferred when both control regions are derived from genes from the transformed yeast cell, although they need not be derived from genes native to the host.

Herein, transcriptional control regions (also initiation control regions or promoters) that are useful to drive expression of a coding gene of interest in the desired yeast cell are those promoter regions of an ALK2 *Yarrowia* gene, as described supra. Once the promoter regions are identified and isolated, they may be operably linked to a coding region of interest to create a chimeric gene. The chimeric gene may then be expressed in a suitable expression vector in transformed yeast cells, particularly in the cells of oleaginous yeast (e.g., *Yarrowia lipolytica*).

Coding regions of interest to be expressed in transformed yeast cells may be either endogenous to the host or heterologous. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, signal transduction proteins, transcription factors, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalyases, cellulases, chitinases, cutinases, cyclodextrin glycosyltransferases, deoxyribonucleases, esterases, alpha-galactosidases, beta-glucanases, beta-galactosidases, glucoamylases, alpha-glucosidases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases or xylanases.

Thus, one aspect of the present disclosure provides a recombinant construct comprising a *Yarrowia* ALK2 promoter region, as well as recombinant expression vectors comprising the recombinant construct. The ALK2 promoter may also be comprised within a chimeric gene.

Also provided herein is a method for the expression of a coding region of interest in a transformed yeast cell comprising:
  a) providing a transformed yeast cell having a recombinant construct, wherein the recombinant construct comprises:
    (1) a promoter region of an ALK2 *Yarrowia* gene; and
    (2) a coding region of interest which is expressible in the yeast cell;
      wherein the promoter region is operably linked to the coding region of interest; and
  b) growing the transformed yeast cell of step (a) under conditions whereby the recombinant construct is expressed.

The polypeptide so produced by expression of the recombinant construct may optionally be recovered from the culture.

In some embodiments herein, preferred coding regions of interest are those encoding enzymes involved in the production of microbial oils, including omega-6 and omega-3 fatty acids (i.e., omega-6 and omega-3 fatty acid biosynthetic pathway enzymes). Thus, preferred coding regions include those encoding desaturases (e.g., delta-8 desaturases, delta-5 desaturases, delta-17 desaturases, delta-12 desaturases, delta-4 desaturases, delta-6 desaturases, delta-15 desaturases and delta-9 desaturases) and elongases (e.g., $C_{14/16}$ elongases, $C_{16/18}$ elongases, $C_{18/20}$ elongases, $C_{20/22}$ elongases, delta-6 elongases and delta-9 elongases).

More specifically, the omega-3/omega-6 fatty acid biosynthetic pathway is illustrated in FIG. 3. All pathways require the initial conversion of oleic acid [18:1] to linoleic acid ["LA"; 18:2], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"; 20:2] by a delta-9 elongase; 2) EDA is converted to dihomo-gamma-linolenic acid ["DGLA"; 20:3] by a delta-8 desaturase; 3) DGLA is converted to arachidonic acid ["ARA"; 20:4] by a delta-5 desaturase; 4) ARA is converted to docosatetraenoic acid ["DTA"; 22:4] by a $C_{20/22}$ elongase; and, 5) DTA is converted to docosapentaenoic acid ["DPAn-6"; 22:5] by a delta-4 desaturase. To clarify, "omega-6 fatty acids" are polyunsaturated fatty acids having the first unsaturated double bond six carbon atoms from the omega (methyl) end of the molecule and additionally having a total of two or more double bonds, with each subsequent unsaturation occurring 3 additional carbon atoms toward the carboxyl end of the molecule.

The "delta-9 elongase/delta-8 desaturase pathway" can also use alpha-linolenic acid ["ALA"; 18:3] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"; 20:3] by a delta-9 elongase; 3) ETrA is converted to eicosatetraenoic acid ["ETA"; 20:4] by a delta-8 desaturase; 4) ETA is converted to eicosapentaenoic acid ["EPA"; 20:5] by a delta-5 desaturase; 5) EPA is converted to docosapentaenoic acid ["DPA"; 22:5] by a $C_{20/22}$ elongase; and, 6) DPA is converted to docosahexaenoic acid ["DHA"; 22:6] by a delta-4 desaturase. Optionally, omega-6 fatty acids may be converted to omega-3 fatty acids. For example, ETA and EPA are produced from DGLA and ARA, respectively, by delta-17 desaturase activity. To clarify, "omega-3 fatty acids" are polyunsaturated fatty acids having the first unsaturated double bond three carbon atoms away from the omega end of the molecule and additionally having a total of three or more double bonds, with each subsequent unsaturation occurring 3 additional carbon atoms toward the carboxyl end of the molecule.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"; 18:4], respectively, by a delta-6 desaturase; then, a $C_{18/20}$ elongase converts GLA to DGLA and/or STA to ETA. Downstream PUFAs are subsequently formed as described above.

One of skill in the art will appreciate that the disclosure herein also provides a method for the production of an omega-3 fatty acid or omega-6 fatty acid comprising:
  a) providing a transformed oleaginous yeast comprising a recombinant construct, wherein the recombinant construct comprises:
    i) a promoter region of an ALK2 *Yarrowia* gene; and
    ii) a coding region encoding at least one omega-3 fatty acid or omega-6 fatty acid biosynthetic pathway enzyme;
      wherein the promoter region and the coding region are operably linked; and
  b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
  c) optionally recovering the omega-3 fatty acid or the omega-6 fatty acid.

The omega-3 fatty acid or the omega-6 fatty acid may be selected from the group consisting of: LA, GLA, EDA, DGLA, ARA, DTA, DPAn-6, ALA, STA, ETrA, ETA, EPA, DPAn-3 and DHA.

Once a DNA cassette (e.g., comprising a chimeric gene comprising a promoter region of an ALK2 *Yarrowia* gene, ORF and terminator) suitable for expression in a yeast cell has been obtained, it is placed in a plasmid vector capable of autonomous replication in the yeast cell, or it is directly integrated into the genome of the yeast cell. Integration of expression cassettes can occur randomly within the yeast genome or can be targeted through the use of constructs containing regions of homology with the yeast genome sufficient to target recombination to a specific locus. All or some of the transcriptional and translational regulatory regions can be provided by the endogenous locus where constructs are targeted to an endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced chimeric genes are expressed at the necessary levels to provide for synthesis of the desired products.

U.S. Pat. No. 7,259,255 describes means to increase expression of a particular coding region of interest.

Constructs comprising the chimeric gene(s) of interest may be introduced into a yeast cell by any standard technique. These techniques include transformation (e.g., lithium acetate transformation [*Methods in Enzymology*, 194:186-187 (1991)]), protoplast transformation, bolistic impact, electroporation, microinjection, or any other method that introduces the chimeric gene(s) of interest into the yeast cell.

For convenience, a yeast cell that has been manipulated by any method to take up a DNA sequence, for example, in an expression cassette, is referred to herein as "transformed", "transformant" or "recombinant" (as these terms will be used interchangeably herein). The transformed yeast will have at least one copy of the expression construct and may have two or more, depending upon whether the expression cassette is integrated into the genome or is present on an extrachromosomal element having multiple copy numbers.

The transformed yeast cell can be identified by various selection techniques, as described in U.S. Pat. Nos. 7,238,482, 7,259,255 and 7,932,077.

Following transformation, substrates upon which the translated products of the chimeric genes act may be produced by the yeast either naturally or transgenically, or they may be provided exogenously.

Yeast cells for expression of the instant chimeric genes comprising a promoter region of an ALK2 *Yarrowia* gene may include yeast that grow on a variety of feedstocks, including simple or complex carbohydrates, fatty acids, organic acids, oils, glycerol and alcohols, and/or hydrocarbons over a wide range of temperature and pH values. It is contemplated that because transcription, translation and the protein biosynthetic apparatus are highly conserved, any yeast will be a suitable host for expression of the present chimeric genes.

As previously noted, yeast do not form a specific taxonomic or phylogenetic grouping, but instead comprise a diverse assemblage of unicellular organisms that occur in the Ascomycotina and Basidiomycotina, most of which reproduce by budding (or fission) and derive energy via fermentation processes. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

In preferred embodiments, the transformed yeast is an oleaginous yeast. These organisms are naturally capable of oil synthesis and accumulation, wherein the oil can comprise greater than about 25% of the dry cell weight, more preferably greater than about 30% of the dry cell weight, more preferably greater than about 40% of the dry cell weight, more preferably greater than about 50% of the dry cell weight, and most preferably greater than about 60% of the dry cell weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis,* and *Yarrowia lipolytica* (formerly classified as *Candida lipolytica*). Alternately, oil biosynthesis may be genetically engineered such that the transformed yeast can produce more than 25% oil of the dry cell weight, and thereby be considered oleaginous.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)). The *Y. lipolytica* strain designated as ATCC #20362 was the particular strain from which the ALK2 *Yarrowia* gene and promoter regions encompassed within SEQ ID NO:1 were isolated.

Specific teachings applicable for transformation of oleaginous yeasts (i.e., *Yarrowia lipolytica*) via integration techniques based on linearized fragments of DNA include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for expression of omega-3 fatty acid or omega-6 fatty acid biosynthetic pathway enzymes in the oleaginous yeast *Y. lipolytica* are described in U.S. Pat. Nos. 7,238,482, 7,550,286, 7,588,931, 7,932,077, U.S. Pat. Appl. Publ. No. 2009-0093543-A1, and U.S. Pat. Appl. Publ. No. 2010-0317072-A1, each incorporated herein by reference in their entirety.

The transformed yeast cell is grown under conditions that optimize expression of the chimeric gene(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media suitable for the transformed yeast described herein should contain a suitable carbon source. Suitable carbon sources may include, but are not limited to: monosaccharides, disaccharides, oligosaccharides, polysaccharides, sugar alcohols, mixtures from renewable feedstocks, alkanes, fatty acids, esters of fatty acids, glycerol, monoglycerides, diglycerides, triglycerides, phospholipids, various commercial sources of fatty acids, and one-carbon sources, such as are described in U.S. Pat. No. 7,259,255. Hence it is contemplated that the source of carbon utilized may encompass a wide variety of carbon-containing sources and will only be limited by the choice of the yeast species. Although all of the above mentioned carbon sources and mixtures thereof are expected to be suitable herein, preferred carbon sources are sugars (e.g., glucose, invert sucrose, sucrose, fructose and combinations thereof), glycerols, and/ or fatty acids (see U.S. Pat. Appl. Publ. No. 2011-0059204 A1).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the transformed yeast (and optionally, promotion of the enzymatic pathways necessary for omega-3/omega-6 fatty acid production). Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and transformed yeast cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of omega-3/ omega-6 fatty acids in oleaginous yeast cells requires a two-stage process, since the metabolic state must be "balanced" between growth and synthesis/storage of fats. Thus, most preferably, a two-stage fermentation process is necessary for the production of omega-3/omega-6 fatty acids in oleaginous yeast (e.g., *Yarrowia lipolytica*). This approach is described in U.S. Pat. No. 7,238,482.

Host cells comprising a suitable coding region of interest operably linked to promoter regions of an ALK2 *Yarrowia* gene may be cultured using methods known in the art. For example, the cell may be cultivated by shake flask cultivation or small-/large-scale fermentation in laboratory or industrial fermentors performed in a suitable medium and under conditions allowing expression of the coding region of interest. Similarly, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process (see U.S. Pat. No. 7,259,255).

EXAMPLES

The present invention is further described in the following Examples, which illustrate reductions to practice of the invention but do not completely define all of its possible variations.
General Methods Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), New England Biolabs (Ipswich, Mass.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s) and "kB" means kilobase(s).

Nomenclature For Expression Cassettes: The structure of an expression cassette will be represented by a simple notation system of "X::Y::Z", wherein X describes the promoter fragment, Y describes the gene fragment, and Z describes the terminator fragment, which are all operably linked to one another.

Transformation And Cultivation Of *Yarrowia lipolytica: Y. lipolytica* strains with ATCC Accession Nos. #20362, #76982 and #90812 were purchased from the American Type Culture Collection (Rockville, Md.). *Y. lipolytica* strains were typically grown at 28-30° C. Agar plates were prepared as required by addition of 20 g/L agar to the liquid media, according to standard methodology.

Example 1

Isolation of the 5' Upstream Regions of the ALK2 Gene from *Yarrowia lipolytica*

According to the DNA sequence of the *Yarrowia* ALK2 locus (ORF "YALI0F01320g", Dujon, B. et al., *Nature*, 430 (6995):35-44 (2004), SEQ ID NO:1 herein), the 1 kB length 5' upstream sequence from the nucleotide 'A' (designated as +1) of the translation initiation codon 'ATG' was assumed to encode the promoter region (designated herein as ALK2F, SEQ ID NO:2).

In order to study the promoter region upstream of the ALK2 gene, oligonucleotides Y1198 (SEQ ID NO:3) and Y1199 (SEQ ID NO:4) were designed as primers to amplify a 942 bp fragment, comprising an 876 bp 5' upstream sequence from the nucleotide 'A' of the translation initiation codon 'ATG' and the first 66 bp of the coding region of the ALK2 gene. A ClaI site was included at the 5' portion of oligonucleotide Y1198 (SEQ ID NO:3). In order to incorporate an NcoI site at the 3' end of the 942 bp fragment, a cytosine ['C'] nucleotide was substituted for the guanine ['G'] nucleotide at position +66 of the ALK2 gene in oligonucleotide Y1199 (SEQ ID NO:4). The guanine ['G'] to cytosine ['C'] mutation did not affect the resulting translated amino acid sequence (i.e., both the wild-type ACG and mutated ACC codons encode a threonine residue).

The 942 bp DNA sequence (comprising the 876 bp 5' upstream sequence and the first 66 bp of the ALK2 coding region) of the ALK2 gene was amplified using *Y. lipolytica* strain ATCC #20362 genomic DNA as template and oligonucleotides Y1198 and Y1199 as primers. The PCR amplification was carried out in a 50 l total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100g/mL BSA (final concentration), 200 μM each deoxyribonucleotide triphosphate, 10 pmole of each primer and 1 μl of Pfu DNA polymerase (Stratagene, San Diego, Calif.)). The thermocycler conditions were set for 35 cycles at 95° C. for 1 min, 56° C. for 30 sec, and 72° C. for 1 min, followed by a final extension at 72° C. for 10 min.

The PCR product comprising the 942 bp fragment of the ALK2 gene was purified using a Qiagen PCR purification kit, followed by gel electrophoresis in 1% (weight/volume) agarose. The product was then cloned into the pCR4TOPO vector (Invitrogen, San Diego, Calif.). The ligated DNA sample was used to transform *E. coli* DH5α cells individually, and transformants were selected on LB agar containing ampicillin (100g/mL).

Analyses of the plasmid DNA from transformants confirmed the presence of a 942 bp fragment. The plasmid containing the 942 bp DNA fragment was designated pT-ALK2Pro (SEQ ID NO:5). Sequence analyses showed that pT-ALK2Pro contained a fragment of 942 bp (designated as ALK2N; SEQ ID NO:6), comprising the 876 bp 5' upstream sequence from the nucleotide 'A' of the translation initiation codon 'ATG' of the ALK2 gene and the first 66 bp of the coding region of the ALK2 gene. The 876 bp 5' upstream sequence of the ALK2 gene was designated as ALK2L (wherein the "L" is for "long"; SEQ ID NO:7).

Example 2

Modification to ALK2L: Synthesis of Promoters 876 bp ALK2LM, 834 bp ALK2LM1, and 767 bp ALK2LM-C The present Example describes the synthesis of plasmids pT-ALK2Pro-(S), pT-ALK2Pro-(S)S and pT-ALK2Pro-(S)C, each comprising a modified ALK2L promoter based on removal or insertion of a specific restriction enzyme site, respectively.

Specifically, plasmid pT-ALK2Pro-(S) (SEQ ID NO:8) was generated by site-directed mutagenesis using plasmid pT-ALK2Pro (Example 1) as template, and oligonucleotides Y1202 (SEQ ID NO:9) and Y1203 (SEQ ID NO:10) as primers. The internal SphI site (i.e., GCATGC at nucleotides 752-757 of SEQ ID NO:7) of the ALK2L promoter was mutated into GGATGC in plasmid pT-ALK2Pro-(S) (SEQ ID NO:8). The modified ALK2L promoter lacking the internal SphI site within plasmid pT-ALK2Pro-(S) was designated as 876 bp ALK2LM (wherein the "LM" is for "long, modified"; SEQ ID NO:11).

Plasmid pT-ALK2Pro-(S)S was generated by site-directed mutagenesis using plasmid pT-ALK2Pro-(S) plasmid as template, and oligonucleotides Y1208 (SEQ ID NO:13) and Y1209 (SEQ ID NO:14) as primers. A SwaI site was added by substituting an 'AA' nucleotide sequence for the 'TT' nucleotide sequence at positions 41 and 42 of the ALK2LM (SEQ ID NO:11) promoter in plasmid pT-ALK2Pro-(S)S (SEQ ID NO:12). The 834 bp 5' upstream sequence of the ALK2 gene in plasmid pT-ALK2Pro-(S)S was designated as 834 bp ALK2LM1 (SEQ ID NO:15).

Plasmid pT-ALK2Pro-(S)C was generated by site-directed mutagenesis using plasmid pT-ALK2Pro-(S) as template, and oligonucleotides Y1262 (SEQ ID NO:17) and Y1263 (SEQ ID NO:18) as primers. A ClaI site was generated by insertion of the nucleotide sequence 'TCG' between positions 109 and 110 of the ALK2LM promoter in plasmid pT-ALK2Pro-(S)C (SEQ ID NO:16). The 767 bp 5' upstream sequence of the ALK2 gene in plasmid pT-ALK2Pro-(S)C was designated as 767 bp ALK2LM-C (SEQ ID NO:19).

Example 3

Synthesis and Transformation of an Expression Plasmid Comprising the 834 bp ALK2LM1 Promoter To perform comparative studies investigating the activity of the 834 bp ALK2LM1 promoter, an expression plasmid was created such that the ALK2LM1 promoter and the first 66 bp of N-terminal protein coding region of the ALK2 gene were operably linked to a reporter gene (i.e., the *E. coli* gene encoding β-glucuronidase ("GUS"; Jefferson, R. A., *Nature*, 342(6251):837-838 (1989)).

U.S. Pat. No. 7,202,356 describes the synthesis of pDMW212 (FIG. 4A and SEQ ID NO:21 herein), comprising a recombinant FBA::GUS::XPR2 construct. More specifically, this expression cassette comprises an FBA promoter fragment (i.e., 5' upstream untranslated region in front of the 'ATG' translation initiation codon of a fructose-bisphosphate aldolase enzyme [E.C. 4.1.2.13] encoded by the fba1 gene and that is necessary for expression), a GUS reporter gene fragment and an XPR2 terminator fragment (comprising ~100 bp of the 3' region of the *Yarrowia* Xpr gene (GenBank Accession No. M17741)), which are all operably linked to one another.

The PmeI/NcoI fragment of pDMW212 (comprising the FBA promoter within the recombinant FBA::GUS::XPR2 construct) was replaced with the 834 bp ALK2LM1 promoter and the 66 bp N-terminal protein coding region of the ALK2 gene. Specifically, the SwaI/NcoI fragment of pT-ALK2Pro-(S)S (Example 2), comprising the 834 bp ALK2LM1 promoter and the 66 bp N-terminal protein coding region ("N-22 AA") of the ALK2 gene were ligated with the PmeI/NcoI linearized pDMW212 fragment, thereby creating plasmid pALK2GUS (FIG. 4B; SEQ ID NO:20) comprising a recombinant 834 bp ALK2LM1 promoter plus 66 bp N-terminal ALK2 gene coding region::GUS::XPR construct. Thus, plasmid pALK2GUS contains the following components:

TABLE 3

Description of Plasmid pALK2GUS

| RE Sites and Nucleotide position in SEQ ID NO: 20 | Description of Fragment and Recombinant Construct Components |
|---|---|
| 'GTTTAAAT' (product of ligating SwaI- and PmeI-cut blunt ends)/SacI (8514-2023) | ALK2LM1/N-22 AA::GUS::XPR, comprising: 834 bp *Y. lipolytica* ALK2LM1 promoter plus 66 bp N-terminal protein coding sequence ("N-22 AA") of the ALK2 gene (SEQ ID NO: 15); GUS: *E. coli* beta-D-glucuronidase (GenBank Accession No. AAA68923); XPR2: ~100 bp of the 3' region of Xpr gene of *Y. lipolytica* (GenBank Accession No. M17741) |
| 3163-2283 | ColE1 plasmid origin of replication |
| 4093-3233 | Ampicillin-resistance gene (Amp$^R$) for selection in *E. coli* |
| EcoRI/SphI (4923-6269) | ARS18: *Y. lipolytica* centromere and autonomously replicatin sequence 18 (GenBank Accession No. M91600) |
| SalI/SphI (8505-6269) | Leu2: beta-isopropylmalate dehydrogenase gene of *Y. lipolytica* (GenBank Accession No. M37309) |

*Y. lipolytica* strain Y4001 has been described in U.S. Pat. No. 7,709,239 (Example 3 therein). Strain Y4001, derived from *Yarrowia lipolytica* ATCC #20362, was capable of producing about 17% eicosadienoic acid ["EDA"; 20:2 omega-6] relative to the total lipids. The final genotype of strain Y4001 with respect to wild type *Y. lipolytica* ATCC #20362 was: Leu-, GPD::FmD12::Pex20, EXP1::EgD9e::Lip1, FBAINm::EgD9eS::Lip2 and YAT1::ME3S::Pex16. Abbreviations are as follows: FmD12 is a *Fusarium moniliforme* delta-12 desaturase gene [U.S. Pat. No. 7,504,259]; ME3S is a codon-optimized $C_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; and, EgD9eS is a codon-optimized delta-9 elongase gene, derived from *E. gracilis* [U.S. Pat. No. 7,645,604].

Plasmids pALK2GUS and pDMW212 were transformed separately into *Y. lipolytica* strain Y4001 according to the method of Chen, D. C. et al. (*Appl. Microbiol Biotechnol.*, 48(2):232-235 (1997)) and as described in U.S. Pat. No. 7,709,239.

Transformed cells were plated onto Minimal Media ["MM"] plates lacking leucine and maintained at 30° C. for 2 to 3 days (MM comprises per liter: 20g glucose, 1.7 g yeast nitrogen base without amino acids, 1.0 g proline, and pH 6.1 (do not need to adjust)). Thus, transformants were obtained comprising pALK2GUS and pDMW212 plasmids, respectively.

Example 4

Comparative Analyses Of 834 bp ALK2LM1 And FBA Promoter Activities In *Yarrowia lipolytica* Strain Y4001

The promoter activities of the 834 bp ALK2LM1 promoter (SEQ ID NO:15) and the FBA promoter were determined in *Yarrowia* transformants containing plasmids pALK2GUS and pDMW212, respectively, based on expression of the GUS reporter gene as measured by histochemical assays (Jefferson, R. A. *Plant Mol. Biol. Reporter* 5:387-405 (1987)).

Specifically, *Y. lipolytica* transformants containing plasmids pALK2GUS and pDMW212 respectively were grown from single colonies in 3 mL MM at 30° C. for 2 days. Then, 1 mL of cells was collected by centrifugation. The remaining cultures were centrifuged and washed 2 times with High Glucose Media ["HGM"], resuspended in 3 mL each of HGM and allowed to grow at 30° C. for another 5 days (HGM comprises per liter: 80g glucose, 2.58 g $KH_2PO_4$ and 5.36 g $K_2HPO_4$, pH 7.5 (do not need to adjust)). Cell samples from cultures grown 2 days in MM, as well as cultures grown 2 days in MM and 5 days in HGM were collected by centrifugation, resuspended in 100 ml of histochemical staining buffer, and incubated at 30° C. Staining buffer was prepared by dissolving 5 mg of 5-bromo-4-chloro-3-indolyl glucuronide ["X-Gluc"] in 50 ml dimethyl formamide, followed by the addition of 5 mL 50 mM $NaPO_4$, pH 7.0.

The results (FIG. 5) of histochemical staining showed that the 834 bp ALK2LM1 promoter in construct pALK2GUS had almost no activity when the transformed *Yarrowia* cells were grown in MM media. By contrast, very strong expression was observed in *Yarrowia* strains growing in nitrogen-limited HGM media. As expected, the constitutive FBA promoter in construct pDMW212 demonstrated strong activity when pDMW212-transformed cells were grown in either MM or nitrogen-limited HGM media.

Based on the above results, one of skill in the art will therefore recognize that the ALK2LM1 promoter set forth in SEQ ID NO:15 is a strong inducible promoter useful for expression of heterologous and/or homologous genes in transformed yeast, including *Yarrowia*.

Example 5

Synthesis and Transformation of Expression Plasmids pALK2GUS-C, pALK2GUS-S, pALK2GUS-P, pALK2GUS-P1, pALK2GUS-P2, pALK2GUS-P5, and pALK2GUS-P6 Comprising 767 bp ALK2LM-C, 838 bp ALK2LM1-S, 835 bp ALK2LM-P, 835 bp ALK2LM1-PP1, 837 bp ALK2LM1-PP2, 839 bp ALK2LM1-PP5, and 840 bp ALK2LM1-PP6 Promoters Comparative studies were performed to investigate the promoter activity of modified ALK2 promoters having lengths of 767 bp, 838 bp, 835 bp, 835 bp, 837 bp, 839 bp, or 840 bp. Expression plasmids pALK2GUS-C, pALK2GUS-S, pALK2GUS-P, pALK2GUS-P1, pALK2GUS-P2, pALK2GUS-P5, and pALK2GUS-P6 were created, respectively, each comprising a modified ALK2 promoter operably linked to the GUS reporter gene.

Figure 4B:
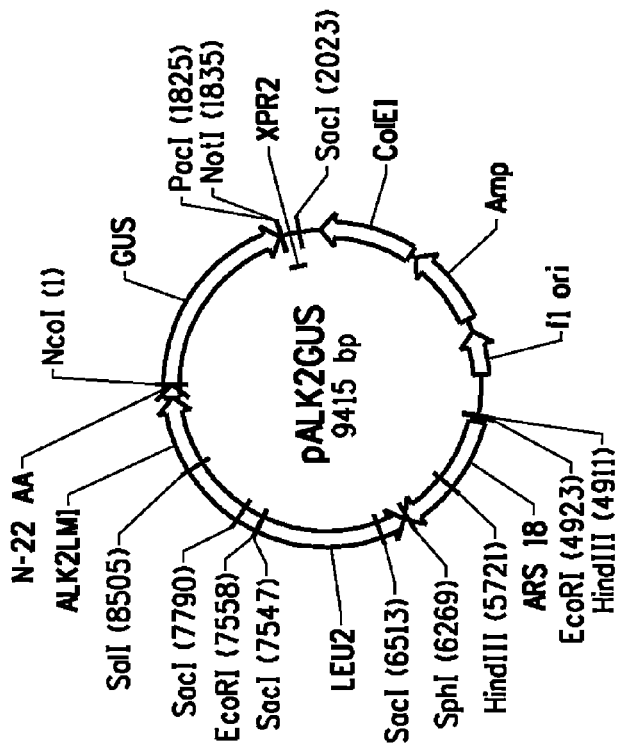
Figure 4A:
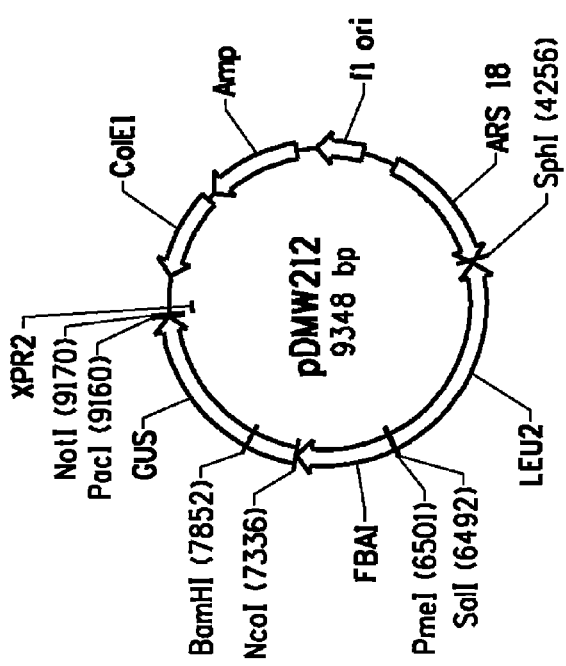

First, the ClaI/NcoI fragment of pDG2LGUS (Example 3 and FIG. 4B of U.S. Appl. No. 61/469,933, filed Mar. 31, 2011; SEQ ID NO:22 herein) was replaced with the 767 bp ClaI/NcoI fragment of pT-ALK2Pro-(S)C (designated ALK2LM-C, SEQ ID NO:19). Specifically, the ClaI/NcoI fragment of pT-ALK2Pro-(S)C (Example 2), comprising the 767 bp ALK2LM-C promoter and the 66 bp N-terminal protein coding region of the ALK2 gene, was ligated with the ClaI/NcoI linearized pDG2GUS fragment, thereby creating plasmid pALK2GUS-C (SEQ ID NO:23) comprising a recombinant 767 bp ALK2LM-C plus 66 bp N-terminal protein coding sequence of the ALK2 gene +::GUS::XPR2 construct.

Second, site-directed mutagenesis was performed using pALK2GUS as template, and oligonucleotides Y2148 (SEQ ID NO:24) and Y2149 (SEQ ID NO:25) as primers. Specifically, primer Y2148 was designed to insert four nucleotides (i.e., 'AAAT') between positions 89 and 90 of SEQ ID NO:15, thereby resulting in creation of a SwaI site in the 834 bp ALK2LM1 promoter in the resultant plasmid, pALK2GUS-S (SEQ ID NO:26). The modified ALK2LM1 promoter in pALK2GUS-S was 838 bp in length and was designated as 838 bp ALK2LM1-S (SEQ ID NO:27).

Similarly, site-directed mutagenesis was performed using pALK2GUS as template, and oligonucleotides Y1244 (SEQ ID NO:28) and Y1245 (SEQ ID NO:29) as primers. Specifically, the nucleotide sequence 'AAA' was substituted for the nucleotide sequence 'TT' at positions 34 to 35 of the 834 bp ALK2LM1 promoter, thereby introducing a PmeI site at position +30 to +37 of ALK2LM1 in the resultant plasmid, pALK2GUS-P (SEQ ID NO:30). The modified ALK2LM1 promoter in pALK2GUS-P was 835 bp in length, and was designated as 835 bp ALK2LM1-P (SEQ ID NO:31).

Site-directed mutagenesis was also performed using pALK2GUS-P as template and oligonucleotides Y1250 (SEQ ID NO:32) and Y1251 (SEQ ID NO:33) as primers. Specifically, primer Y1250 was designed to mutate four oligonucleotides (i.e., 'AAAA' to 'GTTT') at positions 590 to 593 of the ALK2LM1-P promoter, thereby resulting in creation of a PmeI site in the 835 bp ALK2LM1-P promoter in the resultant plasmid, pALK2GUS-P1 (SEQ ID NO:34). The modified ALK2LM1-P promoter in pALK2GUS-P1 was 835 bp in length, and was designated as 835 bp ALK2LM1-PP1 (SEQ ID NO:35).

Site-directed mutagenesis was next performed using pALK2GUS-P as template and oligonucleotides Y2158 (SEQ ID NO:36) and Y2159 (SEQ ID NO:37) as primers. Specifically, a PmeI site was introduced by the insertion of the nucleotide sequence 'TA' between positions 471 and 472 of the 835 bp ALK2LM1-P promoter in the resulting plasmid pALK2GUS-P2 (SEQ ID NO:38). The modified ALK2LM1-P promoter in pALK2GUS-P2 was 837 bp in length, and was designated as 837 bp ALK2LM1-PP2 (SEQ ID NO:39).

Site-directed mutagenesis was further performed using pALK2GUS-P as template, and oligonucleotides Y2170 (SEQ ID NO:40) and Y2171 (SEQ ID NO:41) as primers. A PmeI site was introduced by the insertion of the nucleotide sequence 'TTTA' between positions 324 and 325 of the 835 bp ALK2LM1-P promoter in the resulting plasmid, pALK2GUS-P5 (SEQ ID NO:42). The modified ALK2LM1-P promoter in pALK2GUS-P5 was 839 bp in length, and was designated 839 bp ALK2LM1-PP5 (SEQ ID NO:43).

Site-directed mutagenesis was again performed using pALK2GUS-P as template, and oligonucleotides Y2172 (SEQ ID NO:44) and Y2173 (SEQ ID NO:45) as primers. A PmeI site was introduced by insertion of the nucleotide sequence 'TTAAA' between positions 189 and 190 of the 835 bp ALK2LM1-P promoter in the resulting plasmid pALK2GUS-P6 (SEQ ID NO:46). The modified ALK2LM1-P promoter in pALK2GUS-P6 was 840 bp in length, and was designated as 840 bp ALK2LM1-PP6 (SEQ ID NO:47).

Thus, pALK2GUS-C (comprising the 767 bp ALK2LM-C promoter (SEQ ID NO:23) plus 66 bp N-terminal protein coding region of the ALK2 gene::GUS::XPR recombinant construct), pALK2GUS-S (comprising the 838 bp ALK2LM1-S promoter (SEQ ID NO:26) plus 66 bp N-terminal protein coding region of the ALK2 gene::GUS::XPR recombinant construct), pALK2GUS-P (comprising the 835 bp ALK2LM1 promoter (SEQ ID NO:30) plus 66 bp N-terminal protein coding region of the ALK2 gene::GUS::XPR recombinant construct), pALK2GUS-P1 (comprising the 835 bp ALK2LM1-PP1 promoter (SEQ ID NO:34) plus 66 bp N-terminal protein coding region of the ALK2 gene::GUS::XPR recombinant construct), pALK2GUS-P2 (comprising the 837 bp ALK2LM1-PP2 promoter (SEQ ID NO:38) plus 66 bp N-terminal protein coding region of the ALK2 gene:: GUS::XPR recombinant construct), pALK2GUS-P5 (comprising the 839 bp ALK2LM1-PP5 promoter (SEQ ID NO:42) plus 66 bp N-terminal protein coding region of the ALK2 gene::GUS::XPR recombinant construct), and pALK2GUS-P6 (comprising the 840 bp ALK2LM1-PP6 promoter (SEQ ID NO:46) plus 66 bp N-terminal protein coding region of the ALK2 gene::GUS::XPR recombinant construct) are identical expression constructs, with the exception that either a 767 bp ALK2LM-C (SEQ ID NO:19), 838 bp ALK2LM1-S (SEQ ID NO:27), 835 bp ALK2LM-P (SEQ ID NO:31), 835 bp ALK2LM1-PP1 (SEQ ID NO:35), 837 bp ALK2LM1-PP2 (SEQ ID NO:39), 839 bp ALK2LM1-PP5 (SEQ ID NO:43), or 840 bp ALK2LM1-PP6 (SEQ ID NO:47) promoter derived from the 5' upstream region and the 66 bp ALK2 N-terminal protein coding region of the *Y. lipolytica* ALK2 gene was operably linked to the GUS::XPR2 recombinant construct.

Plasmids pALK2GUS, pALK2GUS-C, pALK2GUS-S, pALK2GUS-P, pALK2GUS-P1, pALK2GUS-P2, pALK2GUS-P5, and pALK2GUS-P6 were transformed separately into *Y. lipolytica* strain Y4001 as described in Example 3. Transformant cells were plated onto MM plates lacking leucine and maintained at 30° C. for 2 to 3 days. Thus, transformants were obtained comprising the pALK2GUS-C, pALK2GUS-S, pALK2GUS-P, pALK2GUS-P1, pALK2GUS-P2, pALK2GUS-P5, and pALK2GUS-P6 plasmids, respectively.

Example 6

Comparative Analysis of 834 bp ALK2LM1, 767 bp ALK2LM-C, 838 bp ALK2LM1-S, 835 bp ALK2LM1-P, 835 bp ALK2LM1-PP1, 837 bp ALK2LM1-PP2, 839 bp ALK2LM1-PP5, and 840 bp ALK2LM1-PP6 Promoter Activities in *Yarrowia lipolytica* Strain Y4001

The promoter activities of the 834 bp ALK2LM1 (SEQ ID NO:15), 767 bp ALK2LM-C (SEQ ID NO:19), 838 bp ALK2LM1-S (SEQ ID NO:27), 835 bp ALK2LM1-P (SEQ ID NO:31), 835 bp ALK2LM1-PP1 (SEQ ID NO:35), 837 bp ALK2LM1-PP2 (SEQ ID NO:39), 839 bp ALK2LM1-PP5 (SEQ ID NO:43), and 840 bp ALK2LM1-PP6 (SEQ ID NO:47) promoters were determined in *Yarrowia* transformants containing pALK2GUS, pALK2GUS-C, pALK2GUS-S, pALK2GUS-P, pALK2GUS-P1, pALK2GUS-P2, pALK2GUS-P5, and pALK2GUS-P6, respectively. GUS activity in each expression construct was measured by histochemical assays as described in Example 4.

The results of histochemical staining showed that the promoter activities of 767 bp ALK2LM-C (SEQ ID NO:19), 838 bp ALK2LM1-S (SEQ ID NO:27), 835 bp ALK2LM1-P (SEQ ID NO:31), 835 bp ALK2LM1-PP1 (SEQ ID NO:35), 837 bp ALK2LM1-PP2 (SEQ ID NO:39), 839 bp ALK2LM1-PP5 (SEQ ID NO:43), and 840 bp ALK2LM1-PP6 (SEQ ID NO:47), were equivalent to the 834 bp ALK2LM1 (SEQ ID NO:15, Example 4) promoter. Specifically, each of the promoters was almost completely inactive when their respective, transformed *Yarrowia* cells were grown in MM, but were very strongly active when their constructs were expressed by cells grown in nitrogen-limited HGM media. These results indicated that the promoter activities of the 767 bp ALK2LM-C, 838 bp ALK2LM1-S, 835 bp ALK2LM1-P, 835 bp ALK2LM1-PP1, 837 bp ALK2LM1-

PP2, 839 bp ALK2LM1-PP5, and 840 bp ALK2LM1-PP6 promoters were not affected by the various modifications performed in Example 5.

Example 7

Synthesis and Transformation of Expression Plasmids pALK2GUS-P8, pALK2GUS-P7, pALK2GUS-P3, and pALK2GUS-P4 Comprising 646 bp ALK2LM-P8, 511 bp ALK2GUS-P7, 364 bp ALK2GUS-P3, and 242 bp ALK2GUS-P4 Promoters Comparative studies were performed to investigate the promoter activity of truncated ALK2 promoters having lengths of 646 bp, 511 bp, 364 bp, and 242 bp, using expression plasmids pALK2GUS-P8, pALK2GUS-P7, pALK2GUS-P3, and pALK2GUS-P4, respectively.

Plasmid pALK2GUS-P6 (Example 5, SEQ ID NO:46) was digested with PmeI, and the large PmeI fragment of pALK2GUS-P6 was self-ligated to generate pALK2GUS-P8 (SEQ ID NO:48). The ALK2 promoter fragment in pALK2GUS-P8 was 646 bp in length and was designated as 646 bp ALK2LM-P8 (SEQ ID NO:49).

Plasmid pALK2GUS-P5 (Example 5, SEQ ID NO:42) was digested with PmeI, and the large PmeI fragment of pALK2GUS-P5 was self-ligated to generate pALK2GUS-P7 (SEQ ID NO:50). The ALK2 promoter fragment in pALK2GUS-P7 was 511 bp in length and was designated as 511 bp ALK2LM-P7 (SEQ ID NO: 51).

Plasmid pALK2GUS-P2 (Example 5, SEQ ID NO:38) was digested with PmeI, and the large PmeI fragment of pALK2GUS-P2 was self-ligated to generate pALK2GUS-P3 (SEQ ID NO:52). The ALK2 promoter fragment in pALK2GUS-P3 was 364 bp in length and was designated as 364 bp ALK2LM-P3 (SEQ ID NO:53)

Plasmid pALK2GUS-P1 (Example 5, SEQ ID NO:34) was digested with PmeI, and the large PmeI fragment of pALK2GUS-P1 was self-ligated to generate pALK2GUS-P4 (SEQ ID NO:54). The ALK2 promoter fragment in pALK2GUS-P4 was 242 bp in length and was designated as 242 bp ALK2LM-P4 (SEQ ID NO:55).

Thus, plasmids pALK2GUS (Example 3, comprising the 834 bp ALK2LM1 promoter (SEQ ID NO:20) plus 66 bp N-terminal protein coding region of the ALK2 gene::GUS::XPR recombinant construct), pALK2GUS-P8 (comprising the 646 bp ALK2LM-P8 promoter (SEQ ID NO:48) plus 66 bp N-terminal protein coding region of the ALK2 gene::GUS::XPR recombinant construct), pALK2GUS-P7 (comprising the 511 bp ALK2LM-P7 promoter (SEQ ID NO:50) plus 66 bp N-terminal protein coding region of the ALK2 gene::GUS::XPR recombinant construct), pALK2GUS-P3 (comprising the 364 bp ALK2LM-P3 promoter (SEQ ID NO:52) plus 66 bp N-terminal protein coding region of the ALK2 gene::GUS::XPR recombinant construct), and pALK2GUS-P4 (comprising the 242 bp ALK2LM-P4 promoter (SEQ ID NO:54) plus 66 bp N-terminal protein coding region of the ALK2 gene::GUS::XPR recombinant construct) are identical expression constructs, with the exception that either an 834 bp ALK2LM1, 646 bp ALK2LM-P8, 511 bp ALK2GUS-P7, 364 bp ALK2GUS-P3, or 242 bp ALK2GUS-P4 promoter derived from the 5' upstream region and the 66 bp ALK2 N-terminal protein coding region of the *Y. lipolytica* ALK2 gene was operably linked to the GUS::XPR2 recombinant construct.

Plasmids pALK2GUS, pALK2GUS-P8, pALK2GUS-P7, pALK2GUS-P3, and pALK2GUS-P4 were transformed separately into *Y. lipolytica* strain Y4001 as described in Example 3. Transformant cells were plated onto MM plates lacking leucine and maintained at 30° C. for 2 to 3 days. Thus, transformants were obtained comprising the pALK2GUS, pALK2GUS-P8, pALK2GUS-P7, pALK2GUS-P3, and pALK2GUS-P4 plasmids, respectively.

Example 8

Comparative Analyses of 834 bp ALK2LM1, 646 bp ALK2LM-P8, 511 bp ALK2LM-P7, 364 bp ALK2LM-P3, and 242 bp ALK2LM-P4 Promoter Activities in *Yarrowia lipolytica* Strain Y4001

The promoter activities of the 834 bp ALK2LM1 (SEQ ID NO:15), 646 bp ALK2LM-P8 (SEQ ID NO:49), 511 bp ALK2LM-P7 (SEQ ID NO:51), 364 bp ALK2LM-P3 (SEQ ID NO:53), and 242 bp ALK2LM-P4 (SEQ ID NO:55) promoters were determined in *Yarrowia* transformants containing pALK2GUS, pALK2GUS-P8, pALK2GUS-P7, pALK2GUS-P3, and pALK2GUS-P4, respectively. GUS activity in each expressed construct was measured by histochemical assays as described in Example 4.

The results of histochemical staining showed that the activities of the 646 bp ALK2LM-P8 and 511 bp ALK2LM-P7 promoters were equivalent to the 834 bp ALK2LM1 promoter (SEQ ID NO:15, Example 4). Specifically, the 646 bp ALK2LM-P8 and 511 bp ALK2LM-P7 promoters were almost completely inactive when their respective transformed *Yarrowia* cells were grown in MM, but were very strongly active when their constructs were expressed by cells grown in nitrogen-limited HGM media. The 346 bp ALK2LM-P3 and 242 bp ALK2LM-P4 promoters were similarly inactive when their respective transformed *Yarrowia* cells were grown in MM, but were weakly active when their constructs were expressed by cells grown in nitrogen-limited HGM media. These results indicated that the DNA sequence responsible for nitrogen-limited induction was located between positions 324 and 470 of the ALK2LM1 promoter (SEQ ID NO:15) (corresponding to positions −511 and −364 respectively, in SEQ ID NO:1, where the 'A' of the ATG start codon is designated as +1). This particular sequence is set forth herein as SEQ ID NO:57.

Based on the above results, one of skill in the art will recognize that the ALK2LM promoter set forth as SEQ ID NO:11 can be truncated and retain promoter activity. Specifically, deleting the region defined by nucleotide positions 1 to 42 bp of SEQ ID NO:11 resulted in the active mutant promoter described herein as 834 bp ALK2LM1; deleting the region defined by nucleotide positions 1 to 109 bp of SEQ ID NO:11 resulted in the active mutant promoter described herein as 767 bp ALK2LM-C; deleting the region defined by nucleotide positions 1 to 230 bp of SEQ ID NO:11 resulted in the active mutant promoter described herein as 646 bp ALK2LM-P8; deleting the region defined by nucleotide positions 1 to 365 bp of SEQ ID NO:11 resulted in the active mutant promoter described herein as 511 bp ALK2LM-P7; deleting the region defined by nucleotide positions 1 to 512 bp of SEQ ID NO:11 resulted in the weakly active mutant promoter described herein as 364 bp ALK2LM-P3; and deleting the region defined by nucleotide positions 1 to 634 bp of SEQ ID NO:11 resulted in the weakly active mutant promoter described herein as 242 bp ALK2LM-P4 (FIG. 1). It is therefore assumed that a variety of modified ALK2 promoters could be utilized for expression of a coding region of interest in a *Yarrowia* host cell, wherein the promoter optionally comprises at least one modification selected from the group consisting of: a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:7. It is further assumed that SEQ ID NO:57 could be used as an enhancer to elevate levels of transcription of an operably linked eukaryotic promoter, thereby increasing transcription of an adjacent gene.

FIGS. 2A, 2B, 2C, 2D, 2E, 2F, 2G, 2H, 2I, and 2J is an alignment of the following *Y. lipolytica* ALK2 promoter regions described herein: the ALK2 (SEQ ID NO:2) promoter region, which is the 1000 bp 5' upstream sequence (i.e., the −1000 to −1 region) of the n-alkane-hydroxylating cytochrome P450 ["ALK2"] gene in *Y. lipolytica*, wherein the nucleotide 'A' of the ALK2 translation initiation codon 'ATG' was designated as +1; the 942 bp ALK2N (SEQ ID NO:6) promoter region, which comprises the 876 bp 5' upstream sequence (i.e., the −876 to −1 region) of the n-alkane-hy- droxylating cytochrome P450 ["ALK2"] gene and the first 66 bp of the protein coding region, wherein the nucleotide 'A' of the ALK2 translation initiation codon 'ATG' was designated as +1; the 876 bp ALK2L (SEQ ID NO:7) promoter region; the 876 bp ALK2LM (SEQ ID NO:11) promoter region; the 838 bp ALK2LM1-S (SEQ ID NO:27) promoter region; the 834 bp ALK2LM1 (SEQ ID NO:15) promoter region; the 840 bp ALK2LM1-PP6 (SEQ ID NO:47) promoter region; the 839 bp ALK2LM1-PP5 (SEQ ID NO:43) promoter region; the 837 bp ALK2LM1-PP2 (SEQ ID NO:39) promoter region; the 835 bp ALK2LM1-PP1 (SEQ ID NO:35) promoter region; the 835 bp ALK2LM1-P (SEQ ID NO:31) promoter region; the 767 bp ALK2LM-C (SEQ ID NO:19) promoter region; the 646 bp ALK2LM-P8 (SEQ ID NO:49) promoter region; the 511 bp ALK2LM-P7 (SEQ ID NO:51) promoter region; the 364 bp ALK2LM-P3 (SEQ ID NO:53) promoter region; the 242 bp ALK2LM-P4 (SEQ ID NO:55) promoter region; and the 68 bp minimal/core ALK2 (SEQ ID NO:56) promoter region. Sequence differences are noted with an arrow over the alignment and a box.

All of the modified promoters derived from the ALK2L promoter set forth as SEQ ID NO:7 (e.g., 876 bp ALK2LM, 646 bp ALK2LM-P8, 511 bp ALK2LM-P7, 364 bp ALK2LM-P3, and 242 bp ALK2LM-P4) comprise a cytosine ['C'] to guanine ['G'] substitution at the nucleotide corresponding to position 753 of SEQ ID NO:7. Therefore, one of skill in the art will appreciate that a suitable promoter region of an ALK2 *Yarrowia* gene may optionally comprise a cytosine ['C'] or a guanine ['G'] nucleotide at the nucleotide corresponding to position 753 of SEQ ID NO:7; alternately, the modified ALK2 promoter may also tolerate substitution of an adenine ['A'] nucleotide or a thymine ['T'] nucleotide for the wildtype cytosine ['C'] at this position.

Example 9

Sequence Analysis of Promoter Regions f an ALK2 *Yarrowia* Gene

This Example describes the analysis and definition of the ALK2 minimal promoter region.

Although promoters interact with the TATA binding protein ["TBP"] to create a transcription initiation complex from which RNA polymerase II transcribes the DNA coding sequence, only some promoters contain a TATA box to which TBP binds directly while other promoters are TATA-less promoters. The "TATA box" or "Goldberg-Hogness box" is a DNA sequence (i.e., cis-regulatory element) found in the promoter region of some genes in archaea and eukaryotes. For example, approximately 24% of human genes contain a TATA box within the core promoter (Yang C, et al., *Gene,* 389:52-65 (2007)); phylogenetic analysis of six *Saccharomyces* species revealed that about 20% of the 5,700 yeast genes contained a TATA-box element (Basehoar et al., *Cell,* 116: 699-709 (2004)). The TATA box has a core DNA sequence of 5'-TATAAA-3' or a variant thereof and is usually located ~200 to 25 base pairs upstream of the transcriptional start site. The transcription initiation complex forms at the site of the TATA box (Smale, and Kadonaga, T., *Ann. Rev. Biochem.* 72:449-479 (2003)). This complex comprises the TATA binding protein, RNA polymerase II, and various transcription factors (i.e., TFIID, TFIIA, TFIIB, TFIIF, TFIIE and TFIIH). Both the TATA box itself and the distance between the TATA box and transcription start site affect activity of TATA box-containing promoters in eukaryotes (Zhu et al., *Plant Cell* 7:1681-1689 (1995)).

The genes within *Yarrowia* can be largely classified into three classes according to their promoter sequences. Specifically, the first class of genes includes those comprising a TATA box, usually, ~130 to 20 base pairs upstream of the gene's transcription start site. The second class of genes includes those comprising an initiator element(s) around the gene's transcription start site. And, the third class of genes lacks both a TATA box and initiator element in the gene's promoter region.

Analysis of the sequence of the 942 bp ALK2N promoter region (Example 1, SEQ ID NO:6) revealed that it contains a typical TATA-box (TATATAA) at the nucleotides corresponding to positions −68 to −62 of SEQ ID NO:1, wherein the nucleotide 'A' of the ALK2 translation initiation codon 'ATG' was designated as +1. The 68 bp fragment 5' upstream spanning positions −68 to −1 of the ALK2 gene is believed to be necessary for promoter activity. Based on identification of this 68 bp fragment, it is believed that a suitable minimal ALK2 promoter region for basal level transcription initiation would comprise this fragment, set forth herein as SEQ ID NO:56.

Example 10

Comparison of Various *Yarrowia* ALK2 Promoter Regions

The present Example summarizes the relative activity of various ALK2 promoter regions exemplified in Examples 4, 6, and 8, above.

It was concluded that the ALK2 promoter is a very strong inducible promoter that can be used to drive high level expression of various genes in engineered *Yarrowia* strains under nitrogen-limited conditions, as shown in Table 5 below. The results also demonstrated the presence of an enhancer responsible for induced expression under nitrogen-limited conditions located between positions +511 to +365 of SEQ ID. NO:6.

TABLE 4

Summary of Relative Activity of Various ALK2 Promoter Regions

| Construct Comprising GUS Reporter | Promoter Operably Linked to GUS Reporter | Promoter Length | Promoter Activity Cultured in MM* | Cultured in MM + HGM** |
|---|---|---|---|---|
| pALK2GUS (SEQ ID NO: 20) | ALK2LM1 (SEQ ID NO: 15) | 834 bp | − | +++ |
| pT-ALK2Pro-(S)C (SEQ ID NO: 16) | ALK2LM-C (SEQ ID NO: 19) | 767 bp | − | +++ |
| pALK2GUS-S (SEQ ID NO: 26) | ALK2LM1-S (SEQ ID NO: 27) | 838 bp | − | +++ |
| pALK2GUS-P (SEQ ID NO: 30) | ALK2LM1-P (SEQ ID NO: 31) | 835 bp | − | +++ |
| pALK2GUS-P1 (SEQ ID NO: 34) | ALK2LM1-PP1 (SEQ ID NO: 35) | 835 bp | − | +++ |
| pALK2GUS-P2 (SEQ ID NO: 38) | ALK2LM1-PP2 (SEQ ID NO: 39) | 837 bp | − | +++ |
| pALK2GUS-P5 (SEQ ID NO: 42) | ALK2LM1-PP5 (SEQ ID NO: 43) | 839 bp | − | +++ |
| pALK2GUS-P6 (SEQ ID NO: 46) | ALK2LM1-PP6 (SEQ ID NO: 47) | 840 bp | − | +++ |
| pALK2GUS-P8 (SEQ ID NO: 48) | ALK2LM-P8 (SEQ ID NO: 49) | 646 bp | − | +++ |
| pALK2GUS-P7 (SEQ ID NO: 50) | ALK2LM-P7 (SEQ ID NO: 51) | 511 bp | − | +++ |
| pALK2GUS-P3 (SEQ ID NO: 52) | ALK2LM-P3 (SEQ ID NO: 53) | 364 bp | − | −/+ |
| pALK2GUS-P4 (SEQ ID NO: 55) | ALK2LM-P4 (SEQ ID NO: 55) | 242 bp | − | −/+ |

*Cultured In MM refers to 2 days growth in MM.

**Cultured in MM + HGM refers to 2 days growth in MM, followed by 3 days growth in HGM.

What is claimed is:

1. A method for the expression of a coding region in a transformed yeast cell comprising:
   a) providing a transformed yeast cell having a recombinant construct, wherein the recombinant construct comprises:
      (1) a promoter region of an ALK2 *Yarrowia* gene; and
      (2) a heterologous coding region that is expressible in the yeast cell;
      wherein the promoter region is operably linked to the coding region, and wherein the coding region encodes at least one omega-3 fatty acid or omega-6 fatty acid biosynthetic pathway enzyme; and
   b) growing the transformed yeast cell of step (a) under conditions whereby the recombinant construct of step (a) is expressed,
   wherein an omega-3 fatty acid or omega-6 fatty acid is produced by the transformed yeast cell grown in step (b).

2. The method according to claim 1, wherein the promoter region of the ALK2 *Yarrowia* gene comprises SEQ ID NO:56.

3. The method according to claim 1, wherein the promoter region of the ALK2 *Yarrowia* gene comprises SEQ ID NO:6, wherein said promoter optionally comprises at least one modification selected from the group consisting of:
   a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;

b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;

c) substitution of a guanine ['G'] nucleotide for the cytosine ['C'] nucleotide at position 753 of SEQ ID NO:6;

d) substitution of an adenine ['A'] nucleotide or a thymine ['T'] nucleotide for the cytosine ['C'] nucleotide at position 753 of SEQ ID NO:6;

e) substitution of the nucleotide sequence 'AA' for the nucleotide sequence 'TT' at positions 41 and 42 of SEQ ID NO:6;

f) insertion of the nucleotide sequence 'TCG' between positions 109 and 110 of SEQ ID NO:6;

g) insertion of the nucleotide sequence 'AAAT' between position 131 and position 132 of SEQ ID NO:6;

h) substitution of the nucleotide sequence 'AAA' for the nucleotide sequence 'TT' at positions 76 to 77 of SEQ ID NO:6;

i) substitution of the nucleotide sequence 'GTTT' for the nucleotide sequence 'AAAA' at positions 631 to 634 of SEQ ID NO:6;

j) insertion of the nucleotide sequence 'TA' between position 512 and position 513 of SEQ ID NO:6;

k) insertion of the nucleotide sequence 'TTTA' between position 365 and position 366 of SEQ ID NO:6;

l) insertion of the nucleotide sequence 'TTAAA' between position 230 and position 231 of SEQ ID NO:6; and m) any combination of part a), part b), part c), part d), part e), part f), part g), part h), part i), part j), part k), and part l).

4. The method according to claim 3, wherein the promoter region of the ALK2 *Yarrowia* gene comprises a sequence selected from the group consisting of SEQ ID NO:7, SEQ ID NO:11, SEQ ID NO:27, SEQ ID NO:15, SEQ ID NO:47, SEQ ID NO:43, SEQ ID NO:39, SEQ ID NO:35, SEQ ID NO:31, SEQ ID NO:19, SEQ ID NO:49, SEQ ID NO:51, SEQ ID NO:53 and SEQ ID NO:55.

5. The method according to claim 4, wherein the promoter region of the ALK2 *Yarrowia* gene comprises SEQ ID NO:55, and wherein said promoter region optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, or 174 consecutive nucleotides, wherein the first nucleotide deleted is the adenine nucleotide ['A'] at position 1 of SEQ ID NO:55; and b) a deletion of part (a) in combination with a substitution of a thymine ['T'] nucleotide, adenine ['A'] nucleotide or a cytosine ['C'] nucleotide for the guanine ['G'] nucleotide at position 119 of SEQ ID NO:55.

6. The method according to claim 1, wherein the transformed yeast cell is an oleaginous yeast cell.

7. The method of claim 6, wherein the oleaginous yeast cell is a member of a genus selected from the group consisting of *Yarrowia*, *Candida*, *Rhodotorula*, *Rhodosporidium*, *Cryptococcus*, *Trichosporon* and *Lipomyces*.

8. The method according to claim 1, wherein the promoter region of the ALK2 *Yarrowia* gene further (i) comprises an enhancer region set forth in SEQ ID NO:57, or (ii) is operably linked to said enhancer region.

9. The method according to claim 1, wherein the omega-3 fatty acid or omega-6 fatty acid biosynthetic pathway enzyme is selected from the group consisting of desaturases and elongases.

10. An isolated nucleic acid molecule comprising a promoter region as set forth in SEQ ID NO:6, wherein said promoter region optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, or 634 consecutive nucleotides, wherein the first nucleotide deleted is the adenine nucleotide ['A'] at position 1 of SEQ ID NO:6;

b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 consecutive nucleotides, wherein the first nucleotide deleted is the cytosine ['C'] nucleotide at position 942 of SEQ ID NO:6;

c) substitution of a guanine ['G'] nucleotide for the cytosine ['C'] nucleotide at position 753 of SEQ ID NO:6;

d) substitution of an adenine ['A'] nucleotide or a thymine ['T'] nucleotide for the cytosine ['C'] nucleotide at position 753 of SEQ ID NO:6;

e) substitution of the nucleotide sequence 'AA' for the nucleotide sequence 'TT' at positions 41 and 42 of SEQ ID NO:6;

f) insertion of the nucleotide sequence 'TCG' between positions 109 and 110 of SEQ ID NO:6;

g) insertion of the nucleotide sequence 'AAAT' between position 131 and position 132 of SEQ ID NO:6;

h) substitution of the nucleotide sequence 'AAA' for the nucleotide sequence 'TT' at positions 76 to 77 of SEQ ID NO:6;

i) substitution of the nucleotide sequence 'GTTT' for the nucleotide sequence 'AAAA' at positions 631 to 634 of SEQ ID NO:6;

j) insertion of the nucleotide sequence 'TA' between position 512 and position 513 of SEQ ID NO:6;

k) insertion of the nucleotide sequence 'TTTA' between position 365 and position 366 of SEQ ID NO:6;

l) insertion of the nucleotide sequence 'TTAAA' between position 230 and position 231 of SEQ ID NO:6; and m) any combination of part a), part b), part c), part d), part e), part f), part g), part h), part i), part j), part k), and part l);

and wherein said promoter region is operably linked to a heterologous coding region that encodes at least one omega-3 fatty acid or omega-6 fatty acid biosynthetic pathway enzyme.

11. The isolated nucleic acid molecule of claim 10, wherein the promoter region comprises a sequence selected from the group consisting of SEQ ID NO:7, SEQ ID NO:11, SEQ ID NO:27, SEQ ID NO:15, SEQ ID NO:47, SEQ ID NO:43, SEQ ID NO:39, SEQ ID NO:35, SEQ ID NO:31, SEQ ID NO:19, SEQ ID NO:49, SEQ ID NO:51, SEQ ID NO:53 and SEQ ID NO:55.

12. The isolated nucleic acid molecule of claim 10, wherein the promoter region further (i) comprises an enhancer region set forth in SEQ ID NO:57, or (ii) is operably linked to said enhancer region.

13. An isolated nucleic acid molecule comprising a promoter region comprising SEQ ID NO:56, wherein said promoter region is operably linked to a heterologous coding region that encodes at least one omega-3 fatty acid or omega-6 fatty acid biosynthetic pathway enzyme.

14. An isolated nucleic acid molecule comprising a promoter region that comprises SEQ ID NO:19, SEQ ID NO:49, SEQ ID NO:51, SEQ ID NO:53, or SEQ ID NO:55, wherein said promoter region is operably linked to a heterologous coding region that encodes a polypeptide.

15. The isolated nucleic acid molecule of claim 14, wherein the promoter region comprises SEQ ID NO:19.

16. The isolated nucleic acid molecule of claim 14, wherein the polypeptide is selected from the group consisting of: desaturases, elongases, acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-galactosidases, glucoamylases, alpha-glucosidases, beta-glucanases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases and xylanases.

\* \* \* \* \*